(12) United States Patent
Illig et al.

(10) Patent No.: US 8,815,867 B2
(45) Date of Patent: Aug. 26, 2014

(54) INHIBITORS OF C-FMS KINASE

(75) Inventors: Carl R. Illig, Phoenixville, PA (US);
Shelley K. Ballentine, Lansdale, PA (US); Jinsheng Chen, Exton, PA (US);
Renee Louise DesJarlais, Saint Davids, PA (US); Sanath K. Meegalla,
Boothwyn, PA (US); Mark Wall, Flourtown, PA (US); Kenneth Wilson,
Media, PA (US)

(73) Assignee: Janssen Pharmaceutica NV, Beerse (BE)

( * ) Notice: Subject to any disclaimer, the term of this patent is extended or adjusted under 35 U.S.C. 154(b) by 1375 days.

(21) Appl. No.: 11/736,653

(22) Filed: Apr. 18, 2007

(65) Prior Publication Data

US 2007/0249608 A1    Oct. 25, 2007

Related U.S. Application Data

(60) Provisional application No. 60/793,667, filed on Apr. 20, 2006.

(51) Int. Cl.
A61K 31/496       (2006.01)
C07D 403/10       (2006.01)

(52) U.S. Cl.
USPC .................................. 514/253.01; 544/370

(58) Field of Classification Search
USPC .............................. 544/370; 514/255, 253.01
See application file for complete search history.

(56) References Cited

U.S. PATENT DOCUMENTS

| | | | |
|---|---|---|---|
| 2,466,420 A | 4/1949 | Hagemeyer et al. |
| 3,226,394 A | 12/1965 | Schipper |
| 4,551,540 A | 11/1985 | Hechenbleikner et al. |
| 5,101,440 A | 3/1992 | Watanabe et al. |
| 5,190,541 A | 3/1993 | Abele et al. |
| 5,474,765 A | 12/1995 | Thorpe |
| 5,534,940 A | 7/1996 | Sato et al. |
| 5,666,164 A | 9/1997 | Kondo et al. |
| 5,762,918 A | 6/1998 | Thorpe |
| 5,855,866 A | 1/1999 | Thorpe et al. |
| 5,874,442 A | 2/1999 | Doll et al. |
| 5,940,132 A | 8/1999 | Kondo et al. |
| 5,944,718 A | 8/1999 | Austin et al. |
| 5,968,952 A | 10/1999 | Venet et al. |
| 6,037,350 A | 3/2000 | Venet et al. |
| 6,100,254 A | 8/2000 | Budde et al. |
| 6,117,432 A | 9/2000 | Ganne et al. |
| 6,169,096 B1 | 1/2001 | Venet et al. |
| 6,187,786 B1 | 2/2001 | Venet et al. |
| 6,235,746 B1 | 5/2001 | Davis et al. |
| 6,342,219 B1 | 1/2002 | Thorpe et al. |
| 6,346,625 B1 | 2/2002 | Karabelas et al. |
| 6,383,790 B1 | 5/2002 | Shokat |
| 6,420,387 B1 | 7/2002 | Venet et al. |
| 6,458,800 B1 | 10/2002 | Angibaud et al. |
| 6,596,746 B1 | 7/2003 | Das et al. |
| 6,692,491 B1 | 2/2004 | Phan |
| 6,710,781 B1 | 3/2004 | Sato |
| 6,987,119 B2 | 1/2006 | Gaiba et al. |
| 7,039,254 B1 | 5/2006 | Maenaka et al. |
| 7,157,456 B2 | 1/2007 | Straub et al. |
| 7,208,493 B2 | 4/2007 | Wrasidlo et al. |
| 7,427,683 B2 | 9/2008 | Player et al. |
| 7,429,603 B2 | 9/2008 | Player et al. |
| 7,645,755 B2 | 1/2010 | Illig et al. |
| 7,662,837 B2 | 2/2010 | Illig et al. |
| 7,790,724 B2 | 9/2010 | Player et al. |
| 7,795,279 B2 | 9/2010 | Ballentine et al. |
| 7,973,035 B2 | 7/2011 | Illig et al. |
| 2002/0016625 A1 | 2/2002 | Falotico et al. |
| 2002/0019414 A1 | 2/2002 | Altmann et al. |

(Continued)

FOREIGN PATENT DOCUMENTS

CN     101017260       8/2007
EP     1566379 A1      8/2005

(Continued)

OTHER PUBLICATIONS

Vippagunta et al., "Crystalline Solid", Advanced Drug Delivery Reviews 48 (2001) 3-26.*

(Continued)

*Primary Examiner* — Patricia L Morris

(57) ABSTRACT

The invention is directed to compounds of Formula I:

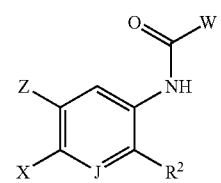

wherein Z, X, J, $R^2$ and W are set forth in the specification, as well as solvates, hydrates, tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, prostate cancer, lung cancer, colon cancer, stomach cancer, hairy cell leukemia; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including rheumatoid arthritis, and other forms of inflammatory arthritis, osteoarthritis, prosthesis failure, osteolytic sarcoma, myeloma, and tumor metastasis to bone with the compounds of Formula I, are also provided.

9 Claims, No Drawings

(56) References Cited

U.S. PATENT DOCUMENTS

| | | |
|---|---|---|
| 2002/0028028 A1 | 3/2002 | Michel |
| 2002/0119962 A1 | 8/2002 | Jacobs et al. |
| 2003/0130280 A1 | 7/2003 | O'Farrell et al. |
| 2003/0153610 A1 | 8/2003 | Straub et al. |
| 2003/0169247 A1 | 9/2003 | Kawabe et al. |
| 2004/0049032 A1 | 3/2004 | Charrier et al. |
| 2005/0004112 A1 | 1/2005 | Player et al. |
| 2005/0113566 A1 | 5/2005 | Player et al. |
| 2005/0184952 A1 | 8/2005 | Konno et al. |
| 2005/0219188 A1 | 10/2005 | Kawabe et al. |
| 2006/0040995 A1 | 2/2006 | Bacque et al. |
| 2006/0055661 A1 | 3/2006 | Kawaguchi |
| 2006/0100619 A1 | 5/2006 | McClurken et al. |
| 2006/0122181 A1 | 6/2006 | Ikemoto et al. |
| 2006/0132383 A1 | 6/2006 | Galley et al. |
| 2006/0148812 A1 | 7/2006 | Illig et al. |
| 2006/0189623 A1 | 8/2006 | Illig et al. |
| 2006/0258724 A1 | 11/2006 | Straub et al. |
| 2006/0281771 A1 | 12/2006 | Baumann et al. |
| 2006/0281788 A1 | 12/2006 | Baumann et al. |
| 2007/0121039 A1 | 5/2007 | Tago et al. |
| 2007/0179125 A1 | 8/2007 | Fraysse et al. |
| 2007/0182682 A1 | 8/2007 | Hong et al. |
| 2007/0249593 A1 | 10/2007 | Illig et al. |
| 2007/0249649 A1 | 10/2007 | Illig et al. |
| 2007/0249680 A1 | 10/2007 | Illig et al. |
| 2007/0249685 A1 | 10/2007 | Illig et al. |
| 2007/0259869 A1 | 11/2007 | Binch et al. |
| 2008/0051402 A1 | 2/2008 | Illig et al. |
| 2008/0068402 A1 | 3/2008 | Ioka et al. |
| 2008/0100554 A1 | 5/2008 | Mori |
| 2008/0106641 A1 | 5/2008 | Chou |
| 2008/0284719 A1 | 11/2008 | Yoshida |
| 2009/0105296 A1 | 4/2009 | Chen et al. |
| 2009/0197913 A1 | 8/2009 | Baumann et al. |
| 2011/0037785 A1 | 2/2011 | Shiomi |
| 2011/0195960 A1 | 8/2011 | Illig et al. |

FOREIGN PATENT DOCUMENTS

| | | |
|---|---|---|
| EP | 1705636 | 9/2006 |
| EP | 1936600 | 6/2008 |
| GB | 1189719 | 4/1970 |
| JP | 01/346070 | 12/2001 |
| JP | 3243861 | 1/2002 |
| JP | 02/064704 | 2/2002 |
| JP | 02/099250 | 4/2002 |
| JP | 03/255915 | 9/2003 |
| JP | 04/184937 | 7/2004 |
| JP | 04/212503 | 7/2004 |
| JP | 05/293265 | 10/2005 |
| JP | 05/309338 | 11/2005 |
| JP | 05/346639 | 12/2005 |
| JP | 06/84710 | 3/2006 |
| JP | 3766231 | 4/2006 |
| JP | 06/308665 | 11/2006 |
| JP | 07/140404 | 6/2007 |
| JP | 07/225871 | 9/2007 |
| JP | 07/310319 | 11/2007 |
| JP | 07/322944 | 12/2007 |
| JP | 08/021207 | 1/2008 |
| JP | 08/107715 | 5/2008 |
| JP | 08/116554 | 5/2008 |
| JP | 09/031585 | 2/2009 |
| JP | 08/287118 | 11/2009 |
| RU | 05/129914 | 4/2007 |
| WO | WO 94/10138 | 5/1994 |
| WO | WO 96/11932 | 4/1996 |
| WO | WO 96/21452 | 7/1996 |
| WO | WO 96/32907 | 10/1996 |
| WO | WO 97/16443 | 5/1997 |
| WO | WO 97/21701 | 6/1997 |
| WO | WO 97/30992 | 8/1997 |
| WO | WO 98/06700 | 2/1998 |
| WO | WO 98/28264 | 7/1998 |
| WO | WO 98/28303 | 7/1998 |
| WO | WO 98/40383 | 9/1998 |
| WO | WO 98/49157 | 11/1998 |
| WO | WO 98/54174 | 12/1998 |
| WO | WO 99/45712 | 9/1999 |
| WO | WO 99/45912 | 9/1999 |
| WO | WO 00/01691 | 1/2000 |
| WO | WO 00/02871 | 1/2000 |
| WO | WO 00/12498 | 3/2000 |
| WO | WO 00/12499 | 3/2000 |
| WO | WO 00/27820 | 5/2000 |
| WO | WO 00/39082 | 7/2000 |
| WO | WO 01/47897 | 7/2001 |
| WO | WO 01/47919 A1 | 7/2001 |
| WO | WO 01/49667 | 7/2001 |
| WO | WO 02/32861 A2 | 4/2002 |
| WO | WO 02/068406 | 9/2002 |
| WO | WO 02/092599 A1 | 11/2002 |
| WO | WO 03/024931 A1 | 3/2003 |
| WO | WO 03/024969 A1 | 3/2003 |
| WO | WO 03/035009 A2 | 5/2003 |
| WO | WO 03/037347 A1 | 5/2003 |
| WO | WO 03/057690 A1 | 7/2003 |
| WO | WO 03/099771 A2 | 12/2003 |
| WO | WO 03/099796 | 12/2003 |
| WO | WO 2004/005281 A1 | 1/2004 |
| WO | WO 2004/016597 A2 | 2/2004 |
| WO | WO 2004/018419 A2 | 3/2004 |
| WO | WO 2004/022525 | 3/2004 |
| WO | WO 2004/039782 A1 | 5/2004 |
| WO | WO 2004/043389 A2 | 5/2004 |
| WO | WO 2004/045548 | 6/2004 |
| WO | WO 2004/045549 | 6/2004 |
| WO | WO 2004/046120 A2 | 6/2004 |
| WO | WO 2004/058749 A1 | 7/2004 |
| WO | WO 2004/085388 | 10/2004 |
| WO | WO 2004/096795 | 11/2004 |
| WO | WO 2005/012220 | 2/2005 |
| WO | WO 2005/040139 | 5/2005 |
| WO | WO 2005/047273 | 5/2005 |
| WO | WO 2005/073225 | 8/2005 |
| WO | WO 2006/047277 A2 | 5/2006 |
| WO | WO 2006/047504 A1 | 5/2006 |
| WO | WO 2006/135630 | 12/2006 |
| WO | WO 2006/135636 | 12/2006 |
| WO | WO 2006/135713 | 12/2006 |
| WO | WO 2006/135718 | 12/2006 |
| WO | WO 2006/138155 A1 | 12/2006 |
| WO | WO 2007/048088 | 4/2007 |
| WO | WO 2009/058968 | 5/2009 |
| WO | 2009/157224 | 12/2009 |

OTHER PUBLICATIONS

Guillory (in Brittain ed.) Polymorphism, etc., NY: Marcel Dekker, Inc., 1999, 1-2, 183-226.*
International Search Report dated Oct. 10, 2007 for PCT/US2007/066875.
Abarbri et al., J. Org. Chem. (2000), 65, 4618-4634.
Abdel-Magid et al, "Reductive Amination of Aldehydes and Ketones with Sodium Triacetoxyborohydride.Studies on Direct and Indirect Reductive Amination Procedures", J Org. Chem., vol. 61 pp. 3849-3862 (1996).
Aboutaleb et al., International Sem in Surgical Oncol 6(17): 1-3, 2006.
Acute myeloid leukemia: MedlinePlus Medical Encyclopedia. Retrieved on Dec. 28, 2010. Electronic Resource: http://www.nlm.nih.gov/medlineplus/ency/article/000542.htm].
Advani, A., Curr Hematologic Malignancy Reports 1:101-107,2006.
Altman et al. The Cancer Dictionary, 1992, pp. 30-32.
Ansari-Lari, A. et al., "FLT3 mutations in myeloid sarcoma" British Journal of Haematology. Sep. 2004 126(6):785-91.
Armstrong, S.A. et al., (2004) "FLT3 mutations in childhood acute lymphoblastic leukemia." Blood. 103: 3544-6.
Arnon et al., "Monoclonal Antibodies for Immunotargeting of Drugs in Cancer Therapy", in Monoclonal Antibodies and Cancer Therapy, Reisfeld et al. (eds.), pp. 243- 56 (Alan R. Liss, Inc. 1985).

(56) References Cited

OTHER PUBLICATIONS

Auewarakul et al., Ann Hematol, 85:108-112, 2006.
Barkenbus et al., Journal of Organic Chemistry (1951), 16, 232-8.
Baumann et al.. J Biochem Biophys Methods. 2004; 60:69-79.
Beletskaya et al., *Chem. Rev.*, 100:3009 (2000).
Beller et al., Applied Homogeneous Catalysis with Organometallic Compounds, Cornils, B. and Herrmann, W. A. (Eds.), 2, 1009-1024, VCH, Weinheim, Germany (1996).
Berenbaum et al. What is synergy? Pharmacological Reviews, 1989.
Berge, S., et al, "Pharmaceutical Salts", J. Pharm. Sci., Jan. 1977, 66(1): 1-19.
Blouin et al. Rat models of bone metastases. Clin. Exp. Metastasis, 2005, 22: 605-614.
Bodansky, M. et al., "The Practice of Peptide Synthesis", Springer-Verlag, NY (1984).
Brase et al., *Angew. Chemie Int. Ed.*, 44(33), 5188-5240, (2005).
Brase et al., Metal-Catalyzed Cross-Coupling Reactions (2nd Edition), p. 217-315, A. de Meijere, F. Diederich, Eds., Wiley-VCH, Weinheim (2004).
British Journal of Haematology, "Flt3 mutations and leukemia", 2003,122(4):523-38.
Brown et al., J. Chem. Soc., Perkin Trans. 2, 1039-1051 (2002).
Buchner T., W. Hiddemann, et al. (2002). "Acute myeloid leukemia: treatment over 60." Rev Clin Exp Hematol. 6(1):46-59.
Buchwald, E.L. et al., Top. Curr. Chem., 219:131-209 (2001).
Burnett, A. K. (2002). "Acute myeloid leukemia: treatment of adults under 60 years." Rev Clin Exp Hematol 6(1): 26-45.
Byrn et al., Solid-State Chemistry of Drugs, Second Edition, 1999, pp. 233-247.
Canibano, V. et al., Synthesis 14, 2175 (2001).
ChemBlink. Tipifarnib. Electronic Resource. Retrived on 12/18/2010: [http://www.chemblink.com/products/192185-72-1.htm].
Chou TC, Talalay P. (1984) "Quantitative analysis of dose-effect relationships: the combined effects of multiple drugs or enzyme inhibitors." Adv Enzyme Regul. 22:27-55.
Clohlsy et al. Bone Cancer Pain. (Presented at the Third North American Symposium on Skeletal Complications of Malignancy, Bethesda, Maryland; Apr. 25-27, 2002).
Coll. Czech. Chem. Commun.: 31(11), 4432-41, (1966), Palecek, J. Comprehensive Organic Transformations: Larock, R.S.; Wiley and Sons Inc., USA 1999.
Corey et al., *Tetrahedron Lett.*, 29, 995 (1988).
Cortes. Farnesyltransferase inhibitors in acute myeloid leukemia and myelodysplastic syndromes. Clinical Lymphoma, vol. 4, Suppl. 1, S30-S35, 2003.
Couturier et al., *Organic Process Research & Development*, 2002, 6, 42-48.
Crandall et al., J. Am. Chem. Soc. (1968), 90, 6251-6253.
Cummins et al., Tetrahedron (1988), 44(16), 5151.
Dib, et al., European Journal of Pharmacology. 2006, pp. 27-33, 551.
Dirlam et al., *J. Heterocyclic Chem*, 17, 409, (1980).
Dolan, S., et al, *J. Chem., Soc., Chem. Commun.*, 1588-9 (1985).
Drexler, H. G. et al. (2004), "FLT3: receptor and ligand"; Growth Factors 22(2):71-3.
Drexler, H.G., "The Leukemia-Lymphoma Cell Line Factsbook", Academic Pres:SanDiego, CA, 2000.
Eastwood, P., Tetrahedron Lett. (2000), 41, 3705-8.
Ferrara et al., "Prognostic factors and therapeutic options for relapsed or refractory acute myeloid leukemia." Haematologica. Aug 2004, vol. 89, No. 8, Aug. 2004; pp. 998-1008.
Fohlisch et al, *Liebigs Annalen der Chemie*, (1), 1-5 (1987) [English Abstract provided].
Galemmo et al., *J. Med. Chem.*, 33(10), 2828-41; (1990).
Gavezzotti, "Are Crystal Structures Predictable?" Accounts of Chemical Research, vol. 27, pp. 309-314 (1994).
Gilliand, G., et.al, "The roles of FLT3 in mematopoiesis and leukemia", Blood. 2002; 100:1532-42.
Gotlib, J (2005) "Farnesyltransferase inhibitor therapy in acute myelogenous leukemia." Curr. Hematol. Rep.;4(1):77-84.

Gould, P., "Salt selection for basic drugs", Ref. International J. Pharm. 1986, 33, 201-217.
Gray, M. et al., Tetrahedron Lett., 41:6237-40 (2000).
Griswold, I. J. et al., "Effects of MLN518, A Dual FLT3 and Kit inhibitor, on Normal and Malignant Hematopoiesis" Blood, Jul. 2004 [Epub ahead of print].
Guanti et al., *Tetrahedron*, 46 (20), 7081, (1990).
Guanti et al., *Tetrahedron: Asymmetry* 8(13), 2175-2187, (1997).
Haluska P., G.K. Dy, A.A. Adjei. (2002) "Farnesyl transferase inhibitors as anticancer agents." Eur J Cancer. 38(13):1685-700.
Han, J., Advances in Characterization of Pharmaceutical Hydrates, Trends in Bio/PharmaceuticalIndustry, pp. 25-29. Mar. 2006.
Harmata et al., Org. Lett. (2000), 2, 2703-2705.
Hartwig, J.F., "Organopalladium Chemistry for Organic Synthesis," Wiley Interscience, NY (2002).
Hayakawa et al., *Bioorg. Med. Chem. Lett.*, 14(2): 455-8 (2004).
Hellstrom et al., "Antibodies for Drug Delivery", in Controlled Drug Delivery (2nd Ed.), Robinson et al. (eds.), pp. 623-653 (Marcel Dekker, Inc. 1987).
Hengartner, MO. (2000) "The biochemistry of apoptosis." Nature 407:770-76.
Hess et al., J. Am. Chem. Soc. (1998), 120, 12310.
Hill et al., J. Am. Chem. Soc. (1973), 95, 1338.
Hogermeier et al., Chem. Eur. J., 2007, 13, 2410.
Hulkenberg et al., *Tetrahedron Lett.*, 23(14), 1505-08; (1982).
Iddon. B. et al., J. Chem. Soc. Perkin Trans. 1., 1370, (1980).
Illig, et al., "Discovery of novel FMS Kinase Inhibitors As Antiinflammatory Agents" Bioorganic & Medicinal Chemistry Letters, Pergamon, 2008, pp. 1642-1648 vol. 18, No. 5.
Ishikubo et al (Jpn J Clin Oncol 36:494-498, 2006.
Itsuno et al., *Synthesis*, 12, 995-6, (1988).
Johnson et al., Brit J Cancer, 84:1424-1431 (2001).
Johnson et al., J. Org. Chem. (1970), 35(3), 584-592.
Kamwakami J., et al. "A Convenient Synthesis of 4(5)-Alkylacyl-1H-imidazoles from 4(5)-Imidazolecarboxaldehyde" Synthesis, No. 5, pp. 677-680 (2003).
Katritsky, A. et al., "*para*-Formylation of Nitroarenes via Vicarious Nucleophilic Substitution of Hydrogen with Tris(benzotriazol-1-yl)methane", Tetrahedron Lett., 37:347-50 (1996).
Khanapure et al, *J. Med. Chem.*, 48(11): 3930-34 (2005).
Kim et al., European Journal of Organic Chemistry (2000), 12, 2195-2201.
Kolder, C.R., et al, "Synthesis and Reactivity of 5-Chloro-2,4-Dihydrosypyridine", x Recl. Tray. Chim. Pays-Bas; 285 (1953).
Koutek, et al, *Synth. Commun.*, 6 (4), 305-8 (1976).
Lancet J.E., J.D. Rosenblatt, J.E. Karp. (2003) "Farnesyltransferase inhibitors and myeloid malignancies: phase I evidence of Zarnestra activity in high-risk leukemias." Semin Hematol. 39(3 Suppl 2):31-5.
Larock, R.C., Comprehensive Organic Transformations, $2^{nd}$ Ed., Wiley-VCH, NY, (1999), pp. 996-1003.
Lee, K. and Cha, J. K., J. Amer. Chem. Soc., 123: 5590-5591 (2001).
Leonard et al., *J. Org. Chem.*, 28, 3021, (1963).
Levis, M. et al. 2001, "A FLT3 tyrosine kinase inhibitor is selectively cytotoxic to acute myeloid leukemia blasts harboring FLT3 internal tandem duplication mutations", Blood 98(3):885-7.
Levis, M. et al., "Novel FLT3 tyrosine kinase inhibitors" Expert Opin. Investing. Drugs (2003) 12 (12) 1951-1962.
Levis, M. et al., "Small Molecule FLT3 Tyrosine Kinase Inhibitors" Current Pharmaceutical Design, 2004, 10, 1183-1193.
Levis, M., et al. (2004) "In vitro studies of a FLT3 inhibitor combined with chemotherapy: sequence of administration is important to achieve synergistic cytotoxic effects." Blood. 104(4):1145-50.
Lewis, et al. "Diacetoxypiperidinium Analogs of Acetylcholine", Junal of Medicinal Chemistry, 1973, vol. 16, No. 2 pp. 156-159.
Lipshutz et al., Tetrahedron Lett. (1988), 29, 3411-3414.
Liu et al., *J. Am. Chem. Soc.* 2004, 126, 5182.
Loader, C., et al, Can. J. Chem, 59, 2673 (1981).
Lovborg H, Gullbo J, Larsson R. (2005) "Screening for apoptosis-classical and emerging techniques." Anticancer Drugs 16:593-9.
Lyon, R., et al., "Synthesis and Evaluation of Phenyl-and Benzoylpiperazines as Potential Serotonergic Agents", J. Med. Chem., 29: 630-4 (1986).

(56) References Cited

OTHER PUBLICATIONS

Major, R., et al. "1-Alkoxy-4-phenyl-4-propionoxypiperdines and Their 3-Methyl Homologs as New Analgesics", vol. 26, pp. 1867-1847, (1961).
Martinez_Teipel et al., *QSAR & Combinatorial Science*, 23(10), 854-858 (2004).
McBee et al., Journal of the American Chemical Society (1957), 79, 2323-5.
McKenna, H.J. et al., "Mice lacking flt3 ligand having deficient hematopoiesis affecting hematopoietic progenitor cells, dendritic cells and natural killer cells", Blood Jun. 2000; 95:3489-3497.
Meltzer et al., Bioorganic & Medicinal Chemistry (2002), 10(11) and 3583-3591.
Miyaura, N. et al., "Palladium-Catalyzed Cross-Coupling Reactions of Organoboron Compounds", Chem. Rev. 95:2457 (1995).
Mock et al., *J. Phys. Org. Chem.*, 16(3), 175-182 (2003).
Modern Amination Methods: Ricci, A., Ed., Wiley-VCH: Weinheim, 2000.
Muci, et al., "Practical Palladium Catalysts for C-N and C-O Bond Formation", Top. Curr., Chem. 219-131-209 (2001).
Murata, K. et al., "Selective cytotoxic mechanism of GTP-14564, a novel tyrosine kinase inhibitor in leukemia cells expressing a constitutively active Fms-like tyrosine kinase 3 (FLT3)" J Biol Chem. Aug. 29, 2003; 278(35):32892-8.
Murata, K. et al., "Synthesis of Alkenylboronates via Palladium-Catalyzed Borylation of Alkenyl Triflates (or Iodindes) with Pinacolborane" Synthesis, 2000, No. 6, pp. 778-780.
Murray, et al., "SU11248 inhibits tumor growth and CSF-1R-dependent osteolysis in an experimental breast cancer bone metastasis model", Clinical & Experimental Metastasis, 2003, pp. 757-766, vol. 20, No. 8.
Myles et al., *J. Org. Chem.*, 55, 1636 (1990).
Nguyen et al., Tetrahedron, 62(4), 647-651; (2006).
Nicolai, E., et al., "New Process for the Synthesis of Imidazo[4-5-b] pyridine Derivatives as Potent Orally Active Thromboxane A$_2$ Receptor Antagonists", J. Heterocyclic Chemistry, 31, (73) (1994).
Nose et al., *Chem. Pharm. Bull.*, 38(8), 2097-101, (1990).
Noyori et al., Org. React., 1983, 29, 163.
Nunez G, Benedict MA, Hu Y, Inohara N. (1998) "Caspases: the proteases of the apoptotic pathway." Oncogene 17:3237-45.
O'Farrell, A.M. et al. "SU11248 is a novel FLT3 tyrosine kinase inhibitor with potent activity in vitro and in vivo" Blood, May 2003; 101:3597-3605.
Olah, G.A. et al., "Formylating Agents", Chemical Reviews, vol. 87, No. 4, 1987.
Prendergast et al., (2001) "Farnesyl Transferase Inhibtors: Mechanism and Applications" Expert Opin Investig Drugs. 10(12):2105-16.
Protecting Groups, P, Kocienski Thieme Medical Publishers, 2000.
Pure Appl. Chem., 1976, 45:13-30.
Quentmeier H, et al. FLT3 mutations in acute myeloid leukemia cell lines. Leukemia. Jan. 2003;17:120-124.
Quintard et al., *J. Org. Chem.*, 48: 1559-60 (1983).
Reed et al., *Synthetic Communications*, 20(4), 563-71, (1990).
Regan, J., et al., Structure-Activity Relationships of the p38* Map Kinsase Inhibitor 1-)5-*tert*-Butyl-2-*p*-tolyl-2h-pyrazol-3-yl)-3-[4-(2-morpholin-4-yl-ethoxy)naph-thalen-1-yl-)urea (BIRB 796)J. Med. Chem., 46:4676-86 (2003).
Reinecke et al., Chemistry-A European Journal (1995), 1(6), 368-73.
Romeo, G., et al, "New Pyrimido [5,4-b_indoles as Ligands for *1-Adrenoceptor Subtypes", J. Med. Chem., 46: 2877-2894 (2003).
Roush, W., *J. Am. Chem. Soc.* 102, 1390 (1980).
Sadick, M. et al., Analysis of Hereregulin-Induced ErbB2 Phosphorylation with a High-Throughput Kinase Receptor Activation Enzyme-Linked Immunosorbent Assay, Analytical Biochemistry. 1996; 235:207-214.
Sasaki et al., Tett. Lett. (1982), 23, 1693.
Sato et al., Bulletin of the Chemical Society of Japan (1983), 56(9), 2680-99.
Sato et al., Bulletin of the Chemical Society of Japan (1984), 57(9), 2515-25.
Scheijen, B. et al. (2002), "Tyrosine kinase oncogenes innormal hematopoiesis and hematological disease", Oncogene 21(21):3314-33.
Schmid et al., Helv. Chim. Acta. (1974), 57, 1883 [see English Summary provided].
Sendelbach, et al, Journal of Organic Chemistry (1999), 64(10), 3398-3408.
Shih L. Y. et al., (2004) "Internal tandem duplication of fms-like tyrosine kinase 3 is associated with poor outcome in patients with myelodysplastic syndrome." Cancer, 101; 989-98.
Simpson WG, The calcium channel blocker verapamil and cancer chemotherapy. Cell Calcium. Dec. 1985;6(6):449-67.
Smith, B. D. et al., "Single-agent CEP-701, a novel FLT3 inhibitor, shows biologic and clinical activity in patients with relapsed or refractory acute myeloid leukemia" Blood, May 2004; 103:3669-3676.
Smith, P, "The Curtius Reaction", Organic Reactions 3:337 (1947).
Stille, J.K., "The Palladium-Catalyzed Cross-Coupling Reactions of Organotin Reagents with Organic Electrophiles", Angew, Chem, Int. Ed. Engl., 25:508-524, 1986.
Stirewalt, D.L. et al. (2003), "The role of FLT3 in haematopoietic malignancies", NatRev Cancer 3(9):650-65.
Stone, R.M. et al. "PKC 412 FLT3 inhibitor therapy in AML: results of a phase II trial" An Hematol 2004; 83 Suppl 1:S89-90.
Sundermeier, U., Doebler, C. and Beller, M., Modern Oxidation Methods, Baeckvall, J. (Ed.)., 1-20, Wiley-Verlag (2004) Weinheim, Germany (2004).
Suzuki, A., "Metal-Catalyzed Coupling Reactions" F. Deiderich, P. Stang, Eds., Wiley-VCH, Weinheim (1998).
Takada, Y., et al. (2004). "Protein farnesyltransferase inhibitor (SCH 66336) abolishes NF-kappaB activation induced by various carcinogens and inflammatory stimuli leading to suppression of NF-kappaB-regulated gene expression and up-regulation of apoptosis."J Biol Chem 279, 26287-99.
Takahashi, K., et al, Chem. Lett. (2000), 126-7.
Takaya et al., J Amer Chem Soc, (1978), 100(6), 1765-77.
Thalhammer et al. Duration of second complete remission in patients with acute myeloid leukemia treated with chemotherapy: a retrospective single-center study. Ann. Hematology, 1996, 72: 216-222.
Thompson et al., Journal of Industrial and Engineering Chemistry (Washington, D. C.) (1952), 44,1659-62.
Thorpe, "Antibody Carriers of Cytotoxic Agents in Cancer Therapy: A Review", in Monoclonal Antibodies '84: Biological and Clinical Applications, Pinchera et al. (eds.), pp. 475-506 (1985).
Tohma et al., *Adv. Syn. Catalysis*, 346, 111-124 (2004).
Tse, K.F. et al., "Inhibition of FLT3-mediated transformation by use of a tyrosine kinase inhibitor" Leukemia, Jul. 15, 2001(7):1001-10.
van Engeland M., L.J. Nieland ,et al. (1998) "Annexin V-affinity assay: a review on an apoptosis detection system based on phosphatidylserine exposure." Cytometry. 31(1):1-9.
Walker et al, Dermatol 212:70-72, 2006 (Abstract Only).
West et al., J. Org. Chem (1993), 58, 6795-6803.
Wilson et al., Reducing Ion Channel Activity in a Series of 4-Heterocyclic Arylamide Fms Inhibitors, 20 Bioorg. & Med. Chem. Letts. 3925-3929 (2010).
Wroblewski et al., Journal of the American Chemical Society (1996), 118, 10168-10174.
Wustrow, et al, "Coupling of Arylboronic Acids with a Partially Reduced Pyridine Derivative" Synthesis, 993 (1991).
Wustrow et al., Tetrahedron Lett., 35, 61-4 (1994).
www.cancer.org (accessed online Mar. 2, 2010), "Can Acute Myeloid Luchemia (AML) Be Prevented?".
Yee et al. Synergistic effect of SU11248 with cytarabine or daunorubicin on FLT3 ITD-positive leukemic cells. Blood, 2004, 104: 4202-4209. Published online Aug. 10, 2004.
Yee, K.W.H. et al., "SU5416 and SU5614 inhibit kinase activity of wild-type and mutant FLT3 receptor tyrosine kinase" Blood, Sep. 2002; 100:2941-294.
Zhu et al. Farnesyltransferase inhibitor R115777 (Zarnestra, Tipifarnib) synergizes with paclitaxel to induce apoptosis and mitotic arrest and to inhibit tumor growth of multiple myeloma cells. Blood, vol. 105, No. 12, 4759-4766, Published online Feb. 22, 2005.

(56) References Cited

OTHER PUBLICATIONS

Chemcats RN 93730-20-2, Nov. 28, 1988.
Chemcats RN 443895-82-7 Apr. 24, 2003.
Chemcats RN 701272-70-0, Jan. 1, 2004.
Chemcats RN 712290-43, Jan. 1, 2004.
Jonas, Nilsson W. et al., "Solid-Phase Synthesis of Libraries Generated from a 4-Phenyl-2-carboxy-piperazine Scaffold", J. Comb. Chem., 2001, 3, 546-553.
Moffett, Robert Bruce et al., "Antiulcer Agents. p-Aminobenzamido Aromatic Compounds", Journal of Medicinal Chemistry, 1971, vol. 14, No. 10, pp. 963-968.
Nilsson et al., J. Comb. Chem., vol. 3, pp. 546-553 (2001).
Rastelli et al. J. Med. Chem., 2003, 46, 2834-2845.
U.S. Office Action mailed Jan. 24, 2013 for corresponding U.S. Appl. No. 12/736,660.
Abstract of Japanese Patent Publication JP06-178277 published on Jun. 24, 1994.

* cited by examiner

INHIBITORS OF C-FMS KINASE

CROSS REFERENCE TO RELATED APPLICATION

This application claims priority from U.S. Provisional Application Ser. No. 60/793,667, filed on Apr. 20, 2006, the contents of which are hereby incorporated by reference in their entirety.

BACKGROUND OF THE INVENTION

The invention relates to novel compounds that function as protein tyrosine kinase inhibitors. More particularly, the invention relates to novel compounds that function as inhibitors of c-fms kinase.

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

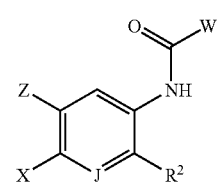

or a solvate, hydrate, tautomer or pharmaceutically acceptable salt thereof, wherein:
W is

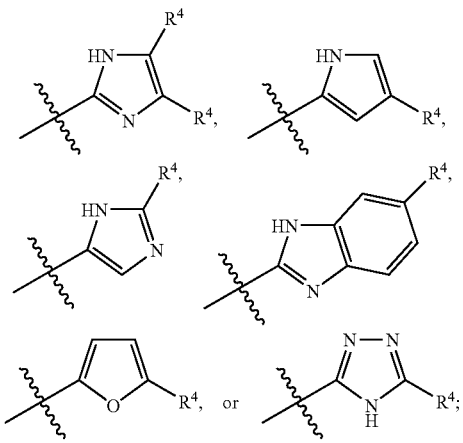

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, $CO_2R^d$, $CONR^eR^f$, C≡$CR^g$, or CN;
wherein $R^d$ is H, or —$C_{(1-3)}$alkyl;
$R^e$ is H, or —$C_{(1-3)}$alkyl;
$R^f$ is H, or —$C_{(1-3)}$alkyl; and
$R^g$ is H, —$CH_2OH$, or —$CH_2CH_2OH$;

$R^2$ is cycloalkyl, spiro-substituted cycloalkenyl, heterocyclyl, spirosubstituted piperidinyl, thiophenyl, dihydrosulfonopyranyl, phenyl, furanyl, tetrahydropyridyl, or dihydropyranyl, any of which may be independently substituted with one or two of each of the following: chloro, fluoro, hydroxy, $C_{(1-3)}$alkyl, and $C_{(1-4)}$alkyl;

Z is H, F, or $CH_3$;

J is CH, or N;

X is

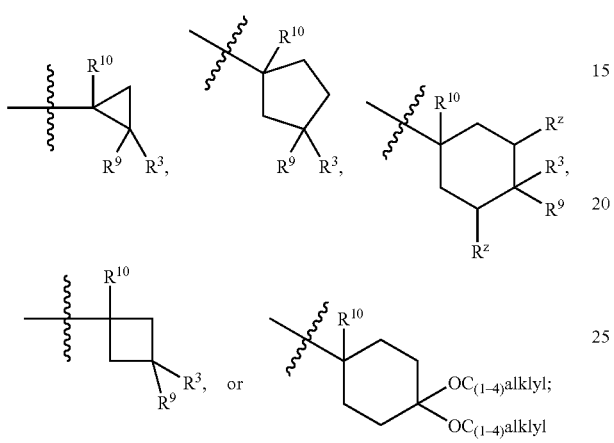

$R^z$ is H or —$C_{(1-4)}$alkyl, wherein both $R^z$ may have either syn or anti stereochemistry; alternatively both $R^z$ in a syn relationship may be taken together to form —$(CH_2)_n$—, where n is 2 or 3;

$R^3$ is H, $C_{(1-4)}$alkyl, $CH_2CH_2NH_2$, $CH_2CH_2OR^a$, —$COCH_3$, $CONH_2$, or $CO_2R^a$;

$R^9$ is H, $C_{(1-4)}$alkyl, $OR^a$, —$NA^1A^2$, $NA^1SO_2C_{(1-4)}$alkyl, $NA^1COC_{(1-4)}$alkyl, —$NHCH_2CH_2OCH_2CH_3$, —$N(CH_2CH_2OH)_2$, —$N(CH_3)CH_2CH_2OCH_3$, —$NHCH_2CH_2SO_2CH_3$, —$NHCH_2CON(CH_3)_2$, or $R^3$ and $R^9$ may be taken together to form oxo, —$OCH_2CH_2O$—, or —$OCH_2C(R^a)_2CH_2O$—;

$R^{10}$ is H, —$C_{(1-4)}$alkyl, —$OR^a$, —CN, —$NA^1A^2$, —$SO_2CH_3$, —$COOR^a$, —$CO_2CH_3$, —$CH_2$—$NA^1A^2$, —$CONA^1A^2$, —$CH_2OR^a$, —$OC_{(1-4)}$alkyl$OR^a$, —$NHCH_2CH_2CO_2R^a$, —$NHCH_2CH_2OR^a$, —$NR^aCH_2CH_2NA^1A^2$, —$OC_{(1-4)}$alkyl$NA^1A^2$, —$OCH_2CO_2R^a$, —$CH_2CO_2R^a$, —$CH_2CH_2SO_2C_{(1-4)}$alkyl, —$SO_2CH_2CH_2NA^1A^2$, —$SOCH_2CH_2NA^1A^2$, —$SCH_2CH_2NA^1A^2$, —$NHSO_2CH_2CH_2NA^1A^2$, phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

$A^1$ is H, —$C_{(1-4)}$alkyl, or $CH_2CH_2OR^a$;

$A^2$ is H, —$C_{(1-4)}$alkyl, $COR^a$, $CH_2CON(CH_3)_2$, —$CH_2CH_2OR^a$, —$CH_2CH_2SC_{(1-4)}$alkyl, —$CH_2CH_2SOC_{(1-4)}$alkyl, or —$CH_2CH_2SO_2C_{(1-4)}$alkyl;

alternatively, $A^1$ and $A^2$ may be taken together with their attached nitrogen to form a heterocyclic ring selected from the following:

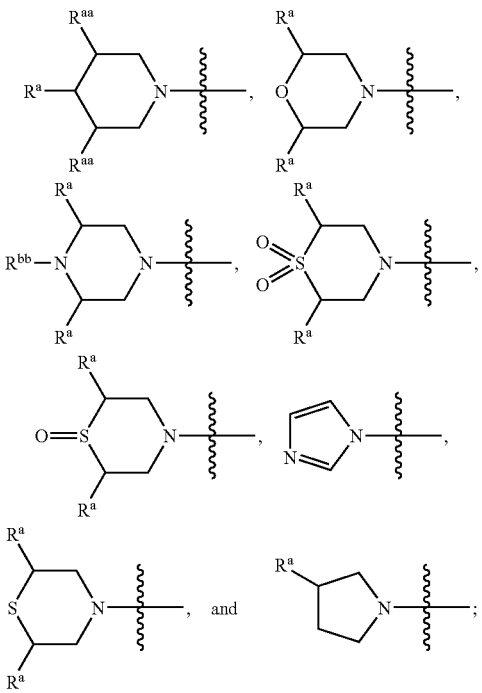

wherein $R^a$ is H or $C_{(1-4)}$alkyl;

$R^{aa}$ is H or $C_{(1-4)}$alkyl;

$R^{bb}$ is H, —$C_{(1-4)}$alkyl, —$CH_2CH_2OCH_2CH_2OCH_3$, —$CH_2CO_2H$, —$C(O)C_{(1-4)}$alkyl, or —$CH_2C(O)C_{(1-4)}$alkyl.

Herein and throughout this application, whenever a variable, for example $R^a$, appears more than once in an embodiment of Formula I, each such substitution is independently defined. Herein and throughout this application, the terms "Me", "Et", "Pr", and "Bu" refer to methyl, ethyl, propyl, and butyl respectively.

DETAILED DESCRIPTION OF THE INVENTION

The invention is directed to novel compounds of Formula I:

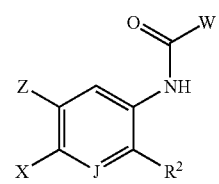

or a solvate, hydrate, tautomer or pharmaceutically acceptable salt thereof, wherein:

W is

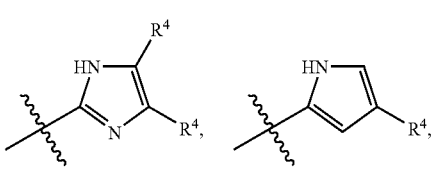

-continued

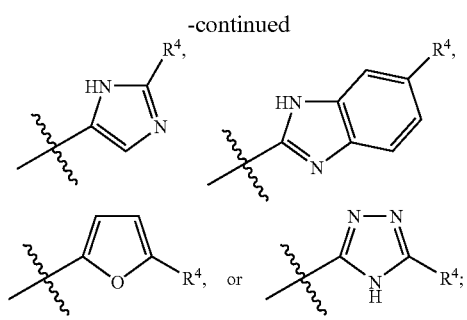

wherein each R⁴ is independently H, F, Cl, Br, I, OH, OCH₃, OCH₂CH₃, SC$_{(1-4)}$alkyl, SOC$_{(1-4)}$alkyl, SO₂C$_{(1-4)}$alkyl, —C$_{(1-3)}$alkyl, CO₂R$^d$, CONR$^e$R$^f$, C≡CR$^g$, or CN;
wherein R$^d$ is H, or —C$_{(1-3)}$alkyl;
R$^e$ is H, or —C$_{(1-3)}$alkyl;
R$^f$ is H, or —C$_{(1-3)}$alkyl; and
R$^g$ is H, —CH₂OH, or —CH₂CH₂OH;

R² is cycloalkyl (including cyclohexenyl, and cycloheptenyl), spiro-substituted cycloalkenyl (including spiro[2.5]oct-5-enyl, spiro[3.5]non-6-enyl, spiro[4.5]dec-7-enyl, and spiro[5.5]undec-2-enyl)heterocyclyl (including piperidinyl), spirosubstituted piperidinyl (including 3-aza-spiro[5.5]undecanyl, and 8-aza-spiro[4.5]decanyl), thiophenyl, dihydrosulfonopyranyl, phenyl, furanyl, tetrahydropyridyl, or dihydropyranyl, any of which may be independently substituted with one or two of each of the following: chloro, fluoro, hydroxy, C$_{(1-3)}$alkyl, and C$_{(1-4)}$alkyl (said substituted cycloalkyls include 4,4-dimethyl cyclohexenyl, 4,4-diethyl cyclohexenyl, 4-methyl cyclohexenyl, 4-ethyl cyclohexenyl, 4-n-propyl cyclohexenyl, 4-iso-propyl cyclohexenyl, and 4-tert-butyl cyclohexenyl; said substituted piperidinyls include 4-methyl piperidinyl, 4-ethyl piperidinyl, 4-(1'hydroxyeth-2'yl)piperidinyl, and 4,4 dimethyl piperidinyl);

Z is H, F, or CH₃;
J is CH, or N;
X is

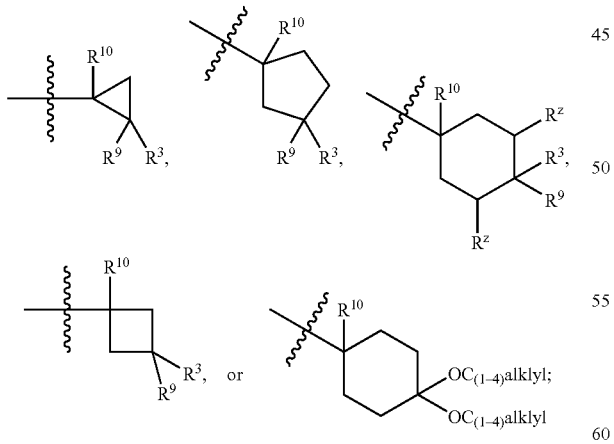

R$^z$ is H or —C$_{(1-4)}$alkyl, wherein both R$^z$ may have either syn or anti stereochemistry; alternatively both R$^z$ in a syn relationship may be taken together to form —(CH₂)$_n$—, where n is 2 or 3;

R³ is H, C$_{(1-4)}$alkyl, CH₂CH₂NH₂, CH₂CH₂OR$^a$, —COCH₃, CONH₂, or CO₂R$^a$;

R⁹ is H, C$_{(1-4)}$alkyl, OR$^a$, —NA¹A², NA¹SO₂C$_{(1-4)}$alkyl, NA¹COC$_{(1-4)}$alkyl, —NHCH₂CH₂OCH₂CH₃, —N(CH₂CH₂OH)₂, —N(CH₃)CH₂CH₂OCH₃, —NHCH₂CH₂SO₂CH₃, —NHCH₂CON(CH₃)₂, or R³ and R⁹ may be taken together to form oxo, —OCH₂CH₂O—, or —OCH₂C(R$^a$)₂CH₂O—;

R¹⁰ is H, —C$_{(1-4)}$alkyl, —OR$^a$, —CN, —NA¹A², —SO₂CH₃, —COOR$^a$, —CO₂CH₃, —CH₂—NA¹A², —CONA¹A², —CH₂OR$^a$, —OC$_{(1-4)}$alkylOR$^a$, —NHCH₂CH₂CO₂R$^a$, —NHCH₂CH₂OR$^a$, —NR$^a$CH₂CH₂NA¹A², —OC$_{(1-4)}$alkylNA¹A², —OCH₂CO₂R$^a$, —CH₂CO₂R$^a$, —CH₂CH₂SO₂C$_{(1-4)}$alkyl, —SO₂CH₂CH₂NA¹A², —SOCH₂CH₂NA¹A², —SCH₂CH₂NA¹A², —NHSO₂CH₂CH₂NA¹A², phenyl, imidazolyl, thiazolyl, 4H-[1,2,4]oxadiazol-5-onyl, 4H-pyrrolo[2,3-b]pyrazinyl, pyridinyl, [1,3,4]oxadiazolyl, 4H-[1,2,4]triazolyl, tetrazolyl, pyrazolyl, [1,3,5]triazinyl, and [1,3,4]thiadiazolyl;

A¹ is H, —C$_{(1-4)}$alkyl, or CH₂CH₂OR$^a$;

A² is H, —C$_{(1-4)}$alkyl, CORA, CH₂CON(CH₃)₂, —CH₂CH₂OR$^a$ (including —CH₂CH₂OCH₃), —CH₂CH₂SC$_{(1-4)}$alkyl (including —CH₂CH₂SCH₃), —CH₂CH₂SOC$_{(1-4)}$alkyl (including —CH₂CH₂SOCH₃), or —CH₂CH₂SO₂C$_{(1-4)}$alkyl (including —CH₂CH₂SO₂CH₃);

alternatively, A¹ and A² may be taken together with their attached nitrogen to form a heterocyclic ring selected from the following:

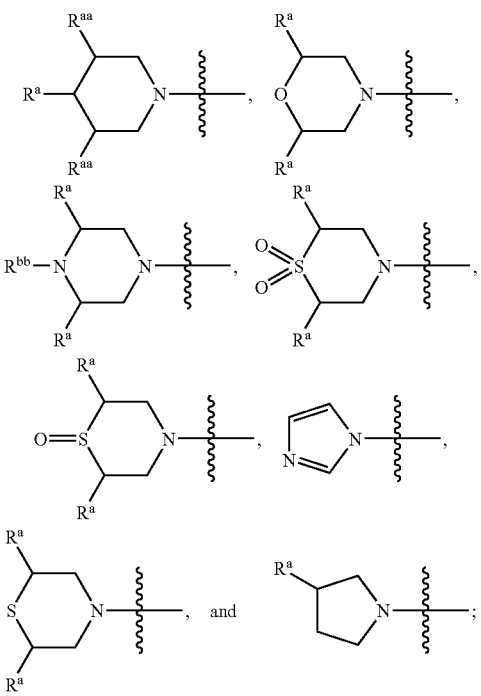

wherein R$^a$ is H or C$_{(1-4)}$alkyl;
R$^{aa}$ is H or C$_{(1-4)}$alkyl;
R$^{bb}$ is H, —C$_{(1-4)}$alkyl, —CH₂CH₂OCH₂CH₂OCH₃, —CH₂CO₂H, —C(O)C$_{(1-4)}$alkyl, or —CH₂C(O)C$_{(1-4)}$alkyl.

In a preferred embodiment of the invention:
W is

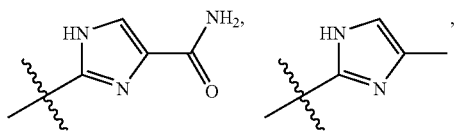
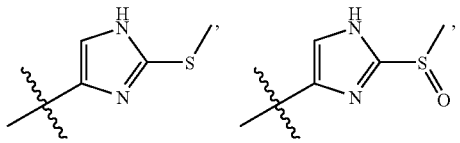
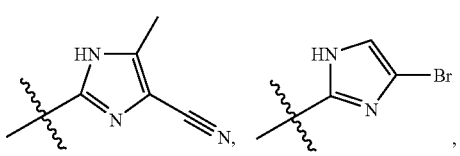
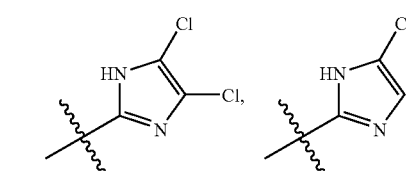
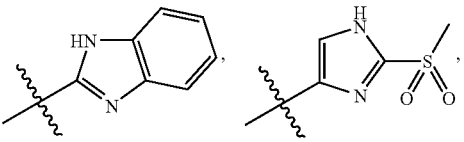

$R^2$ is

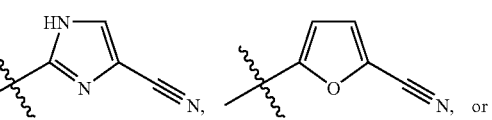
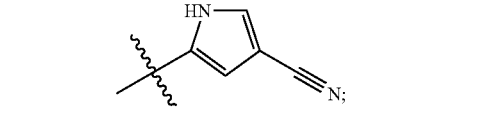
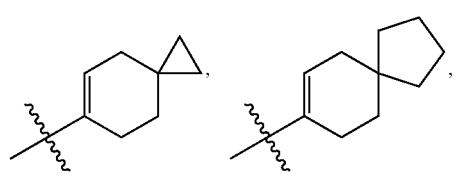
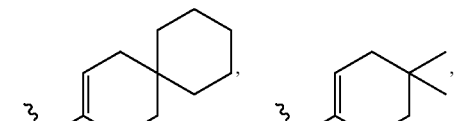

Z is H;
J is CH or N;
X is

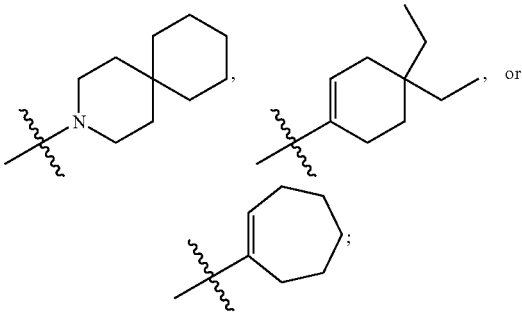
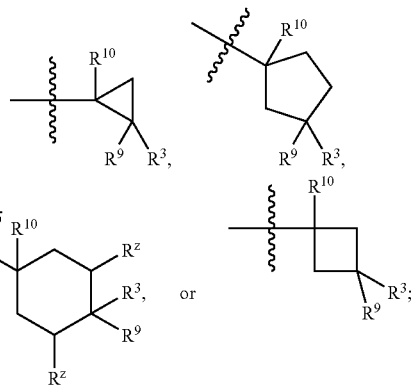

wherein $R^{10}$ is H, —CO$_2$H, —CN, —OH, —CH$_2$NH$_2$, —NA$^1$A$^2$, —OCH$_2$CH$_2$NA$^1$A$^2$, or —NR$^a$CH$_2$CH$_2$NA$^1$A$^2$;
A$^1$ is H, or —CH$_3$;
A$^2$ is H, —CH$_2$CH$_2$OCH$_3$, —COCH$_3$, or —CH$_3$;
alternatively, A$^1$ and A$^2$ may be taken together with their attached nitrogen to form a heterocyclic ring selected from the following:

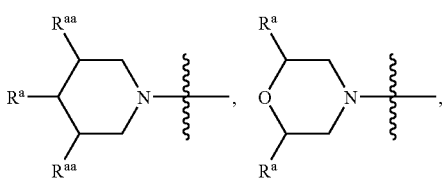

-continued

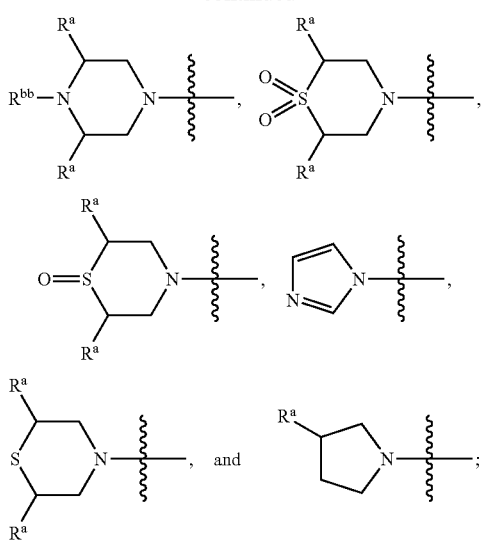

Rᵃ is H, or —C₍₁₋₄₎alkyl;
Rᵃᵃ is H, or —C₍₁₋₄₎alkyl;
Rᵇᵇ is H, —C₍₁₋₄₎alkyl, —CH₂CO₂H or —COCH₃;
Rᶻ is H, —CH₃, or may be taken together as —CH₂CH₂—;
R³ is H, —COCH₃, —CH₃, —CO₂CH₃, —CONH₂, or —CO₂H;
R⁹ is H, —OH, —N(CH₃)₂, —N(CH₂CH₃)₂, morpholinyl, N-methyl-piperazinyl, N-ethyl-piperazinyl, —NHCH₂CH₂OCH₂CH₃, —N(CH₂CH₂OH)₂, —N(CH₃)CH₂CH₂OCH₃, —NHCH₂CH₂SO₂CH₃, —NHCH₂CON(CH₃)₂, or R⁹ may be taken together with R³ to form oxo, or —OCH₂CH₂O—;

as well as solvates, hydrates, tautomers and pharmaceutically acceptable salts thereof.

In another embodiment of the invention:
W is

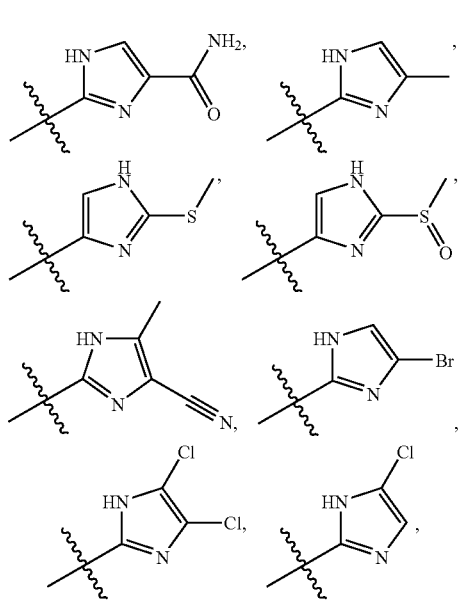

-continued

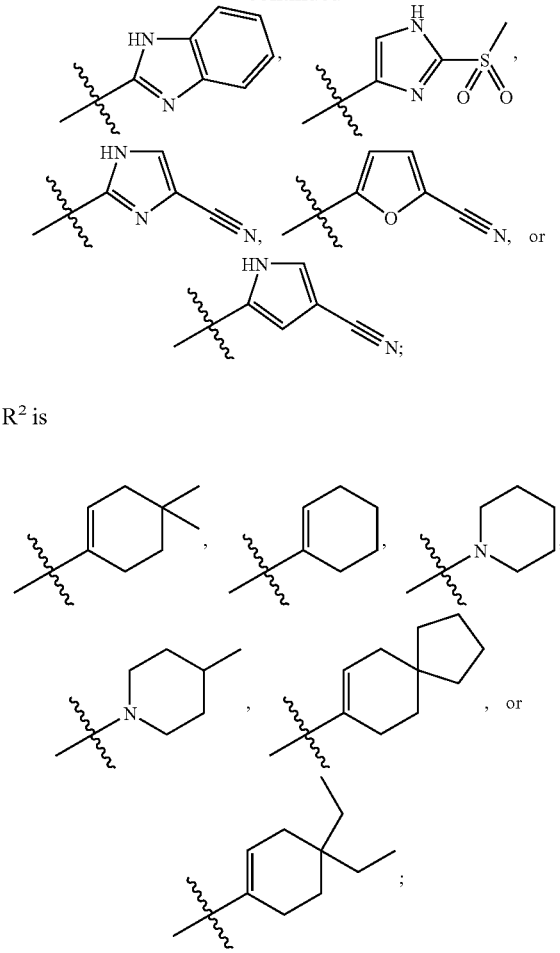

R² is

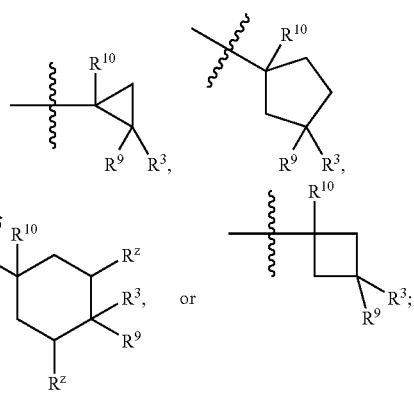

Z is H;
J is CH, or N;
X is

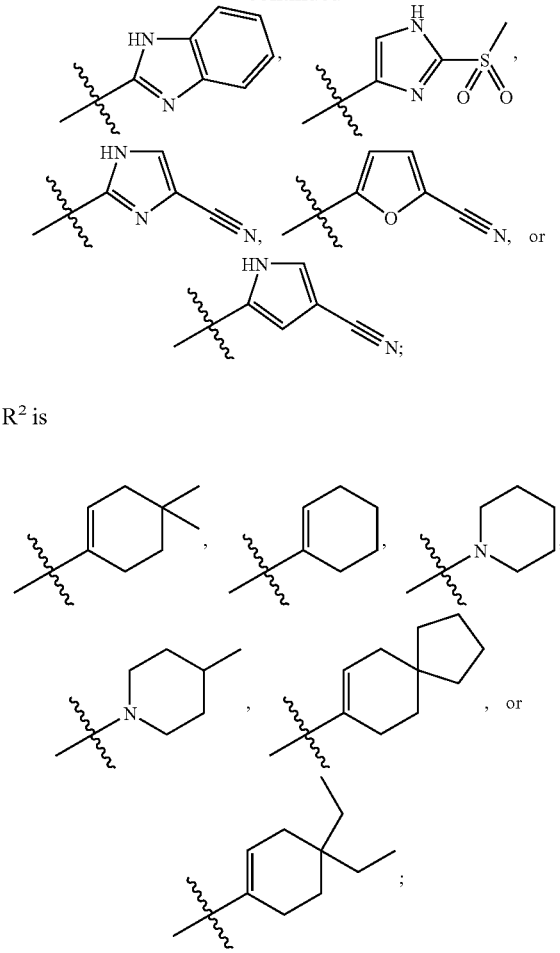

wherein R¹⁰ is H, —CO₂H, —CN, —OH, —CH₂NH₂, —NA¹A², —OCH₂CH₂NA¹A², or —NRᵃCH₂CH₂NA¹A²;
A¹ is H, or —CH₃;
A² is H, —CH₂CH₂OCH₃, —COCH₃, or —CH₃;
alternatively, A¹ and A² may be taken together with their attached nitrogen to form a heterocyclic ring selected from the following:

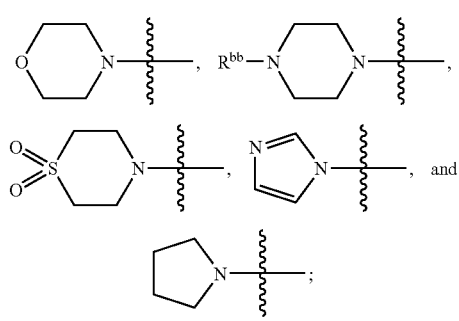

R$^{bb}$ is H, —C$_{(1-4)}$alkyl, —CH$_2$CO$_2$H or —COCH$_3$;

R$^z$ is H, —CH$_3$, or may be taken together as —CH$_2$CH$_2$—;

R$^3$ is H, —COCH$_3$, —CH$_3$, —CO$_2$CH$_3$, —CONH$_2$, or —CO$_2$H;

R$^9$ is H, —OH, —N(CH$_3$)$_2$, —N(CH$_2$CH$_3$)$_2$, morpholinyl, N-methyl-piperazinyl, N-ethyl-piperazinyl, —NHCH$_2$CH$_2$OCH$_2$CH$_3$, —N(CH$_2$CH$_2$OH)$_2$, —N(CH$_3$)CH$_2$CH$_2$OCH$_3$, —NHCH$_2$CH$_2$SO$_2$CH$_3$, —NHCH$_2$CON(CH$_3$)$_2$, or R$^9$ may be taken together with R$^3$ to form oxo, or —OCH$_2$CH$_2$O—;

as well as solvates, hydrates, tautomers and pharmaceutically acceptable salts thereof.

In another embodiment of the invention:

W is

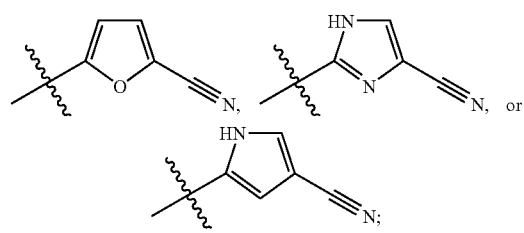

R$^2$ is

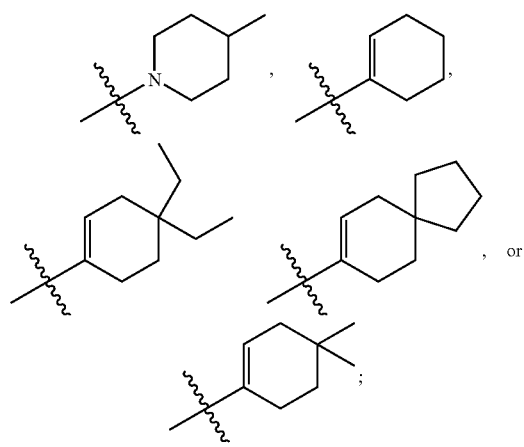

Z is H;

J is CH, or N;

X is

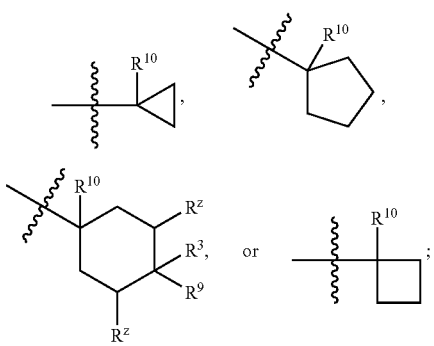

wherein R$^{10}$ is H, —CO$_2$H, —CN, —OH, —CH$_2$NH$_2$, —NA$^1$A$^2$, —OCH$_2$CH$_2$NA$^1$A$^2$, or —NR$^a$CH$_2$CH$_2$NA$^1$A$^2$;

A$^1$ is H, or —CH$_3$;

A$^2$ is H, —CH$_2$CH$_2$OCH$_3$, —COCH$_3$, or —CH$_3$;

alternatively, A$^1$ and A$^2$ may be taken together with their attached nitrogen to form a heterocyclic ring selected from the following:

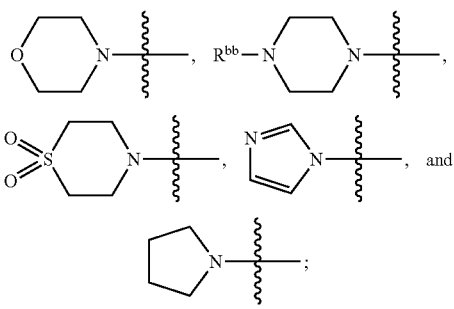

R$^{bb}$ is H, —C$_{(1-4)}$alkyl, —CH$_2$CO$_2$H or —COCH$_3$;

R$^z$ is H, —CH$_3$, or may be taken together as —CH$_2$CH$_2$—;

R$^3$ is H, —COCH$_3$, —CH$_3$, —CO$_2$CH$_3$, —CONH$_2$, or —CO$_2$H;

R$^9$ is H, —OH, —N(CH$_3$)$_2$, —N(CH$_2$CH$_3$)$_2$, morpholinyl, N-methyl-piperazinyl, N-ethyl-piperazinyl, —NHCH$_2$CH$_2$OCH$_2$CH$_3$, —N(CH$_2$CH$_2$OH)$_2$, —N(CH$_3$)CH$_2$CH$_2$OCH$_3$, —NHCH$_2$CH$_2$SO$_2$CH$_3$, —NHCH$_2$CON(CH$_3$)$_2$, or R$^9$ may be taken together with R$^3$ to form oxo, or —OCH$_2$CH$_2$O—;

as well as solvates, hydrates, tautomers and pharmaceutically acceptable salts thereof.

In another embodiment of the invention:

W is

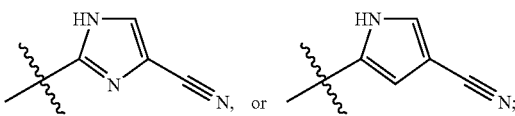

$R^2$ is

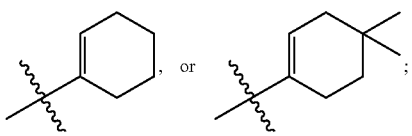

Z is H;
J is CH, or N;
X is

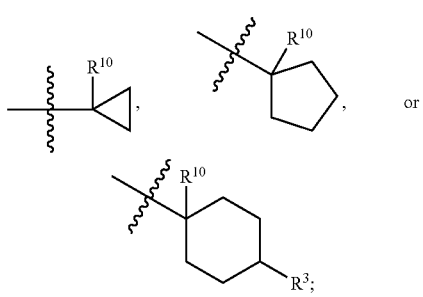

wherein $R^{10}$ is —CN, or —OH;
$R^3$ is —COCH$_3$, or —CO$_2$H;
as well as solvates, hydrates, tautomers and pharmaceutically acceptable salts thereof.

Yet another embodiment is the compounds of Examples 1 to 45, and solvates, hydrates, tautomers and pharmaceutically acceptable salts thereof, and any combination thereof.

Still another embodiment is compounds selected from the group consisting of:

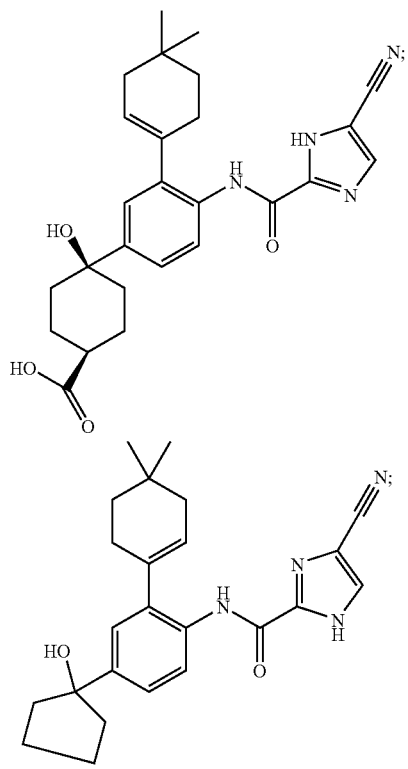

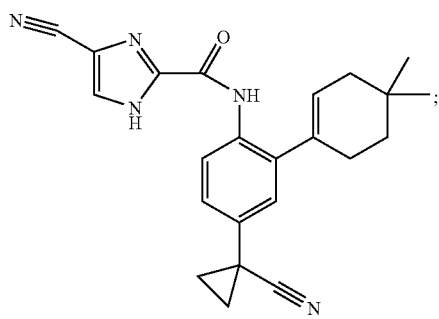

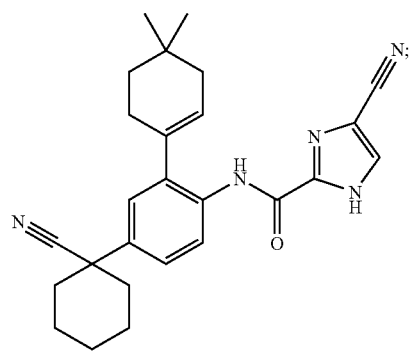

and solvates, hydrates, tautomers and pharmaceutically acceptable salts thereof.

Yet another embodiment is a compound selected from the group consisting of:

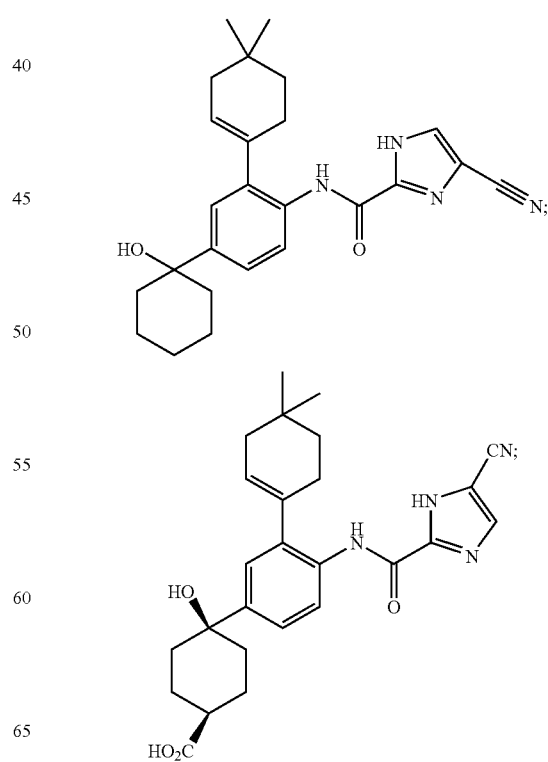

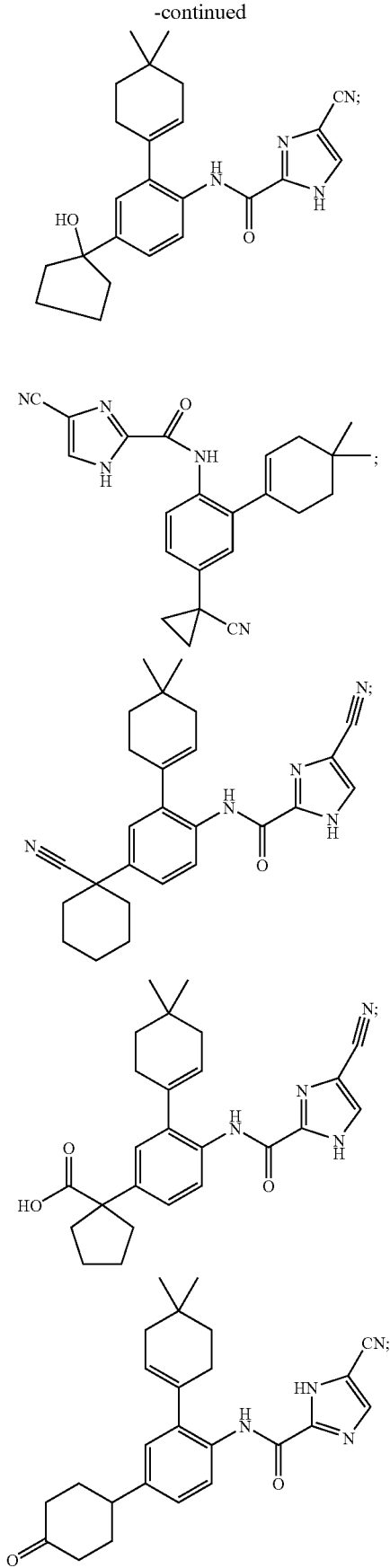
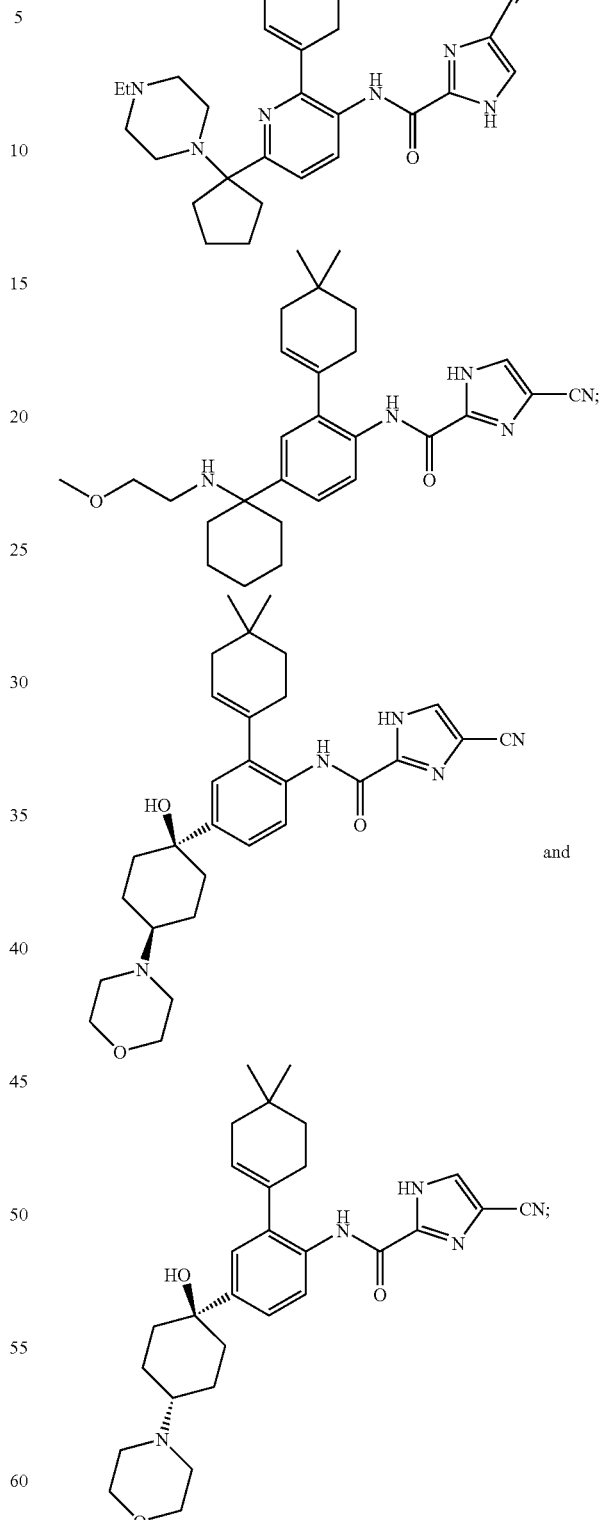
and solvates, hydrates, tautomers and pharmaceutically acceptable salts thereof.
The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formulae I may be prodrugs, i.e., derivatives of an acting drug that possess superior delivery capabilities and therapeutic value as compared to the acting drug. Prodrugs are transformed into active drugs by in vivo enzymatic or chemical processes.

I. Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamino" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl, cyclopentenyl, cyclohexenyl, and 4,4-dimethyl cyclohexenyl.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one alkyl substituent, wherein the amino group is the point of attachment to the rest of the molecule.

The term "dialkylamino" refers to an amino with two alkyl substituents, wherein the amino group is the point of attachment to the rest of the molecule.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and naphthalene.

The term "aralkyl" refers to a $C_{1-6}$ alkyl group containing an aryl substituent. Examples include benzyl, phenylethyl or 2-naphthylmethyl.

The term "sulfonyl" refers to the group —S(O)$_2$R$_a$, where R$_a$ is hydrogen, alkyl, cycloalkyl, haloalkyl, aryl, aralkyl, heteroaryl and heteroaralkyl. A "sulfonylating agent" adds the —S(O)$_2$R$_a$ group to a molecule.

The term "spiro-substituted cycloalkenyl" refers to a pair of cycloalkyl rings that share a single carbon atom and wherein at least one of the rings is partially unsaturated, for example:

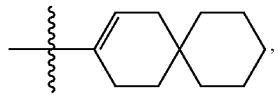

The term "spiro-substituted heterocyclyl" refers to a heterocyclyl and cycloalkyl ring that share a single carbon atom, for example:

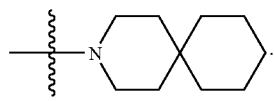

II. Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, prostate cancer, lung cancer, breast cancer, colon cancer, stomach cancer, and hairy cell leukemia. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, prostate cancer, lung cancer, breast cancer, colon cancer, stomach cancer, and hairy cell leukemia.

The invention further provides methods for the treatment osteoporosis, Paget's disease, and other diseases in which bone resorption mediates morbidity including rheumatoid arthritis and other forms of inflammatory arthritis, osteoarthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular, inflammatory, and autoimmune diseases in mammals, including humans, by administration of a therapeutically effective amount of a pharmaceutically acceptable form of at least one of the compounds of Formula I. Examples of diseases with an inflammatory component include glomerulonephritis, inflammatory bowel disease, prosthesis failure, sarcoidosis, congestive obstructive pulmonary disease, idiopathic pulmonary fibrosis, asthma, pancreatitis, HIV infection, psoriasis, diabetes, tumor related angiogenesis, age-related macular degeneration, diabetic retinopathy, restenosis, schizophrenia or Alzheimer's dementia. These may be effectively treated with compounds of this invention. Other diseases that may be effectively treated include, but are not limited to atherosclerosis and cardiac hypertrophy.

Autoimmune diseases such as systemic lupus erythematosus, rheumatoid arthritis, and other forms of inflammatory arthritis, psoriasis, Sjogren's syndrome, multiple sclerosis, or uveitis, can also be treated with compounds of this invention.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation, prevention, treatment, or the delay of the onset or progression of the symptoms of the disease or disorder being treated.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope solvates of the compounds of the present invention. Thus, in the methods of treatment of the present invention, the term "administering" shall encompass the means for treating, ameliorating or preventing a syndrome, disorder or disease described herein with the compounds of the present invention or a solvate thereof, which would obviously be included within the scope of the invention albeit not specifically disclosed.

Methods of Preparation

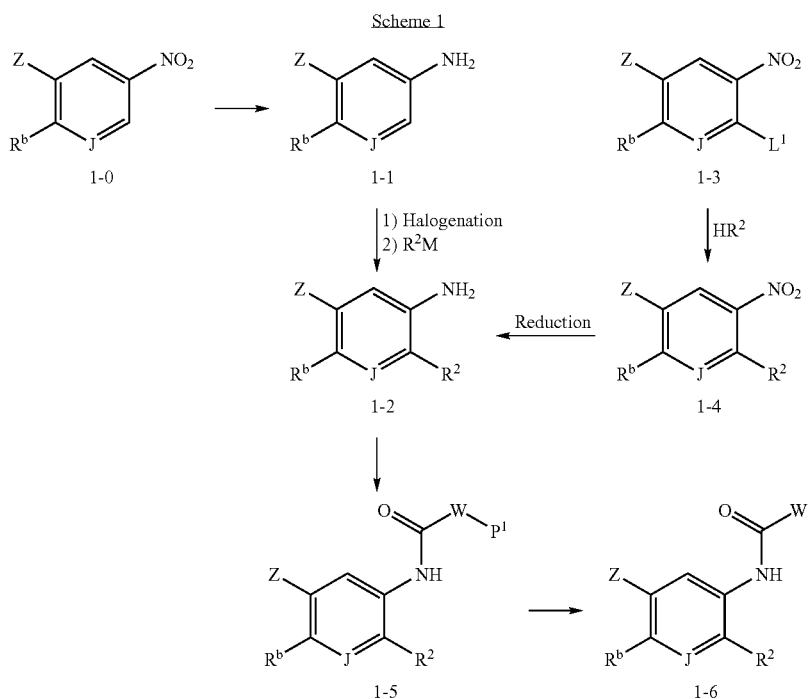

Scheme 1

Scheme 1 illustrates general methodology for the preparation or compounds or Formula I where $R^b$ is X (when X is available in starting material or prepared as shown in later schemes) or compounds of Formula 1-6 where $R^b$ is a leaving group (preferably bromo, chloro, or fluoro) that are useful intermediates used in later schemes. To illustrate the methodology of this scheme, reagents and conditions for the compounds where J is CH are defined. Those skilled in the art will recognize that where J is N, minor modifications of the reaction conditions and preferred reagents may be required.

Amines of Formula 1-1 may be commercially available or can be obtained from nitro compounds of Formula 1-0 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol. In cases where $R^b$ is a halogen and not available as amines of Formula 1-1, nitro reductions may be performed using iron or zinc in a suitable solvent such as acetic acid, or using iron and ammonium chloride in ethanol and water.

Compounds of Formula 1-2 where $R^2$ is cycloalkyl can be obtained by ortho-halogenation, preferably bromination, of amino compounds of Formula 1-1 followed by metal-catalyzed coupling reactions with boronic acids or boronate esters (Suzuki reactions, where $R^2M$ is $R^2B(OH)_2$ or a boronic ester, see N. Miyaura and A. Suzuki, Chem. Rev., 95:2457 (1995); A. Suzuki in Metal-Catalyzed Coupling Reactions, F. Deiderich, P. Stang, Eds., Wiley-VCH, Weinheim (1988)) or tin reagents (Stille reactions, where $R^2M$ is $R^2Sn(alkyl)_3$, see J. K. Stille, Angew. Chem, Int. Ed. Engl., 25: 508-524 (1986)) on the intermediate halo compound. When $R^b$ is Br, an iodo can be introduced such that it reacts preferentially over the bromine in the metal-catalyzed coupling reactions (when J is CH, this compound is commercially available). Preferred conditions for the bromination of 1-1 are N-bromosuccinimide (NBS) in a suitable solvent such as N,N-dimethylformamide (DMF), dichloromethane (DCM) or acetonitrile. Metal-catalyzed couplings, preferably Suzuki reactions, can be performed according to standard methodology, preferably in the presence of a palladium catalyst such as tetrakis(triphenylphosphine)palladium(0) ($Pd(PPh_3)_4$), an aqueous base such aq. $Na_2CO_3$, and a suitable solvent such as toluene, ethanol, 1,4-dioxane, dimethoxyethane (DME), or DMF.

Compounds of Formula 1-2 where $R^2$ is cycloalkylamino (for example, piperidino) can be obtained by nucleophilic aromatic substitution of leaving groups $L^1$ (preferably fluoro or chloro) from compounds of Formula 1-3 that are activated by the nitro group with cycloalkylamines ($R^2H$; for example, piperidine) in the presence of a suitable base such as $K_2CO_3$, N,N-diisopropylethylamine (DIEA) or $NEt_3$ to give compounds 1-4, followed by reduction of the nitro group as described above.

The amino group in compounds of Formula 1-2 can then be coupled with a heterocyclic acid $P^1$—WCOOH (or a corresponding salt thereof $P^1$—$WCOOM^2$, where $M^2$ is Li, Na or K) where $P^1$ is an optional protecting group (for example 2-(trimethylsilyl)ethoxymethyl (SEM) such as when W is imidazole, triazole, pyrrole, or benzimidazole) or where $P^1$ is not present such as when W is furan. (For a list of protecting groups for W, see Theodora W. Greene and Peter G. M. Wuts, Protective Groups in Organic Synthesis, John Wiley and Sons, Inc., NY (1991)). The coupling can be carried out according to standard procedures for amide bond formation (for a review, see: M. Bodansky and A. Bodansky, The Practice of Peptide Synthesis, Springer-Verlag, NY (1984)) or by reaction with acid chlorides $P^1$—WCOCl or activated esters $P^1$—$WCO_2R^q$ (where $R^q$ is a leaving group such as pentafluorophenyl or N-succinimide) to form compounds of Formula 1-5. The preferred reaction conditions for coupling with P¹—WCOOH or P¹—WCOOM² are: when W is a furan (optional protecting group P¹ not present), oxalyl chloride in dichloromethane (DCM) with DMF as a catalyst to form the acid chloride WCOCl and then coupling in the presence of a trialkylamine such as N,N-diisopropylethylamine (DIEA); when W is a pyrrole (optional protecting group P¹ not present), 1-(3-dimethylaminopropyl)-3-ethylcarbodiimide hydrochloride (EDCI) and 1-hydroxybenzotriazole (HOBt); and when W is an imidazole, pyrrole or benzimidazole (optional P¹ present) the preferred conditions are bromotripyrrolidinophosphonium hexafluorophosphate (PyBroP) and DIEA in a solvent such as DCM or DMF.

When W in compounds of Formula 1-5 contain an optional protecting group P¹ as mentioned previously, it can be removed at this point to give compounds of Formula 1-6. For example, when W is imidazole protected on nitrogen with a SEM group, the SEM group can be removed with either acidic reagents such as trifluoroacetic acid (TFA) or fluoride sources such as tetrabutylammonium fluoride (TBAF) (see Greene and Wuts above).

Finally it is understood that in compounds of Formula I (i.e., Formula 1-6 where $R^b$ is X) may be further derivatized. Examples of further derivatization, include, but are not limited to: when compounds of Formula I contain a cyano group, this group may be hydrolyzed to amides or acids under acidic or basic conditions; when compounds of Formula I contain an ester, the ester may be hydrolysed to the acid, and the acid may be converted to amides by the methods described above for amide bond formation. Amides may be converted to amines by a Curtius or Schmidt reaction (for review see, *Angew. Chemie Int. Ed.*, 44(33), 5188-5240, (2005)) or amines may be obtained by reduction of cyano groups (*Synthesis*, 12, 995-6, (1988) and *Chem. Pharm. Bull.*, 38(8), 2097-101, (1990)). Acids may be reduced to alcohols, and alcohols may be oxidized to aldehydes and ketones. The preferred conditions for the reduction of a carboxylic acid in the presence of a cyano group include sodium borohydride and ethyl chloroformate in tetrahydrofuran (THF); and alcohol oxidation can be performed using the Dess-Martin periodinane reagent (*Adv. Syn. Catalysis*, 346, 111-124 (2004)). Aldehydes and ketones may be reacted with primary or secondary amines in the presence of a reducing agent such as sodium triacetoxyborohydride (see *J. Org. Chem.*, 61, 3849-3862, (1996)) to give amines by reductive amination. Olefins may be reduced by catalytic hydrogenation. When compounds of Formula I contain a sulfide, either acyclic or cyclic, the sulfide can be further oxidized to the corresponding sulfoxides or sulfones. Sulfoxides can be obtained by oxidation using an appropriate oxidant such as one equivalent of meta-chloroperbenzoic acid (MCPBA) or by treatment with $NaIO_4$ (see, for example, *J. Med. Chem.*, 46: 4676-86 (2003)) and sulfones can be obtained using two equivalents of MCPBA or by treatment with 4-methylmorpholine N-oxide and catalytic osmium tetroxide (see, for example, PCT application WO 01/47919). Also, both sulfoxides and sulfones can be prepared by using one equivalent and two equivalents of $H_2O_2$ respectively, in the presence of titanium (IV) isopropoxide (see, for example, *J. Chem. Soc., Perkin Trans.* 2, 1039-1051 (2002)).

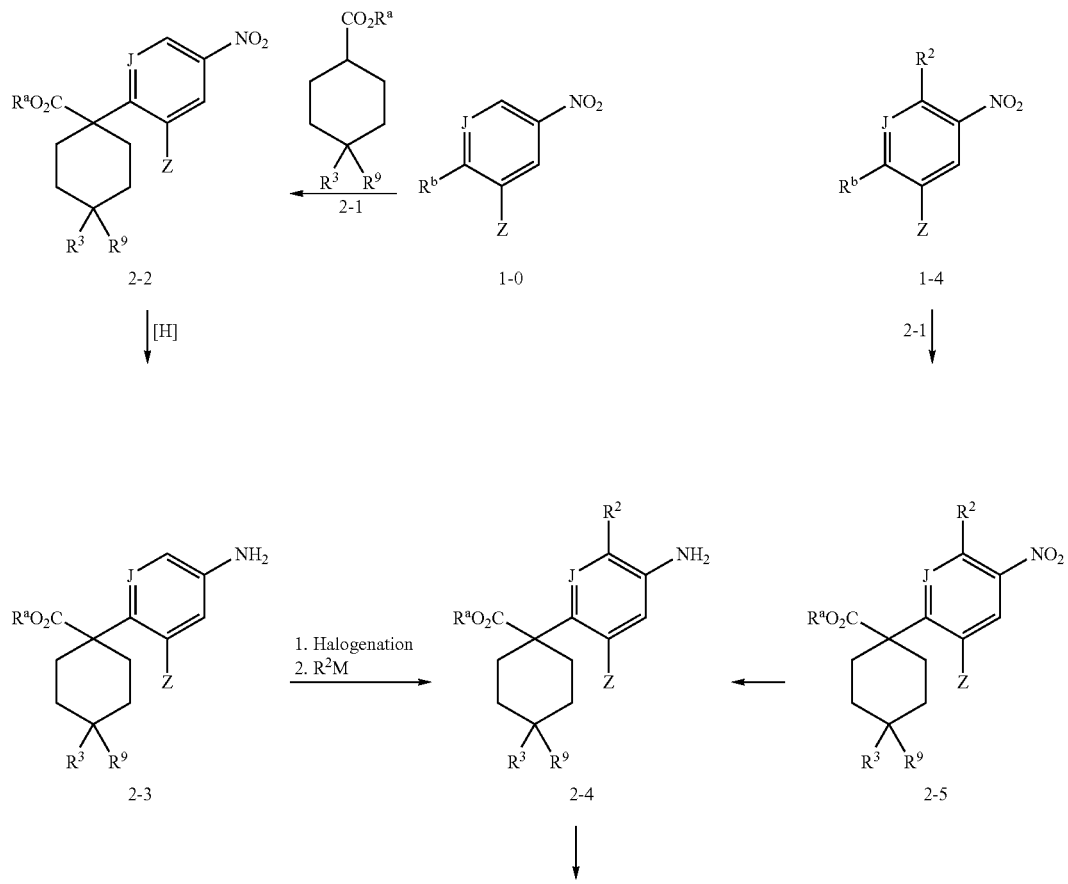

Scheme 2

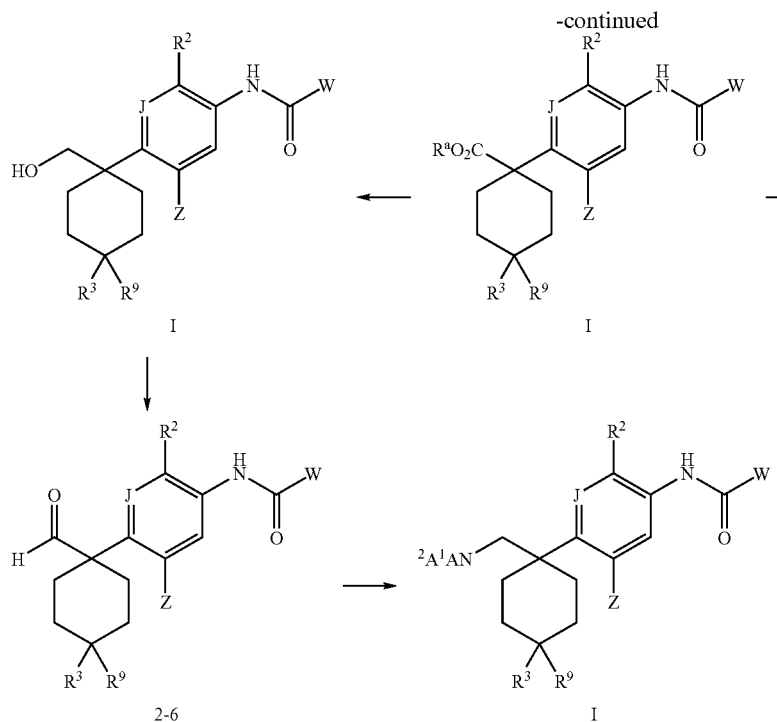

Scheme 2 illustrates general methodology for the preparation of compounds of Formula I where X is

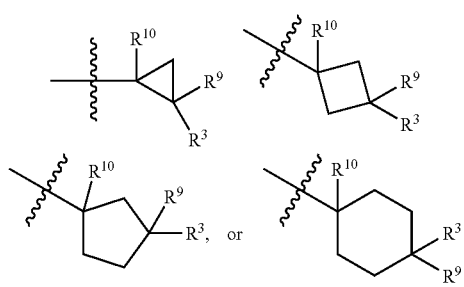

where $R^3$, $R^9$, and $R^z$ are H, $C_{(1-4)}$alkyl or $OR^a$; $R^{10}$ is $CO_2R^a$, $CH_2OH$, $C(O)NA^1A^2$ and $CH_2 NA^1A^2$ For the illustration of synthetic strategy in this scheme, reagents and conditions are defined for the substrate where is $R^z$ is H is used in this scheme. Those skilled in the art will recognize that the chemistry is applicable to all X and $R^z$ mentioned with little or minor modifications to reagents and conditions. In addition, although reagents and conditions are defined for the substrate where J is CH, as previously mentioned in Scheme 1, it is also understood that similar synthetic methods can be utilized with minor modifications when J is N.

When $R^2$ in Formula I is cycloalkyl (including cycloalkenyl), the sequence begins with compound 2-2 which can be obtained by initial treatment of the ester 2-1 ($R^a$ is $C_{(1-4)}$alkyl) with a suitable base such as lithium hexamethyldidilylamide (LHMDS) or preferably lithium diisopropylamide (LDA), followed by nucleophilic aromatic substitution of the leaving group $R^b$ (preferably fluoro or chloro) in the 4-halonitrophenyl compound 1-0 (as prepared in Scheme 1) with the resulting anion intermediate.

2-3 can be obtained from nitro compounds 2-2 by reduction using standard synthetic methodology (see Reductions in Organic Chemistry, M. Hudlicky, Wiley, New York, 1984). The preferred conditions are catalytic hydrogenation using a palladium catalyst in a suitable solvent such as methanol or ethanol.

Compound 2-4 can be obtained by ortho-halogenation, preferably bromination, of amino compound 2-4 followed by metal-catalyzed coupling reactions with boronic acid or boronate ester (Suzuki reactions, where $R^2M$ is $R^2B(OH)_2$ or a boronic ester) or tin reagent (Stille reactions, where $R^2M$ is $R^2Sn(alkyl)_3$) on the intermediate halo compound as described in Scheme 1.

When $R^2$ in Formula I is cycloalkylamino (for example, piperidino), an alternative method to prepare compound 2-4 begins with starting material 1-4 as described in Scheme 1 where $R^b$ is preferably chloro or fluoro. Compound 2-5 can be obtained from 1-4 and 2-1 by the same method as described for the conversion of compound 1-0 to compound 2-2. Compound 2-4 can then be obtained from compound 2-5 by reduction of the nitro group using standard synthetic methodology as described in Scheme 1 for the conversion of compound 1-0 to compound 1-1.

The compounds of Formula I where $R^{10}$ is an ester ($R^a$ is $C_{(1-4)}$alkyl) can be obtained from 2-4 by initial coupling with carboxylic acids $P^1$—WCOOH, followed by removal of the optional protecting group $P^1$ according to the procedures as described in Scheme 1 for the conversion of 1-2 to 1-6.

These compounds of Formula I where $R^{10}$ is an ester ($R^a$ is $C_{(1-4)}$alkyl) can be further hydrolyzed by an appropriate metal hydroxide reagent such as sodium hydroxide to give compounds of Formula I where $R^{10}$ is an acid ($R^a$ is H).

The compounds of Formula I where $R^{10}$ is an amide ($R^{10}$ is $C(O)NR^5R^6$) can be obtained from the compounds of Formula I where $R^{10}$ is an acid ($R^a$ is H) by initial treatment with an alkyl chloroformate, such as ethyl chloroformate, followed by trapping of the intermediate activated acylcarbonate with a suitable primary or secondary amine ($HNA^1A^2$). Similarly, compounds of Formula I where $R^{10}$ is a hydroxymethyl group can be obtained by reaction of the same intermediate activated acylcarbonate with a suitable reducing reagent such as $NaBH_4$ (see, for example, *Tetrahedron*, 62(4), 647-651; (2006)).

Compounds of Formula I where $R^{10}$ is a hydroxymethyl ($R^{10}$ is $CH_2OH$) can be further converted to the aldehyde 2-6 by oxidation reactions such as a Swern oxidation (*J. Am. Chem. Soc.* 102, 1390 (1980)) or preferably a Dess-Martin periodinane oxidation (see, for example, *Tetrahedron Lett.*, 29, 995 (1988); *J. Org. Chem.*, 55, 1636 (1990)).

Aldehyde 2-6 can be reacted with appropriate primary and secondary amines ($HNA^1A^2$) in the presence of suitable reducing reagents such as $NaBH_4$ or $NaBH_3CN$, or preferably $NaBH(OAc)_3$ according to standard procedures for reductive amination as described in Scheme 1, to form compounds of Formula I where $R^{10}$ is an aminomethyl group ($R^{10}$ is $CH_2NA^1A^2$).

It is understood that functional groups of compounds in this scheme can be further derivatized as outlined in Scheme 1.

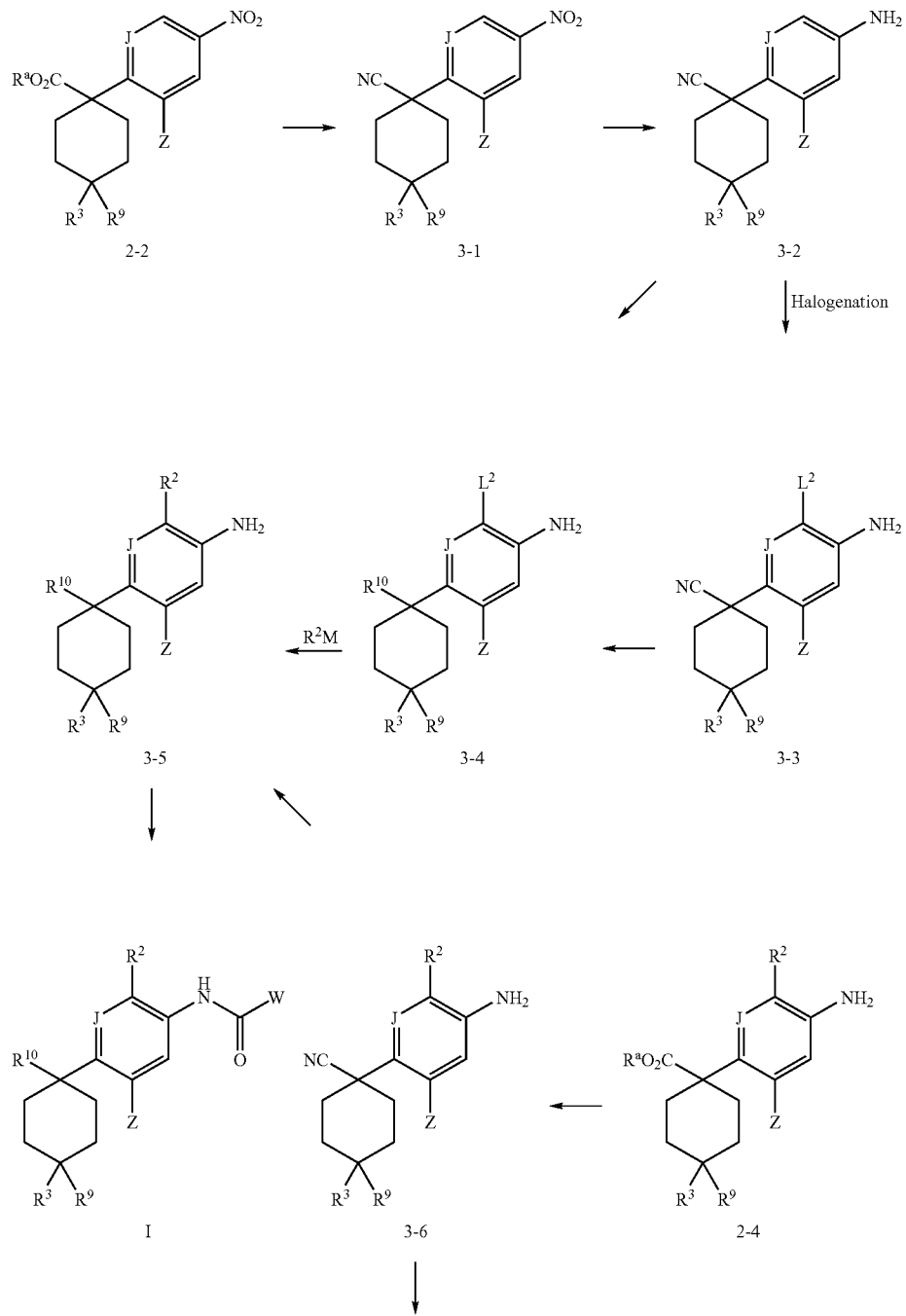

Scheme 3

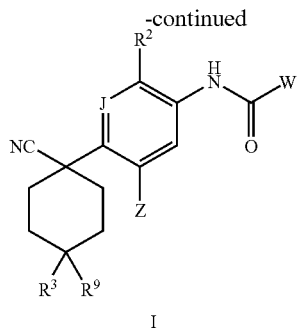

I

Scheme 3 illustrates general methodology for the preparation of compounds of Formula I where X is

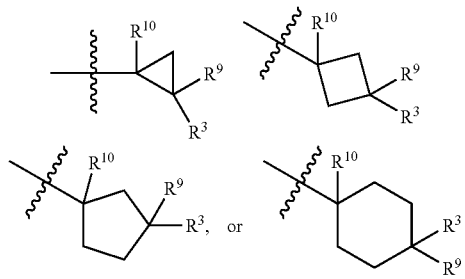

where $R^3$, $R^9$, and $R^z$ are H, $C_{(1-4)}$alkyl or $OR^a$; $R^{10}$ is —CN or heteroaryl.

For the illustration of synthetic strategy in this scheme, reagents and conditions are defined for the substrate where $R^z$ is H is used in this scheme. Those skilled in the art will recognize that the chemistry is applicable to all X and $R^z$ mentioned with little or minor modifications to reagents and conditions. In addition, although reagents and conditions are defined for the substrate where J is CH, as previously mentioned in Scheme 1, it is also understood that similar synthetic methods can be utilized with minor modifications when J is N.

The ester 2-2 ($R^a$ is $C_{(1-4)}$alkyl) can be hydrolyzed by an appropriate metal hydroxide reagent such as sodium hydroxide to give acid 2-2 ($R^a$ is H). The acid 2-2 can be converted to nitrile 3-1 by standard procedures which, in general, begin with activation of the acid, transformation into an amide or hydroxamate followed by dehydration (see, for example, *J. Med. Chem.*, 33(10), 2828-41; (1990)), or preferably in one step by treatment with sulfonamide and thionyl chloride in a suitable solvent such as sulfolane (see, *Tetrahedron Lett.*, 23(14), 1505-08; (1982)). Compound 3-2 can obtained from 3-1 by standard reduction procedures, preferably catalytic hydrogenation as described in Scheme 1.

The compound 3-3 ($L^2$ is halogen) can be obtained by ortho-halogenation, preferably bromination, of amine 3-2. Preferred conditions for the bromination of 3-2 are N-bromosuccinimide (NBS) in a suitable solvent such as N,N-dimethylformamide (DMF), dichloromethane (DCM) or acetonitrile.

At this point the cyano group in 3-3 can be converted to an unsaturated heterocycle in 3-4 by [2+3] cycloaddition with a 1,3 dipole or [2+4] cycloaddition with a diene or heterodiene as illustrated in Scheme 3a. The various heterocycles that can be produced are shown in Table 1 using the conditions in the references provided in the table.

When the unsaturated heterocycle present is unreactive toward halogenation, an alternative route to 3-4 involves treatment of nitrile 3-2 as just described to first form the unsaturated heterocycle followed by halogenation to introduce $L^2$ in 3-4.

Compound 3-5 can be obtained by metal-catalyzed coupling reactions of 3-4 with boronic acids or boronate esters (Suzuki reactions, where $R^2M$ is $R^2B(OH)_2$ or a boronic ester) or tin reagents (Stille reactions, where $R^2M$ is $R^2Sn(alkyl)_3$). The metal-catalyzed couplings, preferably Suzuki reactions, can be performed according to standard methodology as described in Scheme 1.

When $R^2$ in Formula I is cycloalkylamino (for example, piperidino), an alternative method to prepare compound 3-5 begins with starting material 2-4 as prepared in Scheme 2. The ester 2-4 ($R^a$ is $C_{(1-4)}$alkyl) can be hydrolyzed by an appropriate metal hydroxide reagent such as sodium hydroxide to give acid 2-4 ($R^a$ is H). The acid 2-4 can be converted to nitrile 3-6 according to the procedures as described for the conversion of 2-2 to 3-1. Compound 3-6 can be converted to compound 3-5 according to the methods as described for the conversion of 3-3 to 3-4.

The compounds of Formula I where $R^{10}$ is a nitrile ($R^{10}$ is CN) can be obtained from 3-6 by initial coupling with carboxylic acids $P^1$—WCOOH, followed by removal of the optional protecting group $P^1$ according to the procedures as described in Scheme 1 for the conversion of 1-2 to 1-6.

Similarly, the compounds of Formula I where $R^{10}$ is an unsaturated heterocycle can be obtained from 3-5 in two steps, namely coupling with a carboxylic acid $P^1$—WCOOH followed by removal of the optional protection group, as described in Scheme 1 for the conversion of 1-2 to 1-6.

It is understood that functional groups of compounds in this scheme can be further derivatized as outlined in Scheme 1.

Scheme 3a

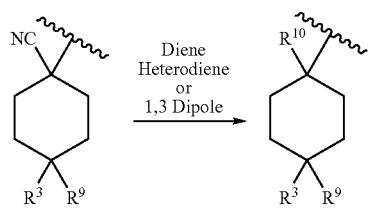

TABLE 1

| Number | Name | R¹⁰ Structure | Reference: |
|---|---|---|---|
| 1 | Imidazole | | U.S. patent application 2005101785 |
| 2 | Thiazole | | J. Med. Chem., 48(6), 2167-2175; (2005) |
| 3 | 4H-[1,2,4]Oxadiazol-5-one | | Bioorganic & Medicinal Chemistry, 13(6), 1989-2007 (2005) |
| 4 | 4H-Pyrrolo[2,3-b]pyrazine | | Journal of Medicinal Chemistry, 46(2), 222-236; (2003) |
| 5 | Pyridine | | Journal of Organic Chemistry, 67(13), 4414-4422; (2002) |
| 6 | [1,3,4]Oxadiazole | | Journal of Labelled Compounds and Radiopharmaceuticals, 16(5), 753-9; (1979) |
| 7 | 4H-[1,2,4]Triazole | | Bioorganic & Medicinal Chemistry Letters, 13(24), 4361-4364; (2003) |
| 8 | Tetrazole | | Eur. patent application., 648759 |
| 9 | Pyrazole | | Journal of Organic Chemistry, 54(3), 635-40; (1989) |

TABLE 1-continued
| Number | Name | R¹⁰ Structure | Reference: |
|---|---|---|---|
| 10 | [1,3,5]Triazine | | *Khimiko-Farmatsevticheskii Zhurnal*, 22(12), 1469-75; (1988) |
| 11 | [1,3,4]Thiadiazole | | *Ger. Offen.*, 102004009933 |
Scheme 4
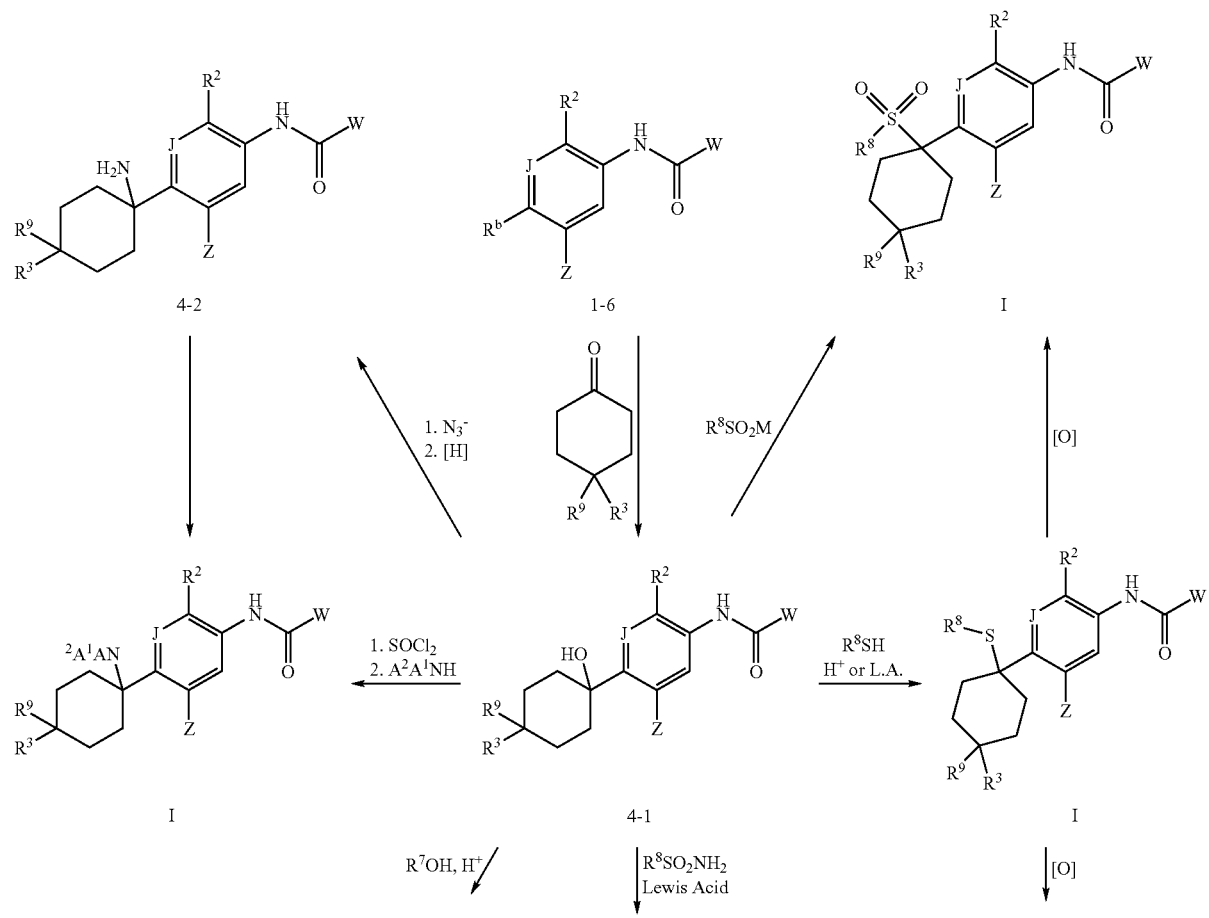

-continued

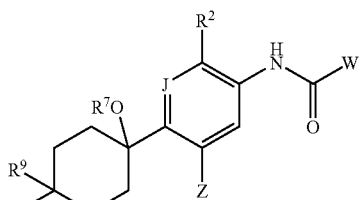 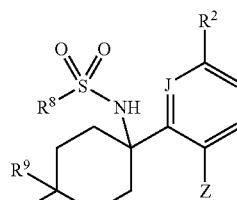 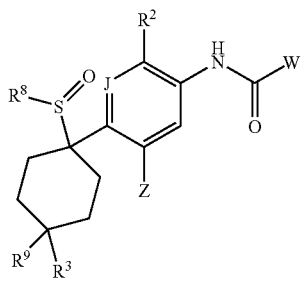

I  I  I

Scheme 4 describes the synthesis of compounds of Formula I where X is

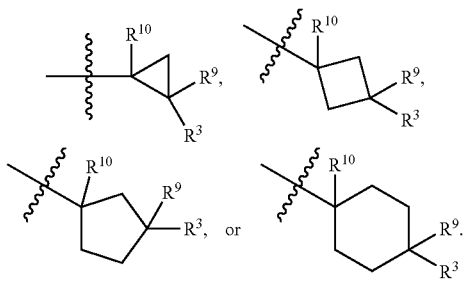

For the purpose of illustrating the methodology, reagents and conditions are defined in this scheme for the substrates where X is

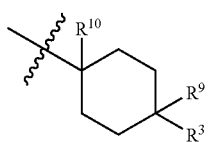

and where $R^z$, $R^3$ and $R^9$ are H; and J is CH. Those skilled in the art will recognize that the chemistry is applicable to all X, $R^z$, $R^3$, $R^9$ and J referenced above can be utilized with minor modifications to the reagents and conditions.

The starting material, compound 1-6 where $R^b$ is halogen, preferably Br, is obtained as described in Scheme 1. The halo compound 1-6 can be converted to alcohol 4-1 by initial deprotonation with a suitable base, such as isopropylmagnesium chloride (i-PrMgCl), followed by lithium-halogen exchange with an appropriate lithium reagent such as n-butyllithium or preferably tert-butyllithium, and then trapping of the organo-lithium intermediate with an appropriate ketone. Compounds 4-1 is both a compound of Formula I, and can serve as a useful intermediate for the synthesis of other compounds with different groups for $R^{10}$.

The tertiary hydroxyl group in compound 4-1 can also be converted to an amino group in compound I ($R^{10}$ is $NA^1A^2$) by activating 4-1 with a reagent such as thionyl chloride ($SOCl_2$) and trapping of the resulting intermediate(s) with a primary or secondary amine ($A^2A^1NH$).

Compounds of Formula I where $R^{10}$ is alkoxy ($OR^7$) can be obtained from the hydroxyl compound 4-1 by treatment with acidic reagents such as sulfuric acid or preferably trifluoroacetic acid (TFA) and then trapping of the resulting tertiary cation with an alcohol $R^7OH$ (where $R^7$ is $CH_2CH_2NA^1A^2$ or $CH_2CH_2OR^a$ where $A^1A^2$ or $R^a$ are not H).

The hydroxyl compound 4-1 can also be reacted with a sulfonamide $R^8SO_2NR^aH$ in the presence of a Lewis acid (L. A.) such as boron trifluoride diethyl etherate ($BF_3.OEt_2$) in a suitable solvent, such as THF to afford compound I ($R^{10}$ is $NHSO_2R^8$ where $R^8$ is $CH_2CH_2NA^1A^2$ or $R^a$ where $A^1$, $A^2$ or $R^a$ are not H).

Compounds of Formula I where $R^{10}$ is a sulfide ($R^{10}$ is $SR^8$) can be obtained from compound 4-1 by treatment with acidic reagents such as TFA or Lewis acids such as $BF_3.OEt_2$ and then trapping of the resulting tertiary cation with a thiol $R^8SH$ (where $R^8$ is $CH_2CH_2NA^1A^2$ or $R^a$).

Compounds of Formula I where $R^{10}$ is a sulfide ($R^{10}$ is $SR^8$) can be further oxidized to the corresponding sulfoxide (Formula I where $R^{10}$ is $SOR^8$) or sulfone (Formula I where $R^{10}$ is $SO_2R^8$) according to the sulfide oxidation procedures as described in Scheme 1.

Compounds of Formula I where $R^{10}$ is a sulfone can also be obtained directly from compound 4-1 by reaction with a metal sulfinate salt $R^8SO_2M$ (where M is Na, or K) (see, for example, B. Koutek, et al, *Synth. Commun.*, 6 (4), 305-8 (1976)).

It is understood that functional groups in this scheme can be further derivatized as outlined in Scheme 1. For example, the amino group in compound 4-2 can be reacted with various electrophiles. The amino group can be reacted with carboxylic acids according to standard procedures for amide bond formation or by reaction with acid chlorides or activated esters to form amide compounds as described in Scheme 1. It can be also reacted with an appropriate carbonylation agent, such as phosgene, carbonyldiimidazole or preferably triphosgene, in the presence of a base, such as pyridine or DIEA. The intermediate thus formed can be trapped with a primary or secondary amine, to afford the corresponding urea compound. Similarly, the amino group in compound 4-2 can be reacted with an appropriate oxalylation agent, such as oxalyl chloride, in the presence of a base, such as pyridine or DIEA and the intermediate thus formed can be trapped with a primary or secondary amine to afford oxalamide compounds. Furthermore, the amino group can be reacted with appropriate aldehydes or ketones in the presence of suitable reducing reagents such as $NaBH_4$ or $NaBH_3CN$, or preferably $NaBH(OAc)_3$ according to standard procedures for reductive amination as described in Scheme 1, to form compounds of Formula I where $R^{10}$ is $NA^1A^2$.

Scheme 5

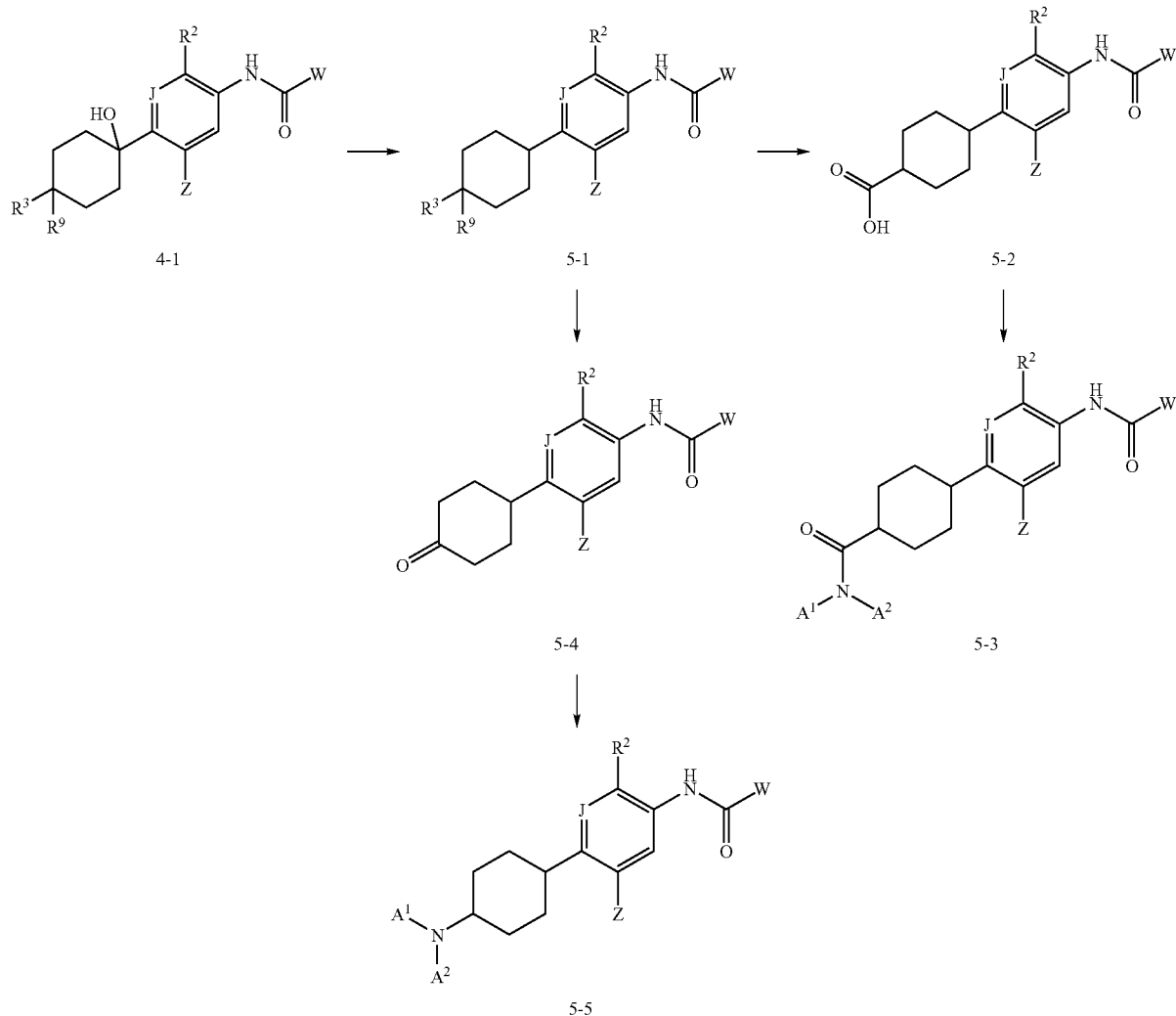

Scheme 5 describes the synthesis of compounds of Formula I where X is

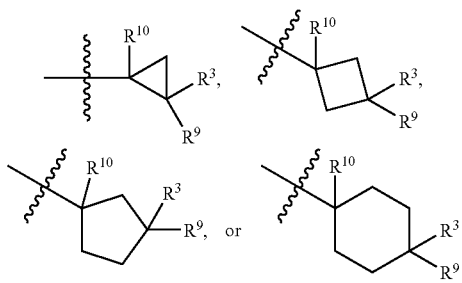

where $R^{10}$ is H or OH. For the purpose of illustrating the methodology, compounds where X comprises a cyclohexane ring are shown in Scheme 5, however those skilled in the art will recognize that the chemistry is applicable to all X shown above. Although reagents and conditions are defined for the substrate where J is CH, as previously mentioned in Scheme 1, it is understood that similar synthetic methods can be utilized with minor modifications when J is N.

Compounds of Formula 5-1 can be prepared from compounds of Formula 4-1 (prepared as described in Scheme 4). When $R^2$ contains an alkene, compounds of formula 4-1 can be deoxygenated using stannyl radicals (see, *J. Chem. Soc., Chem. Commun.*, 22, 1588-9, (1985) and *Prep. Carbohydrate Chem.*, 151, (1997)) or lithium perchlorate and triethylsilane (see, *Tetrahedron Lett.*, 35, 61-64, (1994). When $R^2$ does not contain an alkene, compounds of formula 4-1 can be deoxygenated in a two-step sequence, first by dehydration using an acid such as TFA to give the alkene, followed by reduction to the alkane using standard methodology such as catalytic hydrogenation (see references Scheme 1). Compounds of Formula 5-1 are also compounds of Formula I.

Compounds of Formula 5-2 are prepared from compounds of Formula 5-1 where $R^3$ is $CO_2R^a$ ($R^a$ is $C_{(1-4)}$alkyl), and $R^9$ is H by ester hydrolysis using preferably aqueous metal hydroxide solutions such as potassium hydroxide. The acids of Formula 5-2 may be converted into amides of Formula 5-3 by the methods described in Scheme 1. Compounds of formula 5-2 and 5-3 are also compounds of Formula I.

For compounds of Formula 5-1 where $R^3$ and $R^9$ together form a ketal, deprotection provides ketones of Formula 5-4 (see references in Wuts and Green, cited in Scheme 1). The ketones may then be reduced to alcohols of Formula I or reacted with amines in the presence of a reducing agent such as sodium triacetoxyborohydride (see *J. Org. Chem.*, 61, 3849-3862, (1996)) to give amines of Formula 5-5 which are also compounds of Formula I. Such amines of Formula I may then be further derivatized according to the methods described in Scheme 1.

Finally, the chemistry illustrated above for compounds of Formula 5-1, (ester hydrolysis followed by amide formation, and ketal deprotection to ketones and then conversion to alcohols and amines) also applies to compounds of Formula 4-1 to provide compounds of Formula I where $R^{10}$ is OH. For ketal deprotection in the presence of acid sensitive functionality, $LiBF_4$ in wet $CH_3CN$ may be used (see Lipshutz, B. and Harvey, D., *Synth. Commun.*, 12, 267 (1982)).

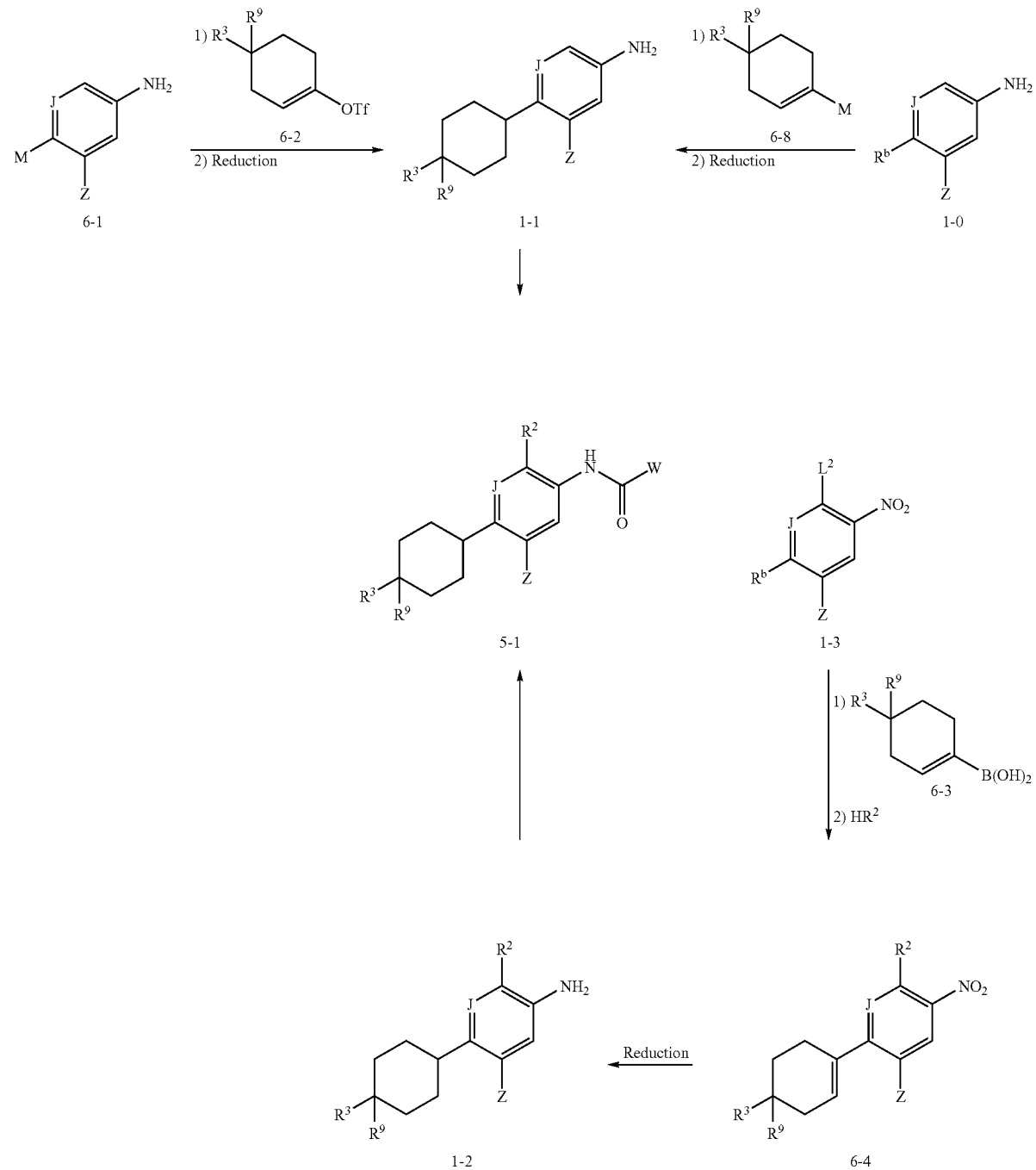

Scheme 6 illustrates an alternate route to compounds of Formula 5-1 where X is

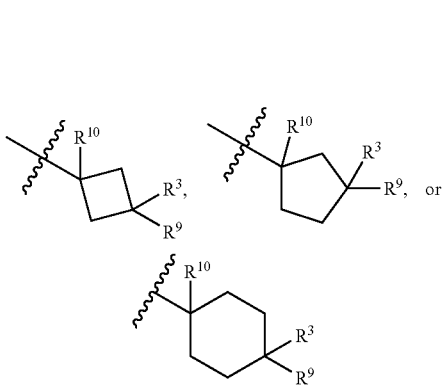

and $R^{10}$ is H that are used in Scheme 5 and are also compounds of Formula I. The methodology is illustrated for cyclohexane but those skilled in the art will recognize that the chemistry applies to all X shown above. Although reagents and conditions are defined for the substrate where J is CH, as previously mentioned in Scheme 1, it is understood that similar synthetic methods can be utilized with minor modifications when J is N.

Suzuki coupling of boronic acids (M is $B(OH)_2$)(or esters) of 6-1 with vinyl triflates of formula 6-2, followed by alkene reduction gives compounds of Formula 1-1. Alternatively, the sequence may be reversed and boronic acids (or esters) of formula 6-3 may be reacted with compounds of formula 1-0, where $R^b$ is a leaving group (preferably Br, I), followed by reduction to give 1-1. For preferred methodology for Suzuki reactions and reductions see Scheme 1. Vinyl triflates of formula 6-2 are readily available from ketones by enolate formation using an appropriate base such as LDA followed by reaction with N-phenyl bis-trifluoromethane sulfonamide (for reviews *Acc. Chem Res.*, 21, 47, (1998).

Compounds of Formula 1-0 are then converted to compounds of Formula 5-1 according to the methodology in Scheme 1 for the conversion of compounds of Formula 1-0 to compounds of Formula 1-6.

The synthesis of compounds of Formula 5-1 where $R^2$ is cycloalkylamino (for example, piperidino) starts with compounds of Formula 1-3 ($R^b$ is bromo or iodo). Suzuki coupling of compounds 1-3 with boronic acids (or esters) of formula 6-3, followed by displacement of $L^2$ (preferable fluoro or chloro) with $R^2H$ provides compounds of Formula 6-4 (see Scheme 1 for preferred methodology). Alternatively, this sequence may be reversed to also provide compounds of Formula 6-4 ($L^2$ displacement followed by Suzuki coupling). Reduction of both the nitro and alkene provides compounds of formula 1-2, which are then converted to compounds of Formula 5-1 as described for the conversion of compounds 1-2 to compounds of Formula 1-6 in Scheme 1.

Scheme 7

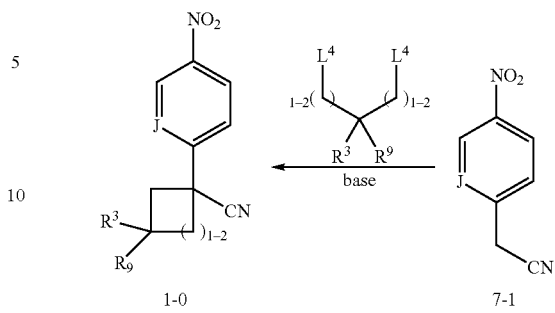

Scheme 7 describes the synthesis of useful intermediates of formula 1-0 where X is

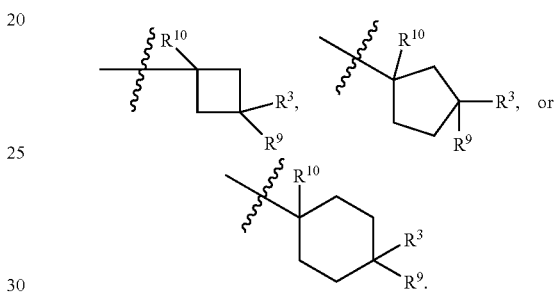

For the purpose of illustrating the methodology, X is

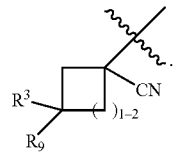

Those skilled in the art will recognize that the chemistry is applicable to all X, mentioned with only minor modifications to reagents and conditions. In addition, although reagents and conditions are defined for the substrates where J is CH, as previously mentioned in Scheme 1, it is also understood that similar synthetic methods can be utilized with minor modifications when J is N.

Commercially available starting material 7-1 can be reacted in a suitable solvent such as EtOH, THF, DME, or preferably DMF, with at least two equivalents of a suitable base such as potassium tert-butoxide, NaOEt, LDA, LHMDS or preferably NaH, and a reagent containing two leaving groups $L^4$ such as

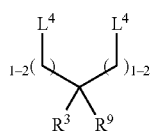

to obtain compound 1-0. These reagents with leaving groups are either commercially available or can be easily prepared. The suitable leaving groups $L^4$ are mesylates, tosylates, triflates and halogens such as Br, Cl, and I.

Scheme 8

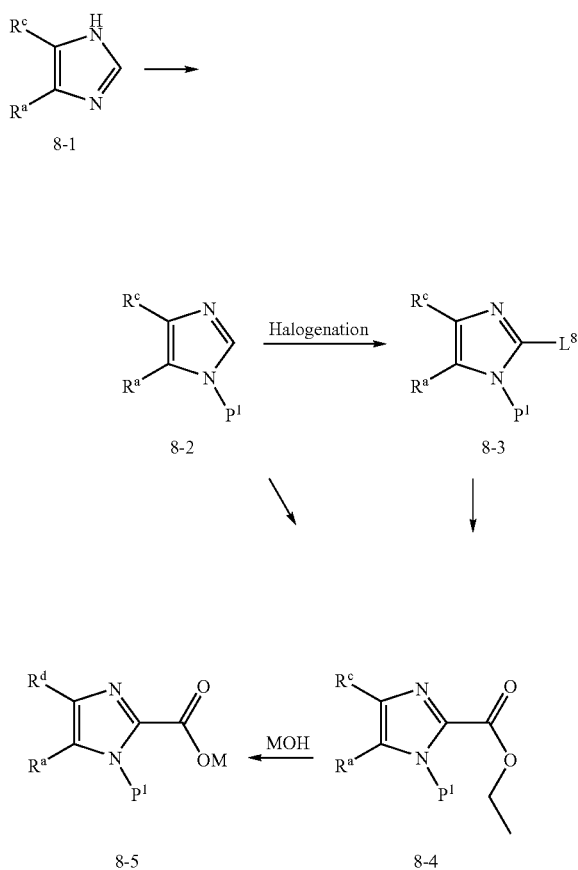

Scheme 8 illustrates a route to the preparation of 2-imidazolecarboxylates of Formula 8-5 where $R^a$ is H or $C_{(1-4)}$alkyl, and $R^d$ is H, alkyl, —CN, or —CONH$_2$ that are used as intermediates in the synthesis of compounds of Formula I where W is imidazole.

Imidazoles of Formula 8-1 where $R^a$ is H or $C_{(1-4)}$alkyl, and $R^c$ is H, $C_{(1-4)}$alkyl or —CN are either commercially available or, in the case where $R^c$ is —CN, are readily available from commercially available aldehydes (8-1 where $R^c$ is CHO) by reaction with hydroxylamines followed by dehydration with a suitable reagent such as phosphorus oxychloride or acetic anhydride (Synthesis, 677, 2003). Imidazoles of Formula 8-1 are protected with a suitable group ($P^1$) such as a methoxymethylamine (MOM), or preferably a SEM group to give compounds of Formula 8-2 (see Theodora W. Greene and Peter G. M. Wuts, Protective Groups in Organic Synthesis, John Wiley and Sons, Inc., NY (1991)).

Imidazoles of Formula 8-2, where $R^c$ is —CN, are halogenated with a suitable reagent such as N-bromosuccinimide or N-iodosuccinimide under either electrophilic conditions in a solvent such as DCM or CH$_3$CN or under radical conditions in the presence of an initiator such as azobis(isobutyronitrile) (AIBN) in a solvent such as CCl$_4$ to give compounds of Formula 8-3 where $L^8$ is a leaving group (preferably bromo or iodo). Halogen-magnesium exchange on compounds of Formula 8-3 provides the organomagnesium species, which is then reacted with a suitable electrophile to provide compounds of Formula 8-4. The preferred conditions for halogenmagnesium exchange are using an alkyl-magnesium reagent, preferably isopropylmagnesium chloride in a suitable solvent such as THF at temperatures between −78° C.-to 0° C. The preferred electrophiles are ethyl chloroformate or ethyl cyanoformate. For examples of halogen-magnesium exchange on cyanoimidazoles see J. Org. Chem. 65, 4618, (2000).

For imidazoles of Formula 8-2, where $R^c$ is not —CN, these may be converted directly to imidazoles of Formula 8-4 by deprotonation with a suitable base such as an alkyllithium followed by reaction with an electrophile as described above for the organomagnesium species. The preferred conditions are treating the imidazole with n-butyllithium in THF at −78° C. and quenching the resulting organolithium species with ethyl chloroformate (for examples, see Tetrahedron Lett., 29, 3411-3414, (1988)).

The esters of Formula 8-4 may then be hydrolyzed to carboxylic acids (M is H) or carboxylate salts (M is Li, Na, or K,) of Formula 8-5 using one equivalent of an aqueous metal hydroxide (MOH) solution, preferably potassium hydroxide in a suitable solvent such as ethanol or methanol. Synthesis of compounds of Formula 8-5 where $R^d$ is —CONH$_2$ is accomplished by first treating compounds of Formula 8-4 where $R^c$ is —CN with an appropriate alkoxide such as potassium ethoxide to convert the cyano group to an imidate group (Pinner reaction) followed by hydrolysis of both the ester and imidate groups with two equivalents of an aqueous metal hydroxide solution.

Scheme 9

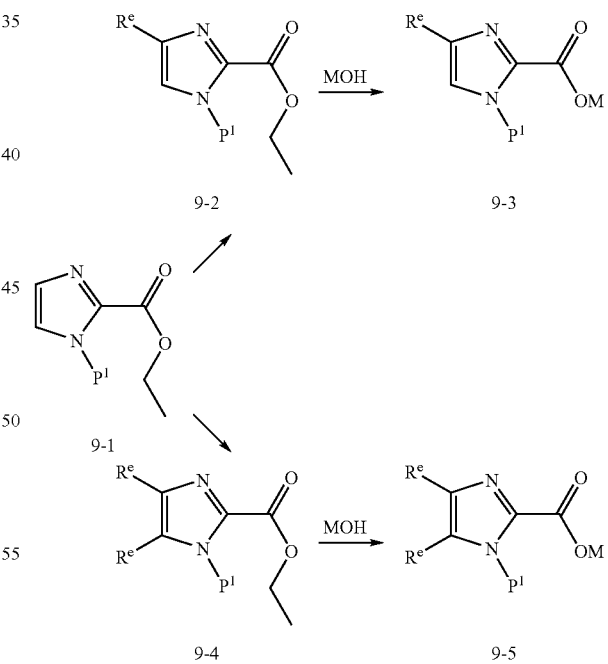

Scheme 9 illustrates a route to 2-imidazolecarboxylates of Formula 9-3 or 9-5 where $R^e$ is chloro or bromo, and M is H, Li, K, or Na that are used as intermediates in the synthesis of compounds of Formula I where W is imidazole.

Compounds of Formula 9-1 are first prepared by protection of commercially available ethyl imidazolecarboxylate according to the methods outlined in Scheme 8, preferably with a SEM group.

Compounds of Formula 9-2 are prepared by reaction of compounds of Formula 9-1 with one equivalent of an appropriate halogenating reagent, such as NBS or NCS in a suitable solvent such as $CH_3CN$, DCM or DMF at 25° C. Compounds of Formula 9-4 are prepared by reaction of compounds of Formula 9-1 with two equivalents of an appropriate halogenating reagent, such as NBS or NCS in a suitable solvent such as $CH_3CN$ or DMF at temperatures between 30° C. to 80° C. Imidazoles of Formula 9-3 and 9-5 are then obtained from the respective esters by hydrolysis as described in Scheme 8.

Scheme 10

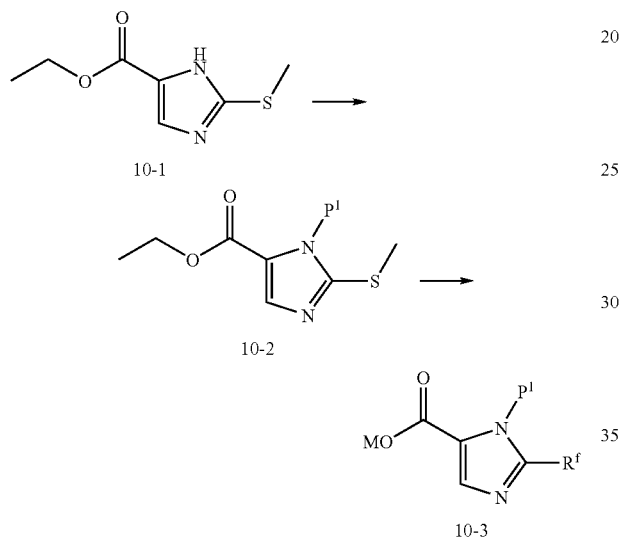

Scheme 10 illustrates a method for the preparation of imidazoles of Formula 10-3 where $R^f$ is —$SCH_3$, —$SOCH_3$, or —$SO_2CH_3$, M is H, Li, K, or Na that are used as intermediates in the synthesis of compounds of Formula I where W is imidazole.

Imidazole 10-1 (WO 1996011932) is protected according to the methods described in Scheme 8, preferably with a SEM protecting group to give compounds of Formula 10-2. Ester hydrolysis according to the procedure in Scheme 8 gives compounds of Formula 10-3 where $R^f$ is —$SCH_3$. Oxidation of 2-methylthioimidazoles of Formula 10-2 with one equivalent of an appropriate oxidant, followed by ester hydrolysis according to the procedure in Scheme 8 gives compounds of Formula 10-3 where $R^f$ is —$SOCH_3$. Oxidation with two equivalents of an appropriate oxidant, followed by ester hydrolysis according to the procedure in Scheme 8 gives compounds of Formula 10-3 where $R^f$ is —$SO_2CH_3$. The preferred reagent for oxidation is MCPBA in DCM. References for the conversion of sulfides to sulfoxides and sulfones are given in Scheme 1.

The following examples are for exemplary purposes only and are in no way meant to limit the invention.

EXAMPLE 1

4-Cyano-1H-imidazole-2-carboxylic acid [2-(4,4-dimethyl-cyclohex-1-enyl)-4-(1-hydroxy-cyclohexyl)-phenyl]-amide

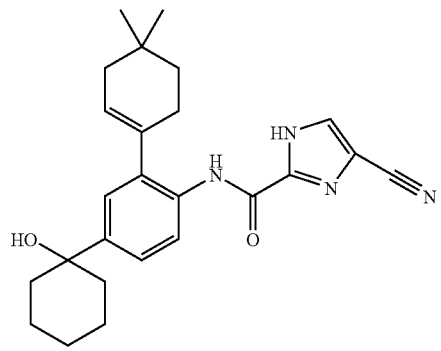 [SMILES: CC1(C)CC=C(c2cc(C3(O)CCCCC3)ccc2NC(=O)c2nc(C#N)c[nH]2)CC1]

a) 1-(2-Trimethylsilanyl-ethoxymethyl)-1H-imidazole-4-carbonitrile

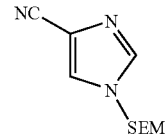

A flask charged with imidazole-4-carbonitrile (0.50 g, 5.2 mmol) (*Synthesis*, 677, 2003), 2-(trimethylsilyl)ethoxymethyl chloride (SEMCl) (0.95 mL, 5.3 mmol), $K_2CO_3$ (1.40 g, 10.4 mmol), and acetone (5 mL) was stirred for 10 h at RT. The mixture was diluted with EtOAc (20 mL), washed with water (20 mL), brine (20 mL) and the organic layer was dried over $MgSO_4$. The crude product was eluted from a 20-g SPE cartridge (silica) with 30% EtOAc/hexane to give 0.80 g (70%) of the title compound as a colorless oil. Mass spectrum (CI ($CH_4$), m/z): Calcd. for $C_{10}H_{17}N_3OSi$, 224.1 (M+H), found 224.1.

b) 2-Bromo-1-(2-trimethylsilanyl-ethoxymethyl)-1H-imidazole-4-carbonitrile

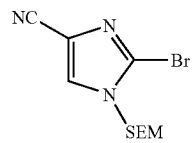

To a solution of 1-(2-trimethylsilanyl-ethoxymethyl)-1H-imidazole-4-carbonitrile (0.70 g, 3.1 mmol) (as prepared in the previous step) in $CCl_4$ (10 mL) was added N-bromosuccinimide (NBS) (0.61 g, 3.4 mmol) and azobis(isobutyronitrile) (AIBN) (cat), and the mixture was heated at 60° C. for 4 h. The reaction was diluted with EtOAc (30 mL), washed with NaHCO$_3$ (2×30 mL), brine (30 mL), the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI (CH$_4$), m/z): Calcd. for C$_{10}$H$_{16}$BrN$_3$OSi, 302.0/304.0 (M+H), found 302.1/304.1.

c) 4-Cyano-1-(2-trimethylsilanyl-ethoxymethyl)-1H-imidazole-2-carboxylic acid ethyl ester

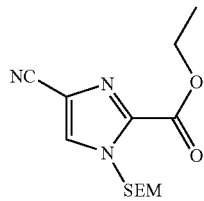

To a solution of 2-bromo-1-(2-trimethylsilanyl-ethoxymethyl)-1H-imidazole-4-carbonitrile (0.55 g, 1.8 mmol) (as prepared in the previous step) in tetrahydrofuran (THF) (6 mL) at −40° C. was added dropwise a solution of 2 M i-PrMgCl in THF (1 mL). The reaction was allowed to stir for 10 min at −40° C. and then cooled to −78° C., and ethyl cyanoformate (0.30 g, 3.0 mmol) was added. The reaction was allowed to attain RT and stirred for 1 h. The reaction was quenched with satd aq NH$_4$Cl, diluted with EtOAc (20 mL), washed with brine (2×20 mL). The organic layer was dried over Na$_2$SO$_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for C$_{13}$H$_{21}$N$_3$O$_3$Si, 296.1 (M+H), found 296.1.

d) 4-Cyano-1-(2-trimethylsilanyl-ethoxymethyl)-1H-imidazole-2-carboxylate potassium salt

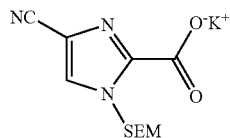

To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.2 mL, 1.2 mmol) and the reaction was stirred for 10 min and then concentrated to give 0.40 g (100%) of the title compound as a yellow solid. $^1$H-NMR (CD$_3$OD; 400 MHz): δ 7.98 (s, 1H), 5.92 (s, 2H), 3.62 (m, 2H), 0.94 (m, 2H), 0.00 (s, 9H). Mass spectrum (ESI-neg, m/z): Calcd. for C$_{11}$H$_{16}$KN$_3$O$_3$Si, 266.1 (M−K), found 266.0.

e) 4-Bromo-2-(4,4-dimethyl-cyclohex-1-enyl)-phenylamine

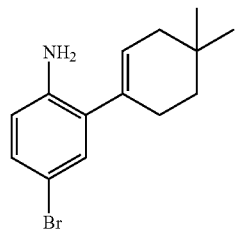 [SMILES: CC1(C)CC=C(c2cc(Br)ccc2N)CC1]

A flask is charged with 4-bromo-2-iodo-phenylamine (1.10 g, 3.70 mmol), 4,4-dimethylcyclohexen-1-ylboronic acid (0.630 g, 4.07 mmol), Pd(PPh$_3$)$_4$ (0.24 g, 5 mol %), 2 M Na$_2$CO$_3$ (16 mL), EtOH (16 mL) and toluene (32 mL) and heated at 80° C. for 6 h. The reaction was diluted with EtOAc (100 mL) and washed with saturated aqueous NaHCO$_3$ (2×100 mL) and brine (100 mL), and the organic layer dried over Na$_2$SO$_4$ and evaporated. The crude product was purified by flash silica gel chromatography eluting with 10% EtOAc/hexanes to give 0.680 g (66%) of the title compound as a light yellow oil. Mass spectrum (ESI, m/z): Calcd. for C$_{14}$H$_{18}$BrN, 280.1 (M+H), found 280.1.

f) 4-Cyano-1-(2-trimethylsilanyl-ethoxymethyl)-1H-imidazole-2-carboxylic acid [4-bromo-2-(4,4-dimethyl-cyclohex-1-enyl)-phenyl]-amide

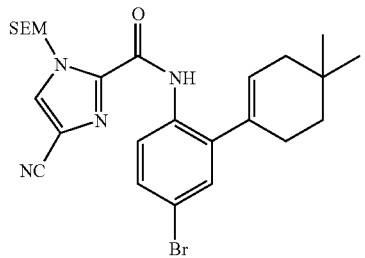

To a suspension of 4-bromo-2-(4,4-dimethyl-cyclohex-1-enyl)-phenylamine (0.640 g, 2.29 mmol) (prepared in the previous step) and 4-cyano-1-(2-trimethylsilanyl-ethoxymethyl)-1H-imidazole-2-carboxylate potassium salt (0.700 g, 2.30 mmol) (prepared in this example, step (d)) in DCM (12 mL) was added DIPEA (0.800 mL, 4.60 mmol) and PyBroP (1.29 g, 2.76 mmol) and the mixture allowed to stir at RT for 10 h. The mixture was diluted with DCM (50 mL) and washed with NaHCO$_3$ (2×50 mL) and the organic layer dried over Na$_2$SO$_4$ and concentrated. The title compound was eluted from a 20-g SPE with 1:1 DCM/hexanes to give 1.04 g (86%) of the title compound as a white solid. Mass spectrum (ESI, m/z): Calcd. for C$_{25}$H$_{33}$BrN$_4$O$_2$Si, 529.1 (M+H), found 529.1.

g) 4-Cyano-1H-imidazole-2-carboxylic acid [4-bromo-2-(4,4-dimethyl-cyclohex-1-enyl)-phenyl]-amide

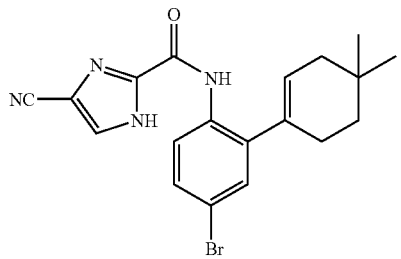

To a solution of 4-cyano-1-(2-trimethylsilanyl-ethoxymethyl)-1H-imidazole-2-carboxylic acid [4-bromo-2-(4,4-dimethyl-cyclohex-1-enyl)-phenyl]-amide (0.95 g, 1.80 mmol) (prepared in the previous step) in 10 mL of DCM was added 0.4 mL of EtOH and 10 mL of TFA and the mixture stirred for 1 h at RT. The mixture was concentrated and triturated with $Et_2O$ to give 0.68 g (95%) of a white solid: $^1$H-NMR (400 MHz, $CDCl_3$): δ 11.23 (br s, 1H), 9.52 (br s, 1H), 8.27 (d, J=8.7 Hz, 1H), 7.72 (s, 1H), 7.41 (dd, J=2.3, 8.7 Hz, 1H), 7.33 (d, J=2.3 Hz, 1H), 5.82 (m, 1H), 2.28 (m, 2H), 2.10 (m, 2H), 1.58 (m, 2H), 1.08 (s, 6H). Mass spectrum (ESI, m/z): Calcd. for $C_{19}H_{19}BrN_4O$, 399.1 (M+H), found 399.0.

h) 4-Cyano-1H-imidazole-2-carboxylic acid [2-(4,4-dimethyl-cyclohex-1-enyl)-4-(1-hydroxy-cyclohexyl)-phenyl]-amide A solution of 4-cyano-1H-imidazole-2-carboxylic acid [4-bromo-2-(4,4-dimethyl-cyclohex-1-enyl)-phenyl]-amide (159 mg, 0.397 mmol, as prepared in Example 1, step (g)) in THF (15 mL) was placed under Ar, cooled to −78° C., and treated with i-PrMgCl (199 μL, 0.397 mmol). The mixture was warmed to RT, allowed to stir at that temperature for 10 min, cooled to −78° C., treated with t-BuLi (701 μL, 1.19 mmol), stirred at that temperature for 10 min, and then treated with cyclohexanone (411 μL, 3.97 mmol). The mixture was warmed to RT, stirred 1.5 h, quenched with satd aq $NH_4Cl$ (20 mL), and extracted with EtOAc (2×50 mL). The combined organic layers were dried over $MgSO_4$ and concentrated in vacuo. Silica gel chromatography of the residue with 25-50% EtOAc-hexane on a 20-g Isolute SPE column afforded 75.0 mg (45%) of the title compound as a white solid. $^1$H-NMR ($CD_3OD$; 400 MHz): δ 12.11-11.91 (br s, 1H), 9.63 (s, 1H), 8.31 (d, 1H, J=8.4 Hz), 7.71 (s, 1H), 7.43 (dd, 1H, J=8.4, 2.0 Hz), 7.36 (d, 1H, J=2.0 Hz), 5.82-5.75 (m, 1H), 3.77-3.67 (m, 1H), 2.62-2.53 (m, 1H), 2.42-2.24 (m, 4H), 2.17-2.07 (m, 2H), 1.96-1.55 (m, 10H), 1.10 (s, 6H). Mass spectrum (ESI, m/z): Calcd. for $C_{25}H_{30}NO_2$, 419.2 (M+H), found 419.1.

EXAMPLE 2

4-[4-[(5-Cyano-1H-imidazole-2-carbonyl)-amino]-3-(4,4-dimethyl-cyclohex-1-enyl)-phenyl]-cis-4-hydroxy-cyclohexanecarboxylic acid

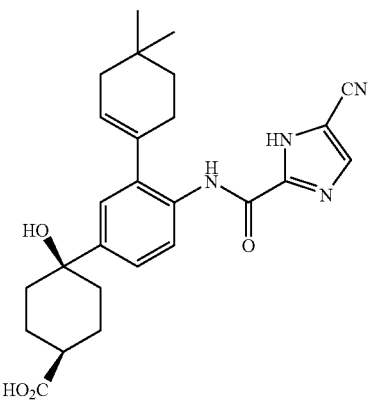 [SMILES: CC1(C)CC=C(c2cc([C@]3(O)CC[C@@H](C(=O)O)CC3)ccc2NC(=O)c2ncc(C#N)[nH]2)CC1]

a) 4-[4-[(4-Cyano-1H-imidazole-2-carbonyl)-amino]-3-(4,4-dimethyl-cyclohex-1-enyl)-phenyl]-cis-4-hydroxy-cyclohexanecarboxylic acid ethyl ester

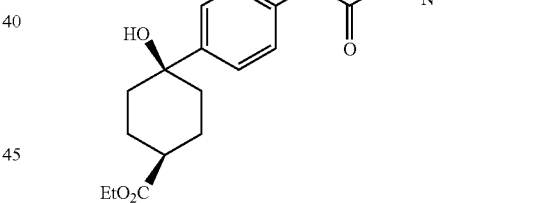

To a suspension of 4-cyano-1H-imidazole-2-carboxylic acid [4-bromo-2-(4,4-dimethyl-cyclohex-1-enyl)-phenyl]-amide (65 mg, 0.16 mmol) (prepared in Example 1, step (g)) in 5 mL THF at −40° C. was added i-PrMgCl (0.20 mL, 0.40 mmol, 2 M in THF) and the solution was then warmed to 0° C. and stirred for 10 min. The solution was then cooled to −78° C. and t-BuLi (0.25 mL, 0.42 mmol, 1.7 M in pentane) was added dropwise over 2 min and then 4-oxo-cyclohexanecarboxylic acid ethyl ester (0.13 mL, 0.80 mmol) was added immediately thereafter. After 5 min at −78° C. the reaction was quenched with satd $NH_4Cl$ (10 mL) and extracted with EtOAc (3×10 mL) and dried over $Na_2SO_4$. The title compound was used in the next step without further purification.

b) 4-[4-[(4-Cyano-1H-imidazole-2-carbonyl)-amino]-3-(4,4-dimethyl-cyclohex-1-enyl)-phenyl]-cis-4-hydroxy-cyclohexanecarboxylic acid To a solution of 4-[4-[(4-cyano-1H-imidazole-2-carbonyl)-amino]-3-(4,4-dimethyl-cyclohex-1-enyl)-phenyl]-cis- 4-hydroxy-cyclohexanecarboxylic acid ethyl ester (50 mg, 0.10 mmol)(prepared in the previous step) in 1 mL of EtOH was added 2N KOH (0.16 mL, 0.32 mmol) and the reaction stirred at RT for 2 h. The mixture was diluted with 5 mL of H$_2$O, the pH adjusted to 2 with 2M TFA/H$_2$O, and the title compound was purified by RP-HPLC on a C18 column eluting with a linear gradient of 30-50% CH$_3$CN in 0.1% TFA/H$_2$O over 10 min to give 14 mg (19%, steps (a) and (b)) of a white solid. $^1$H-NMR (400 MHz, CD$_3$OD): δ 8.13 (d, J=8.6 Hz, 1H), 7.98 (s, 1H), 7.39 (dd, J=8.6, 2.2 Hz, 1H), 7.34 (d, J=2.2 Hz, 1H), 5.72 (m, 1H), 2.39 (m, 1H), 2.34-2.27 (m, 2H), 2.09-1.77 (m, 10H), 1.58 (t, J=6.2 Hz, 1H), 1.07 (s, 6H). Mass spectrum (ESI, m/z): Calcd. for C$_{26}$H$_{30}$N$_4$O$_4$, 461.2 (M−H), found 461.3.

EXAMPLE 3

4-Cyano-1H-imidazole-2-carboxylic acid [2-(4,4-dimethyl-cyclohex-1-enyl)-4-(1-hydroxy-cyclopentyl)-phenyl]-amide

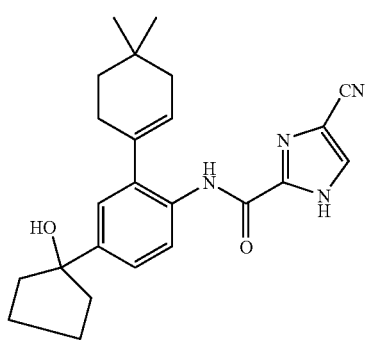 [SMILES: CC1(C)CC=C(c2cc(C3(O)CCCC3)ccc2NC(=O)c2nc(C#N)c[nH]2)CC1]

The title compound was prepared as described in Example 1, step (h) using 4-cyano-1H-imidazole-2-carboxylic acid [4-bromo-2-(4,4-dimethyl-cyclohex-1-enyl)-phenyl]-amide (as prepared in Example 1 step (g)) and cyclopentanone. Mass spectrum (ESI, m/z): Calcd. for C$_{24}$H$_{28}$N$_4$O$_2$, 405.2 (M+H), found 405.1.

EXAMPLE 4

4-Cyano-1H-imidazole-2-carboxylic acid [4-(1-cyano-cyclopropyl)-2-(4,4-dimethyl-cyclohex-1-enyl)-phenyl]-amide

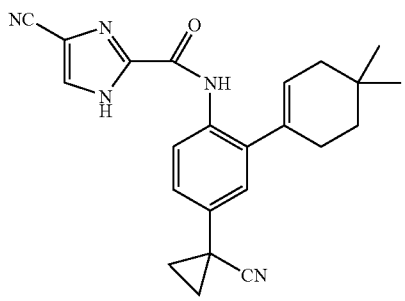

a) 1-(4-Amino-phenyl)-cyclopropanecarbonitrile

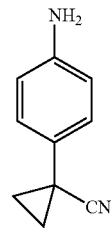

To a solution of 1-(4-nitro-phenyl)-cyclopropanecarbonitrile (500 mg, 2.65 mmol, *Journal of the American Chemical Society,* 71, 2031-5; 1949) in 7 mL of EtOH-2.5 mL of EtOAc was added 350 mg 5% Pd—C. The mixture was stirred under 1 atm of H$_2$ overnight. The reaction was filtered, concentrated in vacuo and then purified using preparative thin layer chromatography (CHCl$_3$) to afford the title compound as an oil (96 mg, 23%). Mass spectrum (ESI, m/z): Cald. C$_{10}$H$_{10}$N$_2$, 159.0, found 159.2.

b) 1-[4-Amino-3-(4,4-dimethyl-cyclohex-1-enyl)-phenyl]-cyclopropanecarbonitrile

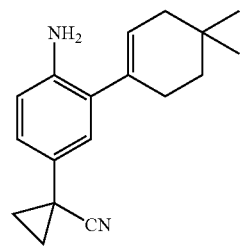 [SMILES: CC1(C)CC=C(c2cc(C3(C#N)CC3)ccc2N)CC1]

To a solution of 1-(4-amino-phenyl)-cyclopropanecarbonitrile (96 mg, 0.60 mmol) in MeCN (3 mL) at 0° C. was added NBS (108 mg, 0.60 mmol) and the reaction was allowed to stir overnight. The reaction was diluted with EtOAc (25 mL) and was then washed with saturated aqueous NaHCO$_3$ (1×25 mL). The organic layer was dried (Na$_2$SO$_4$) and concentrated in vacuo to give 114 mg (80%) of 1-(4-amino-3-bromo-phenyl)-cyclopropanecarbonitrile. The crude product was used without further purification.

The title compound was prepared from 1-(4-amino-3-bromo-phenyl)-cyclopropanecarbonitrile (as prepared in this step) and 4,4-dimethylcyclohexen-1-yl boronic acid using the conditions described in Example 1, step (e). $^1$H NMR (CD$_3$OD; 400 MHz): δ 6.95 (dd, 1H, J=8.2, 2.3 Hz), 6.88 (d, 1H, J=2.3 Hz,), 6.71 (d, 1H, J=8.2 Hz), 5.62 (m, 1H), 2.52-2.23 (m, 2H), 1.98-1.97 (m, 2H), 1.55-1.51 (m, 4H), 1.31-1.28 (m, 2H), 1.01 (s, 6H).

c) 4-Cyano-1-(2-trimethylsilanyl-ethoxymethyl)-1H-imidazole-2-carboxylic acid [4-(1-cyano-cyclopropyl)-2-(4,4-dimethyl-cyclohex-1-enyl)-phenyl]-amide

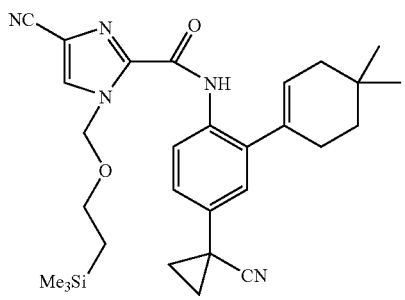

The title compound was prepared from 1-[4-amino-3-(4,4-dimethyl-cyclohex-1-enyl)-phenyl]-cyclopropanecarbonitrile (as prepared in the previous step) using the conditions described in Example 1, step (f). $^1$H NMR (CDCl$_3$; 400 MHz): δ 9.74 (s, 1H), 8.36 (d, 1H, J=9.3 Hz), 7.15 (m, 1H), 5.93 (s, 2H), 5.76 (m, 1H), 3.67-3.63 (m, 2H), 2.27-2.25 (m, 2H), 2.10-2.09 (m, 2H), 1.72-1.69 (m, 2H), 1.59 (t, 1H, J=6.28 Hz), 1.41-1.38 (m, 2H), 1.11 (s, 6H), 0.99-0.94 (m, 2H), 0.00 (s, 9H).

d) 4-Cyano-1H-imidazole-2-carboxylic acid [4-(1-cyano-cyclopropyl)-2-(4,4-dimethyl-cyclohex-1-enyl)-phenyl]-amide The title compound was prepared from 4-cyano-1-(2-trimethylsilanyl-ethoxymethyl)-1H-imidazole-2-carboxylic acid [4-(1-cyano-cyclopropyl)-2-(4,4-dimethyl-cyclohex-1-enyl)-phenyl]-amide (as prepared in the previous step) using the conditions described in Example 1, step (g). $^1$H NMR (CD$_3$OD; 400 MHz): δ 8.24 (d, 1H, J=8.4 Hz), 7.99 (s, 1H), 7.24-7.22 (m, 1H), 7.17 (s, 1H), 5.76 (s, 1H), 2.30 (br s, 2H), 2.08 (br s, 2H), 1.69 (br s, 2H), 1.60 (t, 2H, J=6.01 Hz), 1.47 (br s, 2H), 1.00 (s, 6H). Mass spectrum (ESI, m/z): Calcd. for C$_{23}$H$_{23}$N$_5$O, 386.1 (M+H), found 386.1.

The following examples are produced according to procedures of previous examples with the corresponding reagents as indicated in the table below:

| Example No. | Name | Structure | Procedure Reference | Reagents |
| --- | --- | --- | --- | --- |
| 5 | 4-Cyano-1H-imidazole-2-carboxylic acid [2-(4,4-dimethyl-cyclohex-1-enyl)-4-(1-morpholin-4-yl-cyclopentyl)-phenyl]-amide | 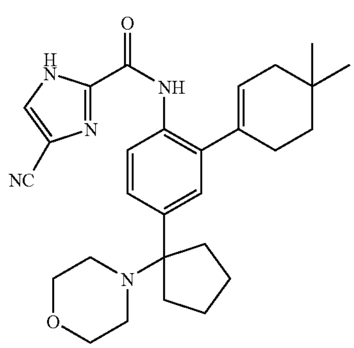 | Ex 1, step (h), Ex. 43. | Cyclopentanone; morpholine |
| 6 | 4-Cyano-1H-pyrrole-2-carboxylic acid [2-(4,4-dimethyl-cyclohex-1-enyl)-4-(1-morpholin-4-yl-cyclopentyl)-phenyl]-amide | 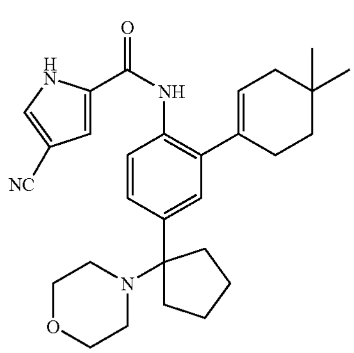 | Ex 1, steps (e), (f), (h) Ex 43. | Cyclopentanone; Morpholine (Canadian J. Chem. 59, 2673 (1981)) |

-continued

| Example No. | Name | Structure | Procedure Reference | Reagents |
|---|---|---|---|---|
| 7 | 4-Cyano-1H-imidazole-2-carboxylic acid[4-[1-(2-dimethylamino-ethoxy)-cyclobutyl]-2-(4-methyl-piperidin-1-yl)-phenyl]-amide | 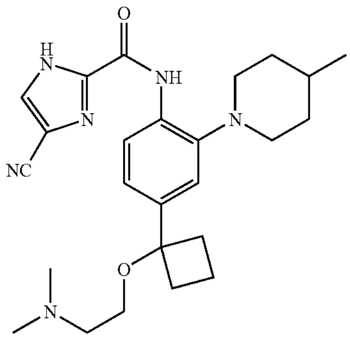 | Ex 1, steps (f)-(h), Ex. 36 | (WO 2005131022, A1) cyclobutanone; 2-dimethylamino-ethanol |
| 8 | 4-Cyano-1H-pyrrole-2-carboxylic acid[4-[1-(2-dimethylamino-ethoxy)-cyclobutyl]-2-(4-methyl-piperidin-1-yl)-phenyl]-amide | 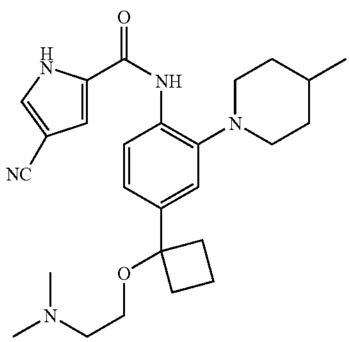 | Ex 1 step (f), (h), Ex. 36. | (WO 2005131022, A1) cyclobutanone; 2-dimethylamino-ethanol |
| 9 | 4-Cyano-1H-imidazole-2-carboxylic acid{2-(4,4-dimethyl-cyclohex-1-enyl)-4-[1-(2-imidazol-1-yl-ethoxy)-cyclohexyl]-phenyl}-amide | 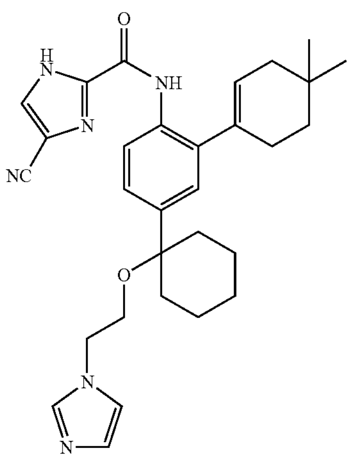 | Ex. 1, step (h); Ex 36 | Cyclohexanone; 1-(2-hydroxy-ethyl)imidazole |
| 10 | 4-Cyano-1H-imidazole-2-carboxylic acid{4-[1-(4-ethyl-piperazin-1-yl)-cyclopentyl]-2-spiro[4.5]dec-7-en-8-yl-phenyl}-amide | 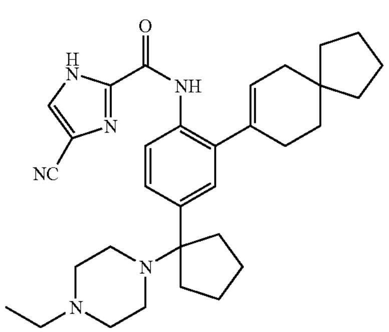 | Ex. 1, steps (e)-(h); Ex 43. | (WO 2005063705); cyclopentanone, 1-ethyl-piperazine |

-continued

| Example No. | Name | Structure | Procedure Reference | Reagents |
|---|---|---|---|---|
| 11 | 4-Cyano-1H-imidazole-2-carboxylic acid[4-(1-dimethylamino-cyclobutyl)-2-spiro[4.5]dec-7-en-8-yl-phenyl]-amide | 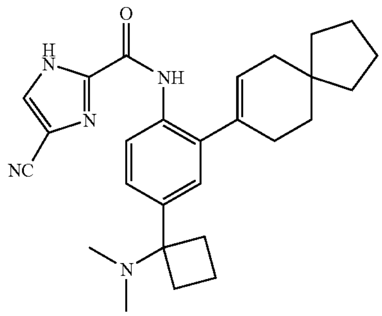 | Ex. 1, steps (e)-(h); Ex 43 | (WO 2005063705); cyclobutanone, dimethylamine |
| 12 | 4-Cyano-1H-imidazole-2-carboxylic acid{4-[1-(2-dimethyl-amino-ethoxy)-cyclopentyl]-2-spiro[4.5]dec-7-en-8-yl-phenyl}-amide | 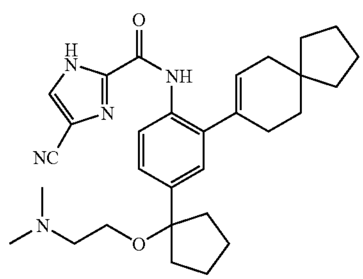 | Ex. 1, steps (e)-(h); Ex 36 | (WO 2005063705); cyclopentanone, 2-dimethyl-aminoethanol |
| 13 | 4-Cyano-1H-pyrrole-2-carboxylic acid{2-(4,4-dimethyl-cyclohex-1-enyl)-4-[1-(4-methyl-piperazin-1-yl)-cyclobutyl]-phenyl}-amide | 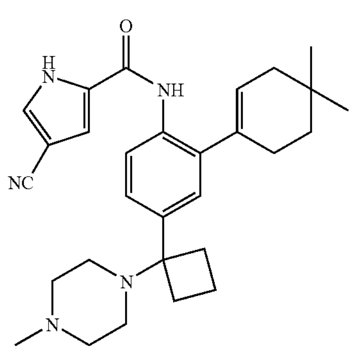 | Ex 1 steps (e), (f), (h), Ex. 43 | Cyclobutanone; 1-methyl-piperazine |

EXAMPLE 14

4-Cyano-1H-imidazole-2-carboxylic acid [4-(1-cyano-cyclohexyl)-2-(4,4-dimethyl-cyclohex-1-enyl)-phenyl]-amide

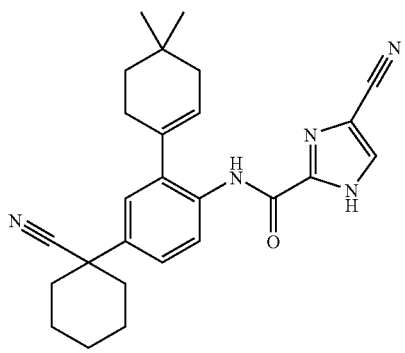 [SMILES: CC1(C)CC=C(c2cc(C3(C#N)CCCCC3)ccc2NC(=O)c2nc(C#N)c[nH]2)CC1]

a) 1-(4-Nitro-phenyl)-cyclohexanecarbonitrile

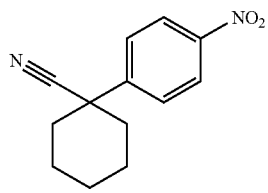 [SMILES: N#CC1(c2ccc([N+](=O)[O-])cc2)CCCCC1]

A slurry of NaH (711 mg, 29.6 mmol) in DMSO (10 mL) and THF (3 mL) was treated portionwise slowly with (4-nitro-phenyl)-acetonitrile (2.00 g, 12.3 mmol) and stirred at RT for 5 min until $H_2$ evolution ceased. A solution of dibromopentane (2.02 mL, 14.8 mmol) in THF (10 mL) was added to the slurry over 10 min. The mixture was stirred at RT for an additional 5 min, placed in an oil bath at RT, slowly warmed to 70° C., and stirred at 70° C. for 1 h. The cooled mixture was diluted with EtOAc (250 mL) and washed with water (3×100 mL) and brine (2×100 mL). The combined aqueous layers were extracted with EtOAc (1×100 mL). The combined organic layers were dried over $MgSO_4$ and concentrated in vacuo. Silica gel chromatography of the residue on a 50-g Varian MegaBond Elut SPE column with 10% EtOAc-hexane afforded the title compound (1.46 g, 51%) as a tan solid. $^1$H-NMR ($CDCl_3$; 400 MHz): δ 8.26 (d, 2H, J=8.4 Hz), 7.69 (d, 2H, J=8.4 Hz), 2.21-2.13 (m, 2H), 1.98-1.74 (m, 8H).

b) 1-(4-Amino-phenyl)-cyclohexane carbonitrile

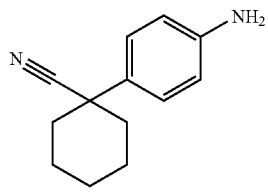 [SMILES: N#CC1(c2ccc(N)cc2)CCCCC1]

A solution of 1-(4-nitro-phenyl)-cyclohexanecarbonitrile (0.500 g, 2.17 mmol, as prepared in the previous step) in EtOH (6 mL) and water (6 mL) was treated with $NH_4Cl$ (1.16 g, 21.7 mmol) and Fe powder (606 mg, 10.9 mmol) and heated to 50° C. for 2 h. The cooled mixture was filtered through Celite, and the filter cake was washed with MeOH. The solvents were evaporated in vacuo. The residue was partitioned between water (50 mL) and EtOAc (75 mL), and the layers were separated. The organic layer was dried over $MgSO_4$ and concentrated in vacuo to afford the title compound (488 mg, 100%) as an orange oil. The compound was used in the following step without purification. Mass spectrum (ESI, m/z): Calcd. for $C_{13}H_{16}N_2$, 201.1 (M+H), found 201.3.

c) 1-(4-Amino-3-bromo-phenyl)-cyclohexane carbonitrile

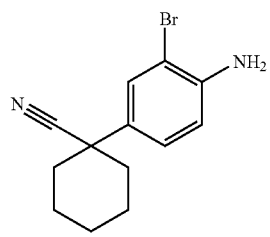 [SMILES: N#CC1(c2ccc(N)c(Br)c2)CCCCC1]

The title compound was prepared from 1-(4-amino-phenyl)-cyclohexane carbonitrile (as prepared in the previous step) by bromination with NBS according to the procedure in Example 4, step (b), replacing $CH_3CN$ with $CH_2Cl_2$. $^1$H-NMR ($CDCl_3$; 400 MHz): δ 7.49 (d, 1H, J=2.0 Hz), 7.23 (dd, 1H, J=8.4, 2.0 Hz), 6.76 (d, 1H, J=8.4 Hz), 2.16-2.08 (m, 2H), 1.90-1.73 (m, 8H).

d) 1-[4-Amino-3-(4,4-dimethyl-cyclohex-1-enyl)-phenyl]-cyclohexanecarbonitrile

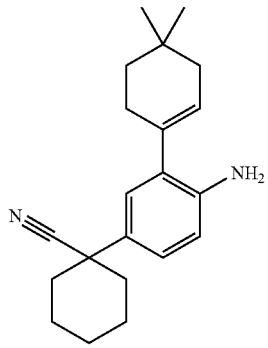 [SMILES: CC1(C)CC=C(c2cc(C3(C#N)CCCCC3)ccc2N)CC1]

A solution of 1-(4-amino-3-bromo-phenyl)-cyclohexane carbonitrile (136 mg, 0.487 mmol, as prepared in the previous step) in DMF (10 mL) was treated with 4,4-dimethyl-cyclohex-1-enylboronic acid (90.0 mg, 0.585 mmol) and $Na_2CO_3$ (1.95 mL, 3.90 mmol, 2 M aq). The mixture was degassed via sonication, placed under Ar, treated with Pd(dppf)$Cl_2$ (35.6 mg, 0.0487 mmol), and heated to 80° C. overnight. The cooled mixture was partitioned between EtOAc (50 mL) and water (50 mL). The aqueous layer was extracted with EtOAc (2×50 mL). The combined organic layers was dried over $MgSO_4$ and concentrated in vacuo. Silica gel chromatography of the residue on a 20-g Isolute SPE column with 10-15% EtOAc-hexane afforded the title compound (45.9 mg, 30%) as a colorless glassy solid. Mass spectrum (ESI, m/z): Calcd. for $C_{21}H_{28}N_2$, 309.2 (M+H), found 309.2.

e) 4-Cyano-1-(2-trimethylsilanyl-ethoxymethyl)-1H-imidazole-2-carboxylic acid [4-(1-cyano-cyclohexyl)-2-(4,4-dimethyl-cyclohex-1-enyl)-phenyl]-amide

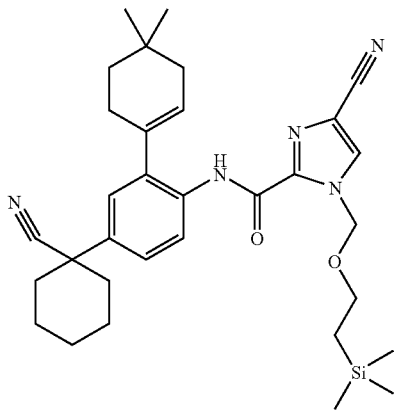 [SMILES: CC1(C)CC=C(c2cc(C3(C#N)CCCCC3)ccc2NC(=O)c2nc(C#N)cn2COCC[Si](C)(C)C)CC1]

The title compound was prepared from 1-[4-amino-3-(4,4-dimethyl-cyclohex-1-enyl)-phenyl]-cyclohexanecarbonitrile (as prepared in the previous step) and 4-cyano-1-(2-trimethylsilanyl-ethoxymethyl)-1H-imidazole-2-carboxylate potassium salt (as prepared in Example 1, step (d)) according to the procedure of Example 1, step (f). Mass spectrum (ESI, m/z): Calcd. for $C_{32}H_{43}N_5O_2Si$, 558.3 (M+H), found 557.8.

f) 4-Cyano-1H-imidazole-2-carboxylic acid [4-(1-cyano-cyclohexyl)-2-(4,4-dimethyl-cyclohex-1-enyl)-phenyl]-amide A solution of 4-cyano-1-(2-trimethylsilanyl-ethoxymethyl)-1H-imidazole-2-carboxylic acid [4-(1-cyano-cyclohexyl)-2-(4,4-dimethyl-cyclohex-1-enyl)-phenyl]-amide (66.0 mg, 0.118 mmol, as prepared in the previous step) in $CH_2Cl_2$ (6 mL) was treated with EtOH (3 drops) and TFA (0.8 mL) at RT for 2 h. Solvents were evaporated in vacuo. Purification of the residue by RP-HPLC (C18) with 20-80% $CH_3CN$ in 0.1% $TFA/H_2O$ over 25 min afforded the title compound (25.7 mg, 43%) as a white solid. $^1$H-NMR ($CD_3OD$; 400 MHz): δ 8.20 (d, 1H, J=8.8 Hz), 7.93 (s, 1H), 7.37 (dd, 1H, J=8.8, 2.0 Hz), 7.26 (d, 1H, J=2.0 Hz), 5.73-5.67 (m, 1H), 2.29-2.21 (m, 2H), 2.08-1.98 (m, 4H), 1.88-1.68 (m, 6H), 1.58-1.50 (m, 2H), 1.02 (s, 6H). Mass spectrum (ESI, m/z): Calcd. for $C_{26}H_{29}N_5O$, 428.2 (M+H), found 428.2.

EXAMPLE 15

1-[4-[(4-Cyano-1H-imidazole-2-carbonyl)-amino]-3-(4,4-dimethyl-cyclohex-1-enyl)-phenyl]-cyclopentanecarboxylic acid

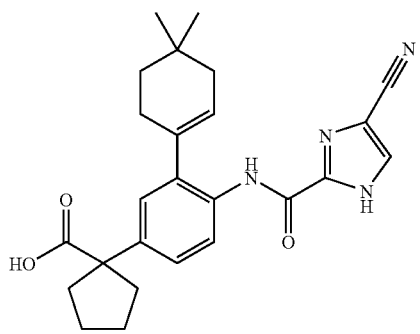 [SMILES: CC1(C)CC=C(c2cc(C3(C(=O)O)CCCC3)ccc2NC(=O)c2nc(C#N)c[nH]2)CC1]

a) 1-(4-Nitro-phenyl)-cyclopentanecarbonitrile

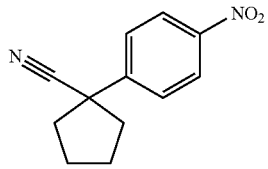 [SMILES: N#CC1(c2ccc([N+](=O)[O-])cc2)CCCC1]

The title compound is prepared from 4-(nitro-phenyl)-acetonitrile and 1,4-dibromo-butane according to the procedure in Example 14, step (a).

b) 1-(4-Nitro-phenyl)-cyclopentanecarboxylic acid

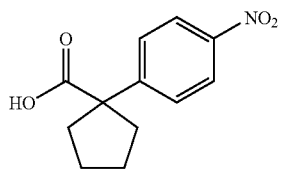 [SMILES: O=C(O)C1(c2ccc([N+](=O)[O-])cc2)CCCC1]

A solution of 1-(4-nitro-phenyl)-cyclopentanecarbonitrile (as prepared in the previous step) conc $H_2SO_4$ is heated at 100° C. for 2 h. The mixture is poured into water and extracted with EtOAc. The organic layer is dried ($MgSO_4$) and concentrated in vacuo. The residue is purified by silica gel chromatography with the appropriate solvent to afford the title compound.

c) 1-(4-Nitro-phenyl)-cyclopentanecarboxylic acid tert-butyl ester

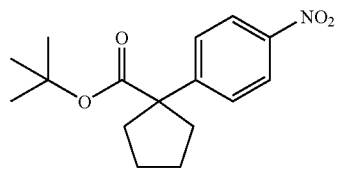 [SMILES: CC(C)(C)OC(=O)C1(c2ccc([N+](=O)[O-])cc2)CCCC1]

A solution of 1-(4-nitro-phenyl)-cyclopentanecarboxylic acid (as prepared in the previous step) in THF at −78° C. in a pressure bottle is treated with 2 drops of concentrated sulfuric acid, and isobutylene gas is condensed into the mixture. The mixture is stirred 24 h at RT, cooled to −78° C. and quenched with satd aq $NaHCO_3$. The mixture is warmed to RT and extracted with EtOAc. The organic layer is dried ($MgSO_4$) and concentrated in vacuo. The residue is purified by silica gel chromatography with an appropriate solvent to afford the title compound.

d) 1-[4-[(4-Cyano-1H-imidazole-2-carbonyl)-amino]-3-(4,4-dimethyl-cyclohex-1-enyl)-phenyl]-cyclopentanecarboxylic acid The title compound is prepared from 1-(4-nitro-phenyl)-cyclopentanecarboxylic acid tert-butyl ester (as prepared in the previous step) according to the procedures in Example 4 step (a) and Example 1, steps (e)-(g).

The following examples are produced according to procedures of previous examples with the corresponding reagents as indicated in the table below:

| Example No. | Name | Structure | Procedure Reference | Reagents |
|---|---|---|---|---|
| 16 | 4-Cyano-1H-imidazole-2-carboxylic acid[2-cyclohex-1-enyl-4-(cis-4-hydroxy-1-isocyano-cyclohexyl)-phenyl]amide | 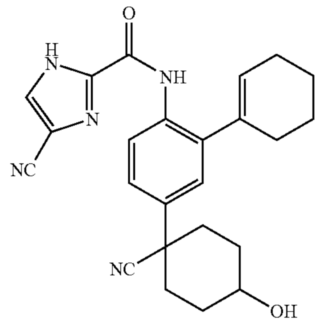 | Ex. 14, step (a); Example 4, steps (a), (b) and Ex. 1, steps (e)-(g) | |
| 17 | 4-Cyano-4-[4-[(4-cyano-1H-imidazole-2-carbonyl)-amino]-3-(4,4-dimethyl-cyclohex-1-enyl)-phenyl]-cyclohexane carboxylic acid methyl ester | 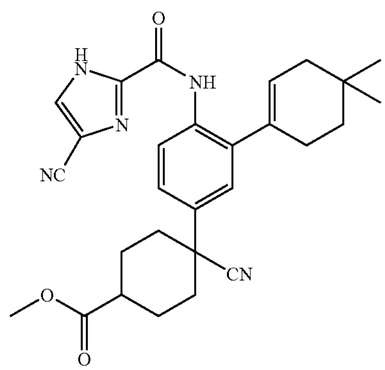 | Ex. 14, step (a); Example 4, steps (a), (b) and Example 1, steps (e)-(g) | |

EXAMPLE 18

4-[4-[(5-Cyano-1H-imidazole-2-carbonyl)-amino]-3-(4,4-dimethyl-cyclohex-1-enyl)-phenyl]-cyclohexanecarboxylic acid

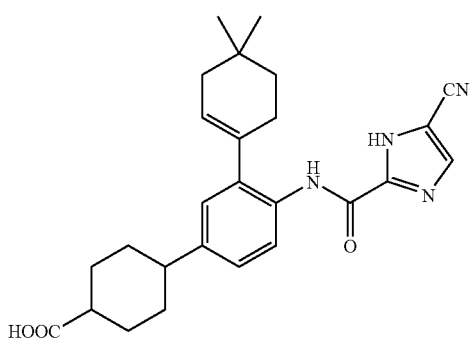 [SMILES: CC1(C)CC=C(c2cc(C3CCC(C(=O)O)CC3)ccc2NC(=O)c2ncc(C#N)[nH]2)CC1]

a) 4-[4-[(4-Cyano-1H-imidazole-2-carbonyl)-amino]-3-(4,4-dimethyl-cyclohex-1-enyl)-phenyl]-cyclohexanecarboxylic acid methyl ester

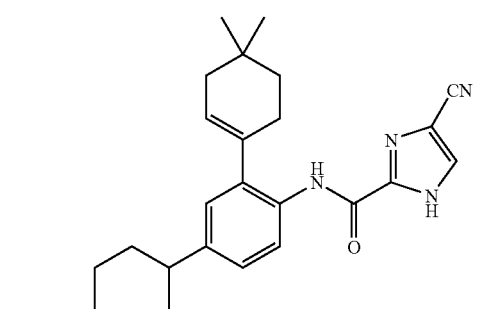

The title compound is prepared by deoxygenation of 4-[4-[(4-cyano-1H-imidazole-2-carbonyl)-amino]-3-(4,4-dimethyl-cyclohex-1-enyl)-phenyl]-cis-4-hydroxy-cyclohexanecarboxylic acid methyl ester (as prepared from 4-oxo-cyclohexanecarboxylic acid methyl ester using the procedure in Example 2, step (a)) according to the procedure of Dolan, S., et al, *J. Chem., Soc., Chem. Commun.*, 1588-9 (1985).

b) 5-Cyano-1H-imidazole-2-carboxylic acid [2-(4,4-dimethyl-cyclohex-1-enyl)-4-(2-morpholin-4-yl-ethyl)-phenyl]-amide hydrochloride The title compound is prepared from 4-[4-{[4-cyano-1-(2-trimethylsilanyl-ethoxymethyl)-1H-imidazole-2-carbonyl]-amino}-3-(4,4-dimethyl-cyclohex-1-enyl)-phenyl]-cyclohexanecarboxylic acid methyl ester (as prepared in the previous step) according to the procedure in Example 2, step (b).

EXAMPLE 19

5-Cyano-1H-imidazole-2-carboxylic acid [2-(4,4-dimethyl-cyclohex-1-enyl)-4-(1-hydroxy-4,4-dimethoxy-cyclohexyl)-phenyl]-amide

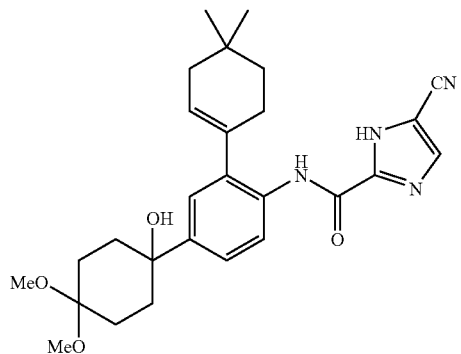 [SMILES: COC1(OC)CCC(O)(c2ccc(NC(=O)c3ncc(C#N)[nH]3)c(C3=CCC(C)(C)CC3)c2)CC1]

The title compound is prepared from 4,4-dimethoxycyclohexanone (*Tetrahedron Lett.*, 1107-8 (1975) and ibid, 31, 3237-40 (1990)) using the procedure of Example 1, step (h).

EXAMPLE 20

5-Cyano-1H-imidazole-2-carboxylic acid [4-(4,4-dimethoxy-cyclohexyl)-2-(4,4-dimethyl-cyclohex-1-enyl)-phenyl]-amide

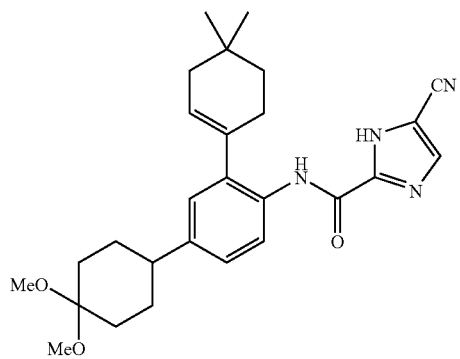 [SMILES: COC1(OC)CCC(c2ccc(NC(=O)c3ncc(C#N)[nH]3)c(C3=CCC(C)(C)CC3)c2)CC1]

The title compound is prepared from 5-cyano-1H-imidazole-2-carboxylic acid [2-(4,4-dimethyl-cyclohex-1-enyl)-4-(1-hydroxy-4,4-dimethoxy-cyclohexyl)-phenyl]-amide (as prepared in Example 19) using the procedure of Example 18 step (a).

EXAMPLE 21

5-Cyano-1H-imidazole-2-carboxylic acid [2-(4,4-dimethyl-cyclohex-1-enyl)-4-(1-hydroxy-4-oxo-cyclohexyl)-phenyl]-amide

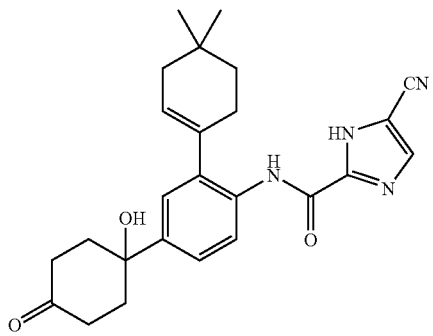 [SMILES: CC1(C)CC=C(c2cc(C3(O)CCC(=O)CC3)ccc2NC(=O)c2ncc(C#N)[nH]2)CC1]

The title compound is prepared from 5-cyano-1H-imidazole-2-carboxylic acid [2-(4,4-dimethyl-cyclohex-1-enyl)-4-(1-hydroxy-4,4-dimethoxy-cyclohexyl)-phenyl]-amide (as prepared in Example 19) by treatment with LiBF$_4$ in wet CH$_3$CN using the procedure of Lipshutz, B. and Harvey, D., *Synth. Commun.*, 12, 267 (1982).

EXAMPLE 22

5-Cyano-1H-imidazole-2-carboxylic acid [4-(4-dimethylamino-1-hydroxy-cyclohexyl)-2-(4,4-dimethyl-cyclohex-1-enyl)-phenyl]-amide

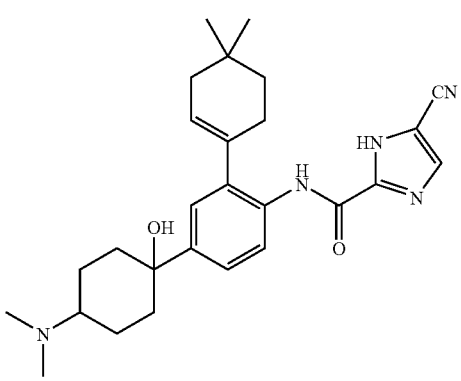 [SMILES: CN(C)C1CCC(O)(c2ccc(NC(=O)c3ncc(C#N)[nH]3)c(C3=CCC(C)(C)CC3)c2)CC1]

The title compound is prepared from 5-cyano-1H-imidazole-2-carboxylic acid [2-(4,4-dimethyl-cyclohex-1-enyl)-4-(1-hydroxy-4-oxo-cyclohexyl)-phenyl]-amide (as prepared in Example 21) and dimethylamine (solution in THF) using NaBH(OAc)$_3$ according to literature procedure (*J. Org. Chem.*, 61, 3849-62 (1996)).

EXAMPLE 23

5-Cyano-1H-imidazole-2-carboxylic acid [2-(4,4-dimethyl-cyclohex-1-enyl)-4-(4-oxo-cyclohexyl)-phenyl]-amide

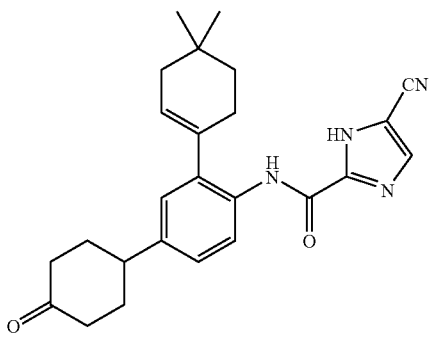 [SMILES: CC1(C)CC=C(c2cc(C3CCC(=O)CC3)ccc2NC(=O)c2ncc(C#N)[nH]2)CC1]

a) 4-(4-Nitro-phenyl)-cyclohexanone

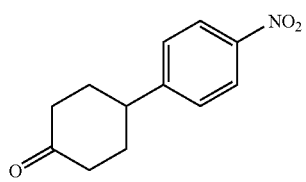 [SMILES: O=C1CCC(c2ccc([N+](=O)[O-])cc2)CC1]

Concentrated H$_2$SO$_4$ (20 mL) was cooled to 0° C. and treated with 4-phenyl-cyclohexanone (4.22 g, 24.2 mmol), and fuming nitric acid (1.6 mL) was added very carefully dropwise, keeping the temperature of the mixture below 20° C. After the addition of nitric acid was complete, the mixture was warmed to RT and allowed to stir for 5 h. The mixture was poured over ice (200 mL) and extracted with EtOAc (3×150 mL). The combined organic layers were dried over MgSO$_4$ and concentrated in vacuo. Silica gel chromatography with 10% EtOAc-hexane on a 70-g Isolute SPE column (FlashMaster system) afforded the title compound (0.512 g, 10%) as a pale yellow solid. $^1$H-NMR (CD$_3$OD; 400 MHz): δ 8.20 (d, 2H, J=8.8 Hz), 7.42 (d, 2H, J=8.8 Hz), 3.16 (tt, 1H, J=12.0, 4.0 Hz), 2.58-2.51 (m, 4H), 2.31-2.21 (m, 2H), 2.05-1.91 (m, 2H).

b) 4-(4-Amino-phenyl)-cyclohexanone

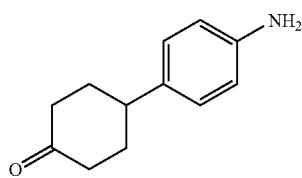 [SMILES: Nc1ccc(C2CCC(=O)CC2)cc1]

A solution of 4-(4-nitro-phenyl)-cyclohexanone (0.512 g, 2.34 mmol, as prepared in the previous step) in EtOH (50 mL) was hydrogenated under the following conditions on an H-cube apparatus fitted with a 30 mm CatCart™ 5% Pd/C cartridge: 40° C., 40 bar H$_2$, flow rate 1 mL/min. The solvent was evaporated in vacuo. Silica gel chromatography of the residue with 25% EtOAc-hexane on a 20-g Isolute SPE column (FlashMaster system) afforded the title compound (0.140 g, 32%) as a colorless glassy solid. Mass spectrum (ESI, m/z): Calcd. for C$_{12}$H$_{15}$NO, 190.1 (M+H), found 190.2.

c) 4-(4-Amino-3-bromo-phenyl)-cyclohexanone

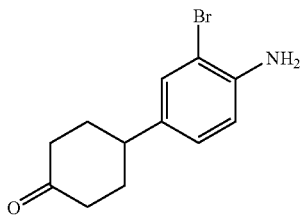 [SMILES: Nc1ccc(C2CCC(=O)CC2)cc1Br]

The title compound was prepared from 4-(4-amino-phenyl)-cyclohexanone (as prepared in the previous step) by bromination with NBS according to the procedure in Example 4, step (b), replacing CH$_3$CN with CH$_2$Cl$_2$. Mass spectrum (ESI, m/z): Calcd. for C$_{12}$H$_{14}$NOBr, 268.0/270.0 (M+H), found 268.3/270.2.

d) 4-[4-Amino-3-(4,4-dimethyl-cyclohex-1-enyl)-phenyl]-cyclohexanone

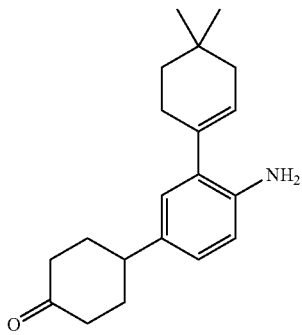 [SMILES: CC1(C)CC=C(c2cc(C3CCC(=O)CC3)ccc2N)CC1]

The title compound was prepared from 4-(4-amino-3-bromo-phenyl)-cyclohexanone (as prepared in the previous step) according to the procedure in Example 1, step (e). Mass spectrum (ESI, m/z): Calcd. for C$_{20}$H$_{27}$NO, 298.2 (M+H), found 298.2.

e) 4-Cyano-1-(2-trimethylsilanyl-ethoxymethyl)-1H-imidazole-2-carboxylic acid [2-(4,4-dimethyl-cyclohex-1-enyl)-4-(4-oxo-cyclohexyl)-phenyl]-amide

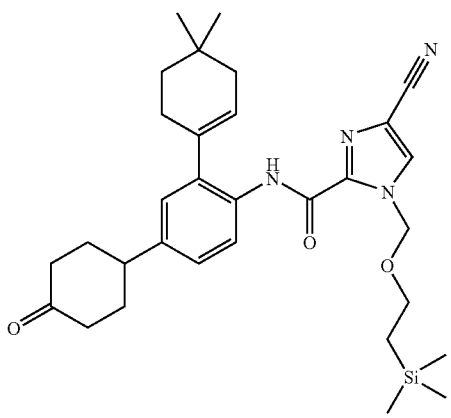 [SMILES: CC1(C)CC=C(c2cc(C3CCC(=O)CC3)ccc2NC(=O)c2nc(C#N)cn2COCC[Si](C)(C)C)CC1]

The title compound was prepared from 4-[4-amino-3-(4,4-dimethyl-cyclohex-1-enyl)-phenyl]-cyclohexanone (as prepared in the previous step) and 4-cyano-1-(2-trimethylsilanyl-ethoxymethyl)-1H-imidazole-2-carboxylate potassium salt (as prepared in Example 1, step (d)) according to the procedure in Example 1, step (f). Mass spectrum (APCI, m/z): Calcd. for $C_{31}H_{42}N_4O_3Si$, 547.3 (M+H), found 547.0.

f) 4-Cyano-1H-imidazole-2-carboxylic acid [2-(4,4-dimethyl-cyclohex-1-enyl)-4-(4-oxo-cyclohexyl)-phenyl]-amide The title compound was prepared from 4-cyano-1-(2-trimethylsilanyl-ethoxymethyl)-1H-imidazole-2-carboxylic acid [2-(4,4-dimethyl-cyclohex-1-enyl)-4-(4-oxo-cyclohexyl)-phenyl]-amide (as prepared in the previous step) according to the procedure in Example 1, step (g). $^1$H-NMR (CDCl$_3$; 400 MHz): δ 9.59 (s, 1H), 8.31 (d, 1H, J=8.4 Hz), 7.72 (s, 1H), 7.20 (dd, 1H, J=8.4, 2.0 Hz), 7.08 (d, 1H, J=2.0 Hz), 5.81-5.75 (m, 1H), 3.04 (tt, 1H, J=11.6 Hz, 4.0 Hz), 2.56-2.48 (m, 4H), 2.33-2.19 (m, 4H), 2.14-2.08 (m, 2H), 2.04-1.91 (2H), 1.62-1.55 (m, 2H), 1.11 (s, 6H). Mass spectrum (APCI, m/z): Calcd. for $C_{31}H_{42}N_4O_3$, 417.2 (M+H), found 417.2.

EXAMPLE 24

4-Cyano-1H-imidazole-2-carboxylic acid [4-(4-diethylamino-cyclohexyl)-2-(4,4-dimethyl-cyclohex-1-enyl)-phenyl]-amide

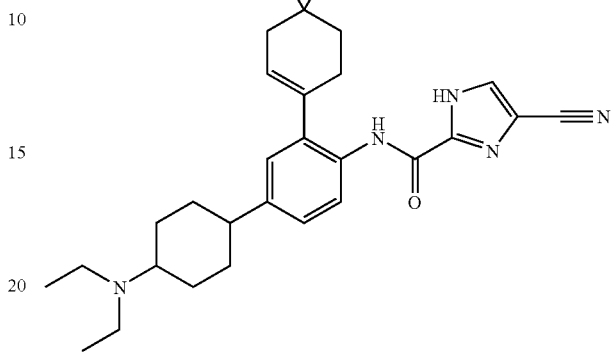

The title compound is prepared from 4-cyano-1H-imidazole-2-carboxylic acid [2-(4,4-dimethyl-cyclohex-1-enyl)-4-(4-oxo-cyclohexyl)-phenyl]-amide (as prepared in Example 23) and diethylamine using NaBH(OAc)$_3$ according to literature procedure (*J. Org. Chem.*, 61, 3849-62 (1996)).

The following examples are produced according to procedures of previous examples with the corresponding reagents as indicated in the table below:

| Example No. | Name | Structure | Procedure Reference | Reagents |
|---|---|---|---|---|
| 25 | 4-Cyano-1H-imidazole-2-carboxylic acid[2-(4,4-dimethyl-cyclohex-1-enyl)-4-(3-hydroxy-bicyclo[3.2.1]oct-3-yl)-phenyl]-amide | (structure shown) | Example 1, step (h) | (structure shown) *Organic Syntheses*, 51 60-5 (1971) |
| 26 | 4-Cyano-1H-imidazole-2-carboxylic acid(2-(4,4-dimethyl-cyclohex-1-enyl)-4-{1-hydroxy-4-[(2-methoxy-ethyl)-methyl-amino]-cyclohexyl}-phenyl)-amide | (structure shown) | Example 22 | (structure shown) |

| Example No. | Name | Structure | Procedure Reference | Reagents |
|---|---|---|---|---|
| 27 | 4-Cyano-1H-imidazole-2-carboxylic acid[2-(4,4-dimethyl-cyclohex-1-enyl)-4-(4-morpholin-4-yl-cyclohexyl)-phenyl]-amide | 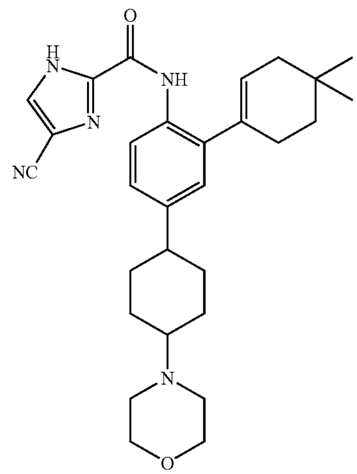 | Example 24 | |
| 28 | 4-Cyano-1H-imidazole-2-carboxylic acid{2-(4,4-dimethyl-cyclohex-1-enyl)-4-[4-(4-methyl-piperazin-1-yl)-cyclohexyl]-phenyl}-amide | 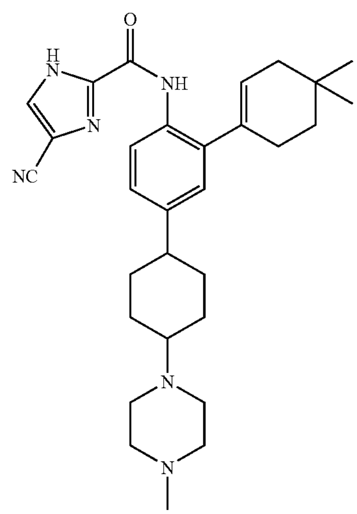 | Example 24 | |
| 29 | 4-Cyano-1H-imidazole-2-carboxylic acid{2-(4,4-dimethyl-cyclohex-1-enyl)-4-[4-(4-ethyl-piperazin-1-yl)-cyclohexyl]-phenyl}-amide | 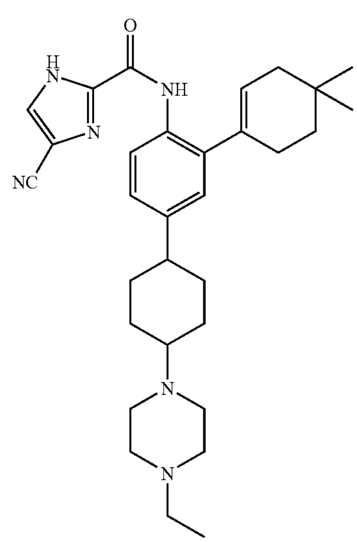 | Example 24 | |

-continued

| Example No. | Name | Structure | Procedure Reference | Reagents |
|---|---|---|---|---|
| 30 | 4-Cyano-1H-imidazole-2-carboxylic acid(2-(4,4-dimethyl-cyclohex-1-enyl)-4-{4-[(2-methoxy-ethyl)-methyl-amino]-cyclohexyl}-phenyl)-amide | 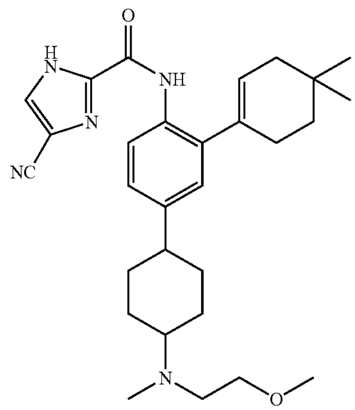 | Example 24 | (Fluorochem, Inc.) |
| 31 | 4-Cyano-1H-imidazole-2-carboxylic acid{2-(4,4-dimethyl-cyclohex-1-enyl)-4-[4-(2-ethoxy-ethyl-amino)-cyclohexyl]-phenyl}-amide | 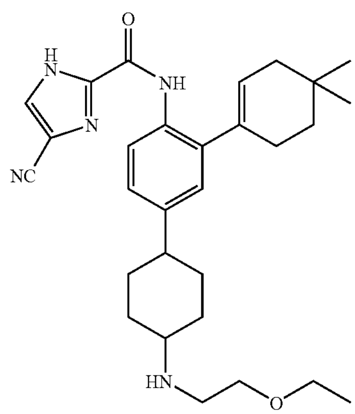 | Example 24 | (Pfaltz and Bauer Chemicals, Inc.) |
| 32 | 4-Cyano-1H-imidazole-2-carboxylic acid[4-{4-[bis-(2-hydroxy-ethyl)-amino]-cyclohexyl}-2-(4,4-dimethyl-cyclohex-1-enyl)-phenyl]-amide | 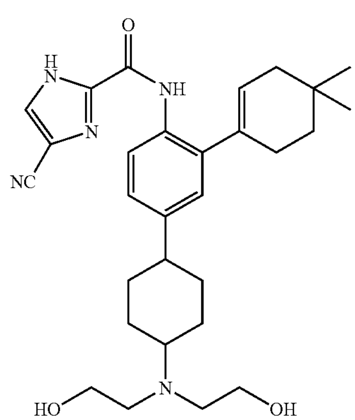 | Example 24 | |

| Example No. | Name | Structure | Procedure Reference | Reagents |
|---|---|---|---|---|
| 33 | 4-Cyano-1H-imidazole-2-carboxylic acid{2-(4,4-dimethyl-cyclohex-1-enyl)-4-[4-(2-methanesulfonyl-ethylamino)-cyclohexyl]-phenyl}-amide | 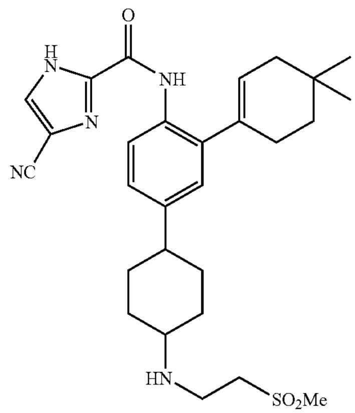 | Example 24 | H$_2$N~~SO$_2$Me (Apollo Scientific, Inc.) |
| 34 | 4-Cyano-1H-imidazole-2-carboxylic acid[4-[4-(dimethylcarbamoylmethyl-amino)-cyclohexyl]-2-(4,4-dimethyl-cyclohex-1-enyl)-phenyl]-amide | 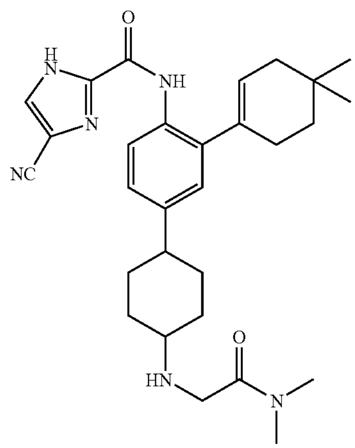 | Example 24 | (WO 2001025234 A1) |

EXAMPLE 35

4-Cyano-1H-imidazole-2-carboxylic acid {2-(4,4-dimethyl-cyclohex-1-enyl)-6-[1-(4-ethyl-piperazin-1-yl)-cyclopentyl]-pyridin-3-yl}-amide

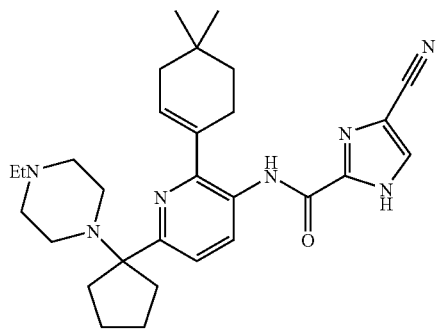

a) 6-Bromo-2-iodo-pyridin-3-ylamine

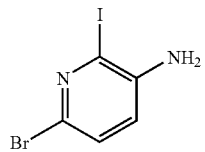

To a stirred solution of 6-bromo-pyridin-3-ylamine (10.2 g, 0.0580 mol) and Ag$_2$SO$_4$ (18.1 g, 0.0580 mol) in EtOH (150 mL) was added I$_2$ (7.59 g, 0.0580 mol) and the reaction was allowed to stir overnight. At this time hexane (200 mL) was added and the resultant mixture was filtered through Celite. The solvent was removed in vacuo, dissolved in CHCl$_3$ (200 mL), washed with aqueous saturated Na$_2$S$_2$O$_3$ (100 mL), water (1×100 mL), and dried (Na$_2$SO$_4$). The solvent was concentrated in vacuo and the residue was dissolved in hot EtOAc (100 mL), filtered and treated with hexanes (100 mL). Filtration gave 11.2 g (65%) of 6-bromo-2-iodo-pyridin-3-ylamine as a white crystalline material. $^1$H-NMR (CDCl$_3$; 400 MHz): δ 7.10 (d, 1H, J=8.2 Hz), 6.74 (d, 1H, J=8.2 Hz), 4.06 (br s, 2H).

b) 6-Bromo-2-(4,4-dimethyl-cyclohex-1-enyl)-pyridin-3-ylamine

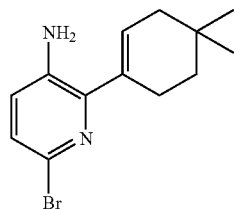 [SMILES: CC1(C)CC=C(c2nc(Br)ccc2N)CC1]

A solution of 6-bromo-2-iodo-pyridin-3-ylamine (as prepared in the previous step, 1.00 g, 3.35 mmol) in toluene (27 mL) and EtOH (13.5 mL) was treated with 2.0 M aq $Na_2CO_3$ (13.4 mL, 26.8 mmol) and 4,4-dimethyl-cyclohex-1-enylboronic acid (567 mg, 3.68 mmol). The mixture was degassed via sonication, placed under Ar, treated with $Pd(PPh_3)_4$ (271 mg, 0.234 mmol), and heated to 80° C. for 5 h. The cooled mixture was diluted with EtOAc (100 mL) and washed with water (2×50 mL). The combined aqueous layers were extracted with EtOAc (1×100 mL). The combined organic layers were dried over $MgSO_4$ and concentrated in vacuo. Silica gel chromatography of the residue on a Varian Mega-Bond Elut 50-g column with 10% EtOAc-hexane afforded 668 mg (71%) of 6-bromo-2-(4,4-dimethyl-cyclohex-1-enyl)-pyridin-3-ylamine as a tan solid. $^1$H-NMR ($CDCl_3$; 400 MHz): δ 7.06 (d, 1H, J=8.3 Hz), 6.85 (d, 1H, J=8.3 Hz), 5.95 (m, 1H), 3.86 (br s, 2H), 2.43-2.39 (m, 2H), 1.99-1.97 (m, 2H), 1.51 (t, 2H, J=6.4 Hz), 0.99 (s, 6H).

c) 4-Cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide

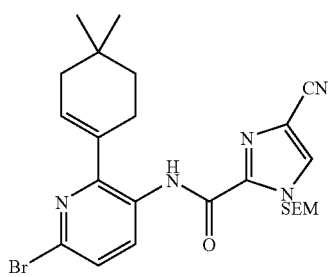 [SMILES: CC1(C)CC=C(c2nc(Br)ccc2NC(=O)c2nc(C#N)cn2COCC[Si](C)(C)C)CC1]

The title compound was prepared from 6-bromo-2-(4,4-dimethyl-cyclohex-1-enyl)-pyridin-3-ylamine (as prepared in the previous step, 60 mg, 0.21 mmol), potassium 4-cyano-1-(2-trimethylsilanyl-ethoxymethyl)-1H-imidazole-2-carboxylate (as prepared in Example 1, step (d), 91.0 mg, 0.290 mmol), PyBroP (157 mg, 0.330 mmol) and DIEA (91.0 μL, 0.520 mmol) according to the procedure in Example 1, step (f) (84 mg, 78%). $^1$H-NMR ($CDCl_3$; 400 MHz): δ 9.91 (s, 1H), 8.64 (d, 1H, J=8.6 Hz), 7.79 (s, 1H), 7.38 (d, 1H, J=8.6 Hz), 6.00 (m, 1H), 5.92 (s, 2H), 3.67 (m, 2H), 2.46 (m, 2H), 2.14 (m, 2H), 1.62 (t, 2H, J=6.3 Hz), 1.12 (s, 6H), 0.98 (m, 2H).

d) 5-Cyano-1H-imidazole-2-carboxylic acid [6-bromo-2-(4,4-dimethyl-cyclohex-1-enyl)-pyridin-3-yl]-amide

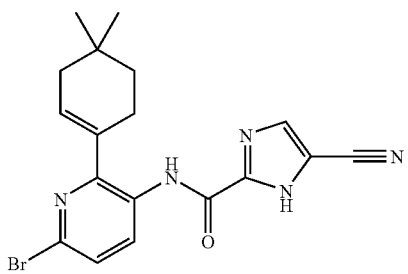 [SMILES: CC1(C)CC=C(c2nc(Br)ccc2NC(=O)c2ncc(C#N)[nH]2)CC1]

The title compound was prepared from 4-cyano-1-(2-trimethylsilanyl-ethoxymethyl)-1H-imidazole-2-carboxylic acid [6-bromo-2-(4,4-dimethyl-cyclohex-1-enyl)-pyridin-3-yl]-amide (as prepared in the previous step) according to the procedure in Example 1, step (g). $^1$H-NMR ($CD_3OD$; 400 MHz): δ 8.53 (d, 1H, J=8.8 Hz), 8.03 (s, 1H), 7.48 (d, 1H, J=8.8 Hz), 6.04-5.99 (m, 1H), 2.48-2.40 (m, 2H), 2.13-2.08 (m, 2H), 1.61 (t, 2H, J=6.0 Hz), 1.09 (s, 6H). Mass spectrum (ESI, m/z): Calcd. for $C_{18}H_{18}BrN_5O$, 400.1 (M+H), found 400.0.

e) 4-Cyano-1H-imidazole-2-carboxylic acid [2-(4,4-dimethyl-cyclohex-1-enyl)-6-(1-hydroxy-cyclopentyl)-pyridin-3-yl]-amide

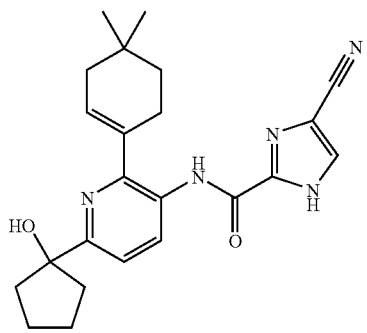 [SMILES: CC1(C)CC=C(c2nc(C3(O)CCCC3)ccc2NC(=O)c2nc(C#N)c[nH]2)CC1]

The title compound is prepared from 5-cyano-1H-imidazole-2-carboxylic acid [6-bromo-2-(4,4-dimethyl-cyclohex-1-enyl)-pyridin-3-yl]-amide (as prepared in the previous step) and cyclopentanone according to the procedure in Example 1, step (h).

f) 4-Cyano-1H-imidazole-2-carboxylic acid {2-(4,4-dimethyl-cyclohex-1-enyl)-4-[1-(4-ethyl-piperazin-1-yl)-cyclopentyl]-phenyl}-amide The title compound is prepared from 4-cyano-1H-imidazole-2-carboxylic acid [2-(4,4-dimethyl-cyclohex-1-enyl)-6-(1-hydroxy-cyclopentyl)-pyridin-3-yl]-amide (as prepared in the previous step), N-ethylpiperazine, and thionyl chloride in DCM solvent according to the procedure in Example 43.

EXAMPLE 36

4-Cyano-1H-imidazole-2-carboxylic acid {2-(4,4-dimethyl-cyclohex-1-enyl)-6-[1-(2-pyrrolidin-1-yl-ethoxy)-cyclopentyl]-pyridin-3-yl}-amide

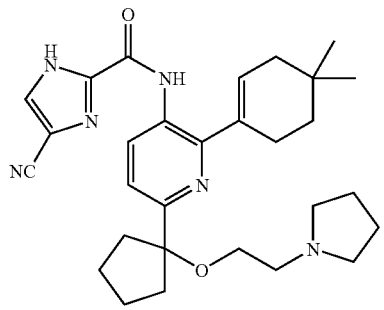

The title compound is prepared using 4-cyano-1H-imidazole-2-carboxylic acid [2-(4,4-dimethyl-cyclohex-1-enyl)-4-(1-hydroxy-cyclopentyl)-phenyl]-amide (as prepared in Example 3) and 2-pyrrolidin-1-yl-ethanol according to the procedure of Example 43, except replacing the $SOCl_2$ with 10 equivalents of trifluoroacetic acid and heating in a sealed tube at 50° C. for 8 h.

The following example is produced according to the procedures of previous examples with the corresponding reagents as indicated in the table below:

| Example No. | Name | Structure | Procedure Reference | Reagents |
|---|---|---|---|---|
| 37 | 4-Cyano-1H-imidazole-2-carboxylic acid{6-[1-(4-methyl-piperazin-1-yl)-cyclopentyl]-2-spiro[4.5]dec-7-en-8-yl-pyridin-3-yl}-amide | 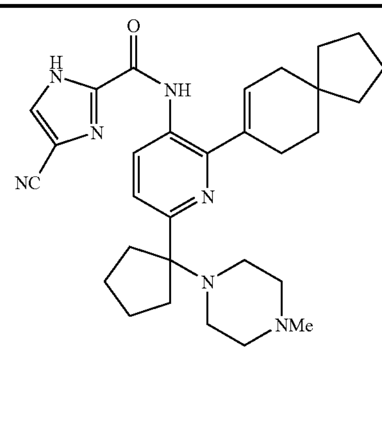 | Ex. 35 | WO2005063705 |

The following examples are produced according to procedures of previous examples with the corresponding reagents as indicated in the table below:

| Example No. | Name | Structure | Procedure Reference | Reagents |
|---|---|---|---|---|
| 38 | 4-[4-[(4-Cyano-1H-pyrrole-2-carbonyl)-amino]-3-(4,4-dimethyl-cyclohex-1-enyl)-phenyl]-cis-4-hydroxy-cyclohexanecarboxylic acid | 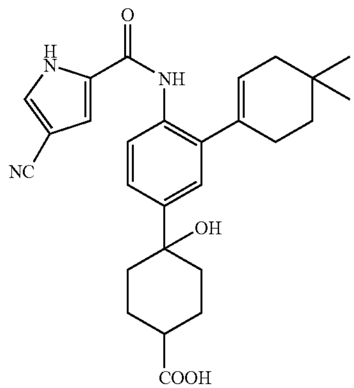 | Example 1, step (f); Example 2 | (Canadian J. Chem. 59, 2673 (1981)) |
| 39 | 4-[4-[(4-Cyano-1H-pyrrole-2-carbonyl)-amino]-3-(4,4-dimethyl-cyclohex-1-enyl)-phenyl]-cyclohexanecarboxylic acid | 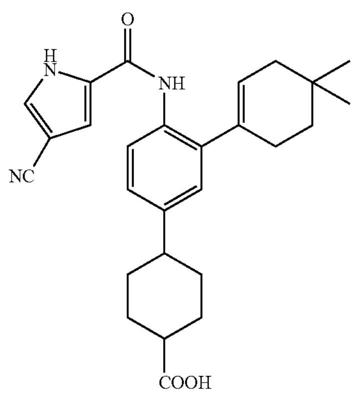 | Example 1, step (f); Example 18 | (Canadian J. Chem. 59, 2673 (1981)) |
| 40 | 4-Cyano-1H-imidazole-2-carboxylic acid[4-[4-(4-methyl-piperazin-1-yl)-cyclohexyl]-2-(4-methyl-piperidin-1-yl)-phenyl]-amide | 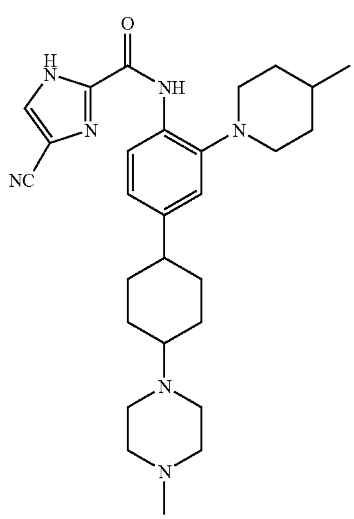 | Example 1, steps (f)-(g); Example 23; Example 24 | (WO 2005131022, A1); Tetrahedron Lett., 31, 3237–40 (1990)); 4-methyl-piperazine |

-continued

| Example No. | Name | Structure | Procedure Reference | Reagents |
|---|---|---|---|---|
| 41 | 4-Cyano-1H-imidazole-2-carboxylic acid[2-(4-methyl-piperidin-1-yl)-4-(4-morpholin-4-yl-cyclohexyl)-phenyl]-amide | 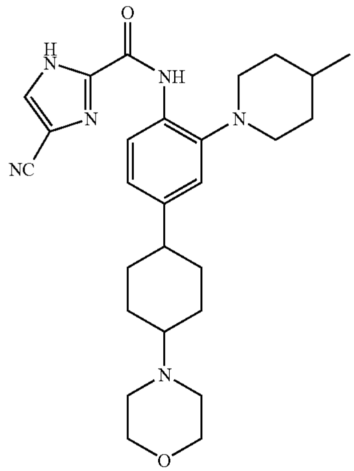 | Example 1, steps (f)-(g); Example 23; Example 24 | (WO 2005131022, A1); *Tetrahedron Lett.*, 31, 3237–40 (1990)); morpholine |
| 42 | 4-Cyano-1H-imidazole-2-carboxylic acid[4-{4-[(2-methoxy-ethyl)-methyl-amino]-cyclohexyl}-2-(4-methyl-piperidin-1-yl)-phenyl]-amide | 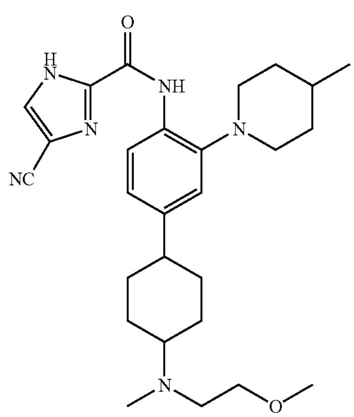 | Example 1, steps (f)-(g); Example 23; Example 24 | (WO 2005131022, A1); *Tetrahedron Lett.*, 31, 3237–40 (1990)); (Fluorochem, Inc.) |

EXAMPLE 43

4-Cyano-1H-imidazole-2-carboxylic acid {2-(4,4-dimethyl-cyclohex-1-enyl)-4-[1-(2-methoxy-ethylamino)-cyclohexyl]-phenyl}-amide

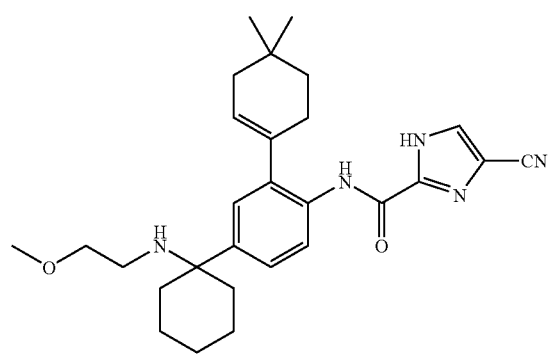 [SMILES: COCCNC1(c2ccc(NC(=O)c3nc(C#N)c[nH]3)c(C3=CCC(C)(C)CC3)c2)CCCCC1]

To a suspension of 4-cyano-1H-imidazole-2-carboxylic acid [2-(4,4-dimethyl-cyclohex-1-enyl)-4-(1-hydroxy-cyclohexyl)-phenyl]-amide (as prepared in Example 1, 42.0 mg, 0.100 mmol) in 1.5 mL of DCM at −15° C. was added SOCl$_2$ (22.0 μL, 0.300 mmol) under Ar. After stirring at RT for 1 h, the mixture was cooled to −15° C. To the reaction was then added 2-methoxyethylamine (70.0 μL, 0.800 mmol) and the resulting mixture was stirred at RT for 2 h. The mixture was diluted with EtOAc (30 mL) and washed with H$_2$O (2×10 mL) and brine (10 mL). After drying over Na$_2$SO$_4$ and concentrating in vacuo, the residue was purified by silica gel chromatography (1-5% MeOH/DCM) to afford the title compound (21.7 mg, 46%) as a white solid. $^1$H-NMR (1:1 CDCl$_3$/CD$_3$OD; 400 MHz): δ 8.40 (d, 1H, J=8.6 Hz), 7.79 (s, 1H), 7.44 (m, 1H), 7.32 (br s, 1H), 5.81 (m, 1H), 3.48 (t, 2H, J=5.1 Hz), 3.27 (s, 3H), 2.60 (t, 2H, J=5.1 Hz), 2.35-2.45 (m, 2H), 2.28-2.35 (m, 2H), 2.09-2.15 (m, 2H), 1.87-1.98 (m, 2H), 1.68-1.78 (m, 2H), 1.61 (t, 2H, J=6.3 Hz), 1.34-1.60 (m, 4H), 1.12 (s, 6H). Mass spectrum (APCI-neg, m/z): Calcd. for C$_{28}$H$_{37}$N$_5$O$_2$, 474.3 (M−H), found 474.5.

EXAMPLES 44 AND 45

4-Cyano-1H-imidazole-2-carboxylic acid [2-(4,4-dimethyl-cyclohex-1-enyl)-4-(cis-1-hydroxy-cis-4-morpholin-4-yl-cyclohexyl)-phenyl]-amide (44) and 4-Cyano-1H-imidazole-2-carboxylic acid [2-(4,4-dimethyl-cyclohex-1-enyl)-4-(cis-1-hydroxy-trans-4-morpholin-4-yl-cyclohexyl)-phenyl]-amide (45)

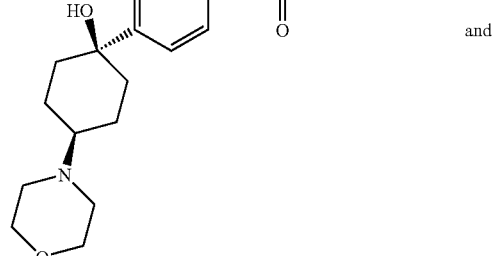

44 and

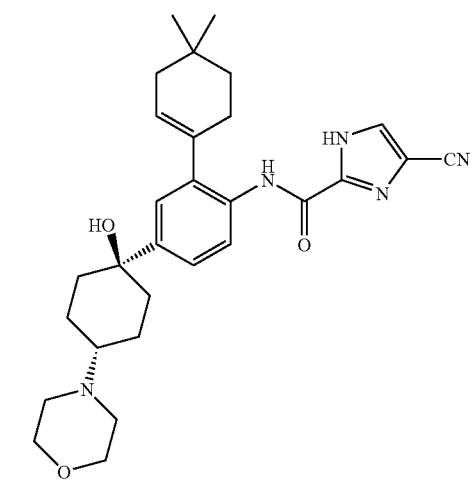

45 a) 4-(1,4-Dioxa-spiro[4.5]dec-8-yl)-morpholine hydrochloride

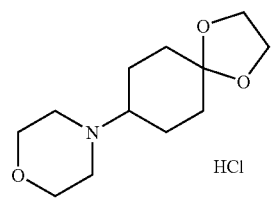 [SMILES: C1CN(C2CCC3(CC2)OCCO3)CCO1 ; Cl]

A solution of 1,4-dioxa-spiro[4.5]decan-8-one (5.00 g, 32.0 mmol) in CH$_2$Cl$_2$ (100 mL) was treated with morpholine (2.79 mL, 32.0 mmol), NaBH(OAc)$_3$ (9.50 g, 44.8 mmol), and acetic acid (1.84 mL, 32.0 mmol) at RT for 4 h. The mixture was quenched with NaOH (75 mL, 2N aq) and extracted with ether (3×150 mL). The combined organic layers were washed with water (1×100 mL) and brine (1×100 mL), dried over MgSO$_4$, and concentrated in vacuo to about 100 mL volume. HCl (9 mL, 4N in dioxane) was added dropwise with stirring. The resulting precipitate was filtered, rinsed with ether, and air-dried to afford the title compound (6.79 g, 80%) as a white solid. $^1$H-NMR (CD$_3$OD; 400 MHz): δ 4.13-4.05 (m, 2H), 3.90-3.80 (m, 2H), 3.54-3.46 (m, 2H), 3.32-3.17 (m, 3H), 2.23-2.14 (m, 2H), 1.95-1.75 (m, 4H), 1.72-1.61 (m, 2H).

b) 4-Morpholin-4-yl-cyclohexanone

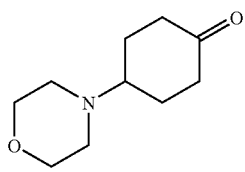

A suspension of 4-(1,4-dioxa-spiro[4.5]dec-8-yl)-morpholine hydrochloride (6.79 g, 25.7 mmol, as prepared in the previous step) in THF (100 mL) was treated with HCl (38.6 mL, 77.2 mmol, 2M aq) and heated to 80° C. for 4 h. The cooled mixture was treated with satd aq NaHCO$_3$ to pH 7 and extracted with ether (3×250 mL). The combined organic layers were dried over MgSO$_4$ and concentrated in vacuo to afford the title compound (2.22 g, 47%) as a colorless oil. $^1$H-NMR (CDCl$_3$; 400 MHz): δ 3.78-3.72 (m, 4H), 2.60-2.55 (m, 4H), 2.36-2.25 (m, 2H), 2.09-1.99 (m, 2H), 1.93-1.82 (m, 2H).

c) 4-Cyano-1H-imidazole-2-carboxylic acid [2-(4,4-dimethyl-cyclohex-1-enyl)-4-(cis-1-hydroxy-cis-4-morpholin-4-yl-cyclohexyl)-phenyl]-amide (44) and 4-Cyano-1H-imidazole-2-carboxylic acid [2-(4,4-dimethyl-cyclohex-1-enyl)-4-(cis-1-hydroxy-trans-4-morpholin-4-yl-cyclohexyl)-phenyl]-amide (45)

The title compounds were prepared from 4-cyano-1H-imidazole-2-carboxylic acid [4-bromo-2-(4,4-dimethyl-cyclohex-1-enyl)-phenyl]-amide (as prepared in Example 1, step (g)) and 4-morpholin-4-yl-cyclohexanone (as prepared in the previous step) according to the procedure as described in Example 22.

44: $^1$H-NMR (CD$_3$OD; 400 MHz): δ 8.12 (d, 1H, J=8.6 Hz), 7.93 (s, 1H), 7.39 (dd, 1H, J=8.6, 2.3 Hz), 7.34 (d, 1H, J=2.3 Hz), 5.73 (m, 1H), 3.72-3.74 (m, 4H), 2.69 (m, 4H), 2.43 (t, 1H, J=6.4 Hz), 2.26-2.34 (m, 2H), 2.07 (m, 2H), 1.77-1.92 (m, 8H), 1.59 (t, 2H, J=6.3 Hz), 1.07 (s, 6H). Mass spectrum (ESI, m/z): Calcd. for C$_{29}$H$_{37}$N$_5$O$_3$, 504.3 (M+H), found 504.2.

45: $^1$H-NMR (CD$_3$OD; 400 MHz): δ 8.20 (d, 1H, J=8.6 Hz), 7.97 (s, 1H), 7.45 (dd, 1H, J=8.6, 2.3 Hz), 7.36 (d, 1H, J=2.3 Hz), 5.74 (m, 1H), 3.69 (m, 4H), 2.54 (m, 4H), 2.36-2.45 (m, 2H), 2.28-2.36 (m, 3H), 2.08 (m, 2H), 1.92-2.02 (m, 2H), 1.48-1.69 (m, 6H), 1.09 (s, 6H). Mass spectrum (ESI, m/z): Calcd. for C$_{29}$H$_{37}$N$_5$O$_3$, 504.3 (M+H), found 504.3.

IV. Results

Fluorescence Polarization Competition Immunoassay

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms (Johnson & Johnson PRD) and 16.7 mM MgCl$_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM MgCl$_2$, 2% DMSO. Control reactions were ran in each plate: in positive and negative control wells, assay buffer (made 4% in DMSO) was substituted for the compound; in addition, positive control wells received 1.2 µL of 50 mM ethylenediaminetetraaceticacid (EDTA).

The plates were incubated at room temperature for 45 min. At the end of the incubation, the reaction was quenched with 1.2 µL of 50 mM EDTA (EDTA was not added to the positive control wells at this point; see above). Following a 5-min incubation, each well received 10 µL of a 1:1:3 mixture of anti-phosphotyrosine antibody, 10×, PTK green tracer, 10× (vortexed), FP dilution buffer, respectively (all from PanVera, cat. # P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. The reported IC$_{50}$ values are averages of three independent measurements.

CSF-1-Driven Mouse Bone-Marrow Derived Macrophages Assay

Macrophages are derived by culturing mouse bone marrow in alpha-MEM supplemented with 10% FCS and 50 ng/ml recombinant mouse CSF-1 in bacteriologic dishes. On the sixth day, macrophages are detached from dishes, washed, and resuspended to 0.05 million cells/ml in alpha-MEM containing 10% FCS. One hundred ul of cell suspension are distributed per well into 96 well culture plates. Wells are further supplemented with the addition of 50 ul media containing 15 ng/ml CSF-1, 3 uM Indomethacin, and 3× of a dilution series of test compounds. The cells are cultured for 30 hrs at 37 degrees and 5% CO2. During the final six hours, cultures are supplemented with an additional 30 ul of media containing a 1:500 dilution of bromodeoxyuridine (BrDU). At the end of the culture period, the plates are spun at 1000 RPM for 1 minute and 130 ul of media is removed with a pipet and replaced with 150 ul of fixative solution for 1 hour @ room temperature. The fixative is then dispelled from the plates and the plates allowed to air dry. Incorporation of BrDU into the fixed, dried cells is quantified using a specific ELISA.

Table 2 lists the assay results for representative compounds of the invention.

TABLE 2

| Example # | 1 nM c-fms; peptide Pi assay IC-50 (µM) | mCSF driven proliferation BMDM (Mouse) IC-50 (µM) |
| --- | --- | --- |
| 1 | 0.0059 | 0.072 |
| 2 | 0.00065 | 0.087 |
| 3 | 0.0023 | 0.0117 |

TABLE 2-continued

| Example # | 1 nM c-fms; peptide Pi assay IC-50 (μM) | mCSF driven proliferation BMDM (Mouse) IC-50 (μM) |
|---|---|---|
| 4 | 0.0095 | 0.099 |
| 14 | 0.02 | 0.15 |
| 27 | 0.0019 | 0.016 |
| 28 | 0.00099 | 0.0102 |
| 43 | 0.0029 | 0.111 |
| 44 | 0.00072 | 0.0028 |
| 45 | 0.0034 | 0.0085 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The invention claimed is:

1. A compound of Formula I

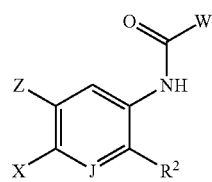

or a tautomer or pharmaceutically acceptable salt thereof, wherein:

W is

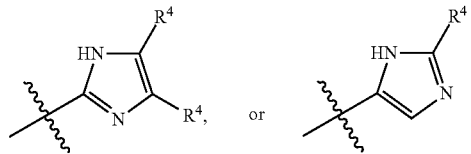

wherein each $R^4$ is independently H, F, Cl, Br, I, OH, $OCH_3$, $OCH_2CH_3$, $SC_{(1-4)}$alkyl, $SOC_{(1-4)}$alkyl, $SO_2C_{(1-4)}$alkyl, —$C_{(1-3)}$alkyl, —$CO_2R^d$, $CONR^eR^f$, C≡$CR^g$, or CN;

wherein $R^d$ is H, or —$C_{(1-3)}$alkyl;

$R^e$ is H, or —$C_{(1-3)}$alkyl;

$R^f$ is H, or —$C_{(1-3)}$alkyl; and $R^g$ is H, —$CH_2OH$, or —$CH_2CH_2OH$;

$R^2$ is cycloalkyl or spiro-substituted cycloalkenyl;

Z is H, F, or $CH_3$;

J is CH;

X is

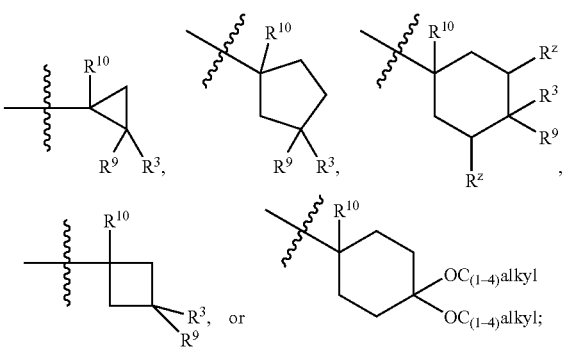

$R^z$ is H or —$C_{(1-4)}$alkyl, wherein both $R^z$ may have either syn or anti stereochemistry;

alternatively both $R^z$ in a syn relationship may be taken together to form —$(CH_2)_n$—, where n is 2 or 3;

$R^3$ is H, $C_{(1-4)}$alkyl, $CH_2CH_2NH_2$, $CH_2CH_2OR^a$, —$COCH_3$, $CONH_2$, or $CO_2R^a$;

$R^9$ is piperazinyl, which is optionally substituted by $C_{(1-4)}$alkyl;

$R^{10}$ is H, —$C_{(1-4)}$alkyl, —$OR^a$, —CN, —$NA^1A^2$, —$SO_2CH_3$, —$COOR^a$, —$CO_2CH_3$, —$CH_2$—$NA^1A^2$, —$CONA^1A^2$, —$CH_2OR^a$, —$OC_{(1-4)}$alkyl$OR^a$, —$NHCH_2CH_2CO_2R^a$, —$NHCH_2CH_2OR^a$, —$NR^aCH_2CH_2NA^1A^2$, —$OC_{(1-4)}$alkyl$NA^1A^2$, —$OCH_2CO_2R^a$, —$CH_2CO_2R^a$, —$CH_2CH_2SO_2C_{(1-4)}$alkyl, —$SO_2CH_2CH_2NA^1A^2$, —$SOCH_2CH_2NA^1A^2$, —$SCH_2CH_2NA^1A^2$, —$NHSO_2CH_2CH_2NA^1A^2$, or phenyl;

$A^1$ is H, —$C_{(1-4)}$alkyl, or $CH_2CH_2OR^a$; and $A^2$ is H, —$C_{(1-4)}$alkyl, $COR^a$, $CH_2CON(CH_3)_2$, —$CH_2CH_2OR^a$, —$CH_2CH_2SC_{(1-4)}$alkyl, —$CH_2CH_2SOC_{(1-4)}$alkyl, or —$CH_2CH_2SO_2C_{(1-4)}$alkyl.

2. The compound of claim 1, wherein:

W is

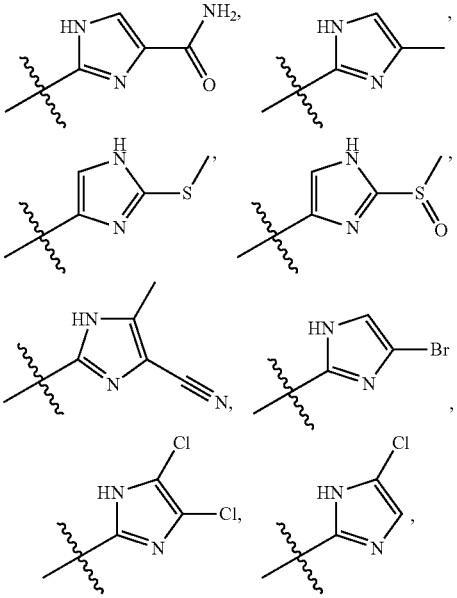

-continued

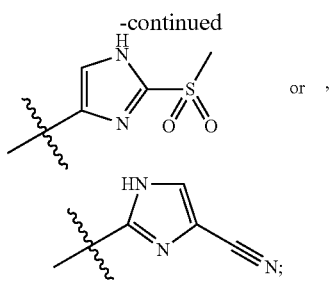

R² is

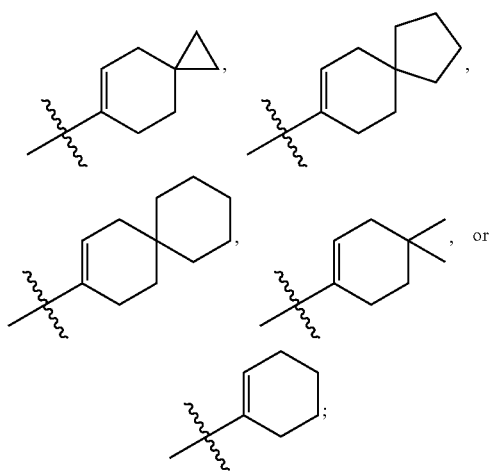

Z is H;
X is

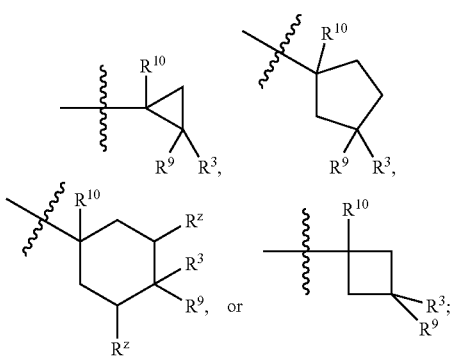

wherein R¹⁰ is H, —CO₂H, —CN, —OH, —CH₂NH₂, —NA¹A², —OCH₂CH₂NA¹A², or —NR$^a$CH₂CH₂NA¹A²;

A¹ is H, or —CH₃;

A² is H, —CH₂CH₂OCH₃, —COCH₃, or —CH₃;

R$^z$ is H, —CH₃, or may be taken together as CH₂CH₂—;

R³ is H, —COCH₃, —CH₃, —CO₂CH₃, —CONH₂, or —CO₂H; and

R⁹ is N-methyl-piperazinyl, N-ethyl-piperazinyl.

3. The compound of claim 2, wherein:
W is

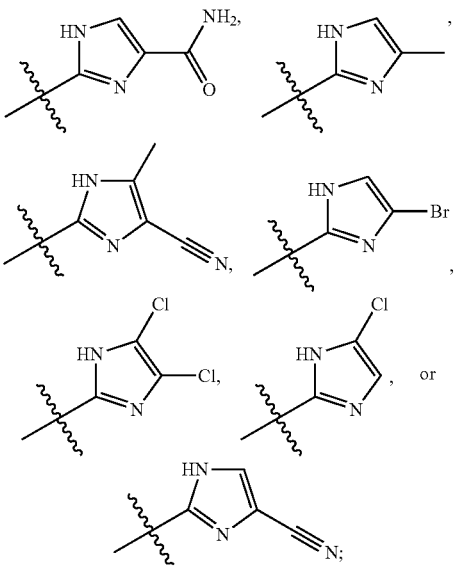

R² is

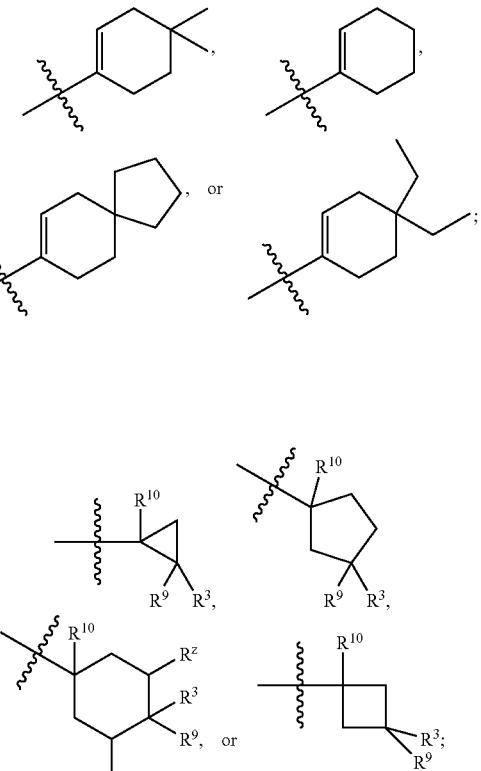

X is wherein R¹⁰ is H, —CO₂H, —CN, —OH, —CH₂NH₂, —NA¹A², —OCH₂CH₂NA¹A², or —NR$^a$CH₂CH₂NA¹A²;

A¹ is H, or —CH₃;

A² is H, —CH₂CH₂OCH₃, —COCH₃, or —CH₃;

$R_z$ is H, —CH₃, or may be taken together as —CH₂CH₂—;
$R^3$ is H, —COCH₃, —CH₃, —CO₂CH₃, —CONH₂, or —CO₂H; and
$R^9$ is N-methyl-piperazinyl, N-ethyl-piperazinyl.

4. The compound of claim 3, wherein:

W is

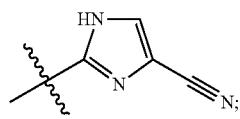 [SMILES: *c1nc(C#N)c[nH]1]

$R^2$ is

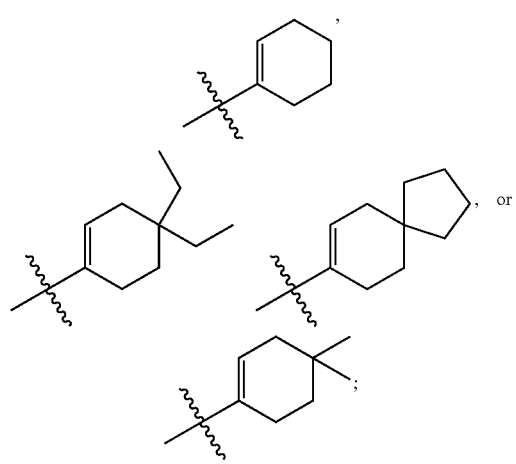

X is

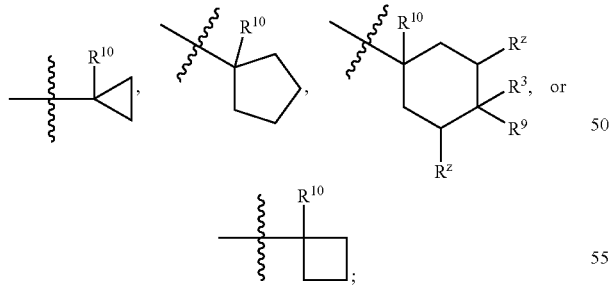

wherein $R^{10}$ is H, —CO₂H, —CN, —OH, —CH₂NH₂, —NA¹A², —OCH₂CH₂NA¹A², or —NR^aCH₂CH₂NA¹A²;
$A^1$ is H, or —CH₃;
$A^2$ is H, —CH₂CH₂OCH₃, —COCH₃, or —CH₃;
$R^z$ is H, —CH₃, or may be taken together as —CH₂CH₂—;
$R^3$ is H, —COCH₃, —CH₃, —CO₂CH₃, —CONH₂, or —CO₂H; and
$R^9$ is N-methyl-piperazinyl, N-ethyl-piperazinyl.

5. A pharmaceutical composition, comprising a compound of claim 1 and a pharmaceutically acceptable carrier.

6. A pharmaceutical dosage form comprising a pharmaceutically acceptable carrier and from about 0.5 mg to about 10 g of at least one compound of claim 1.

7. A dosage form according to claim 6 adapted for parenteral or oral administration.

8. A compound selected from the group consisting of:

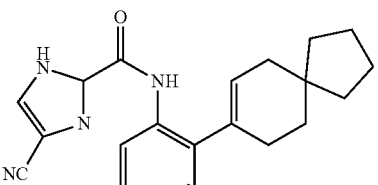
;

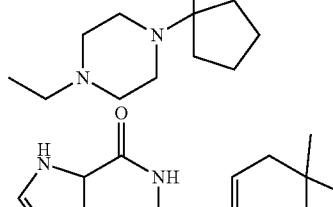
; and

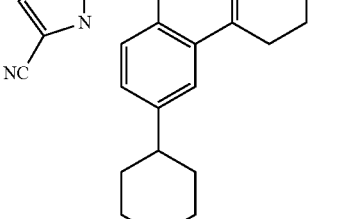

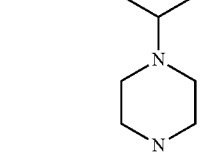

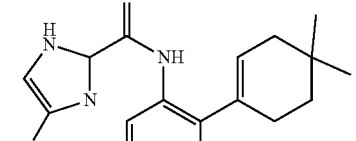
;

or a tautomer or pharmaceutically acceptable salt thereof.

9. The compound of claim 4, wherein:
W is
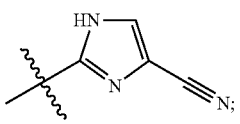 [SMILES: *c1nc(C#N)c[nH]1]
$R^2$ is
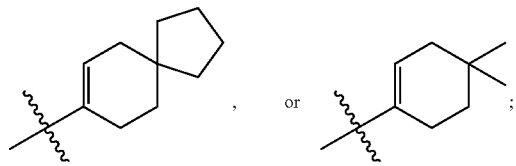
X is
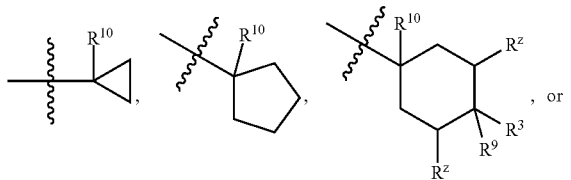
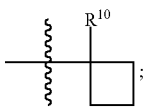
wherein $R^{10}$ is H, —CO$_2$H, —CN, —OH, —CH$_2$NH$_2$, —NA$^1$A$^2$, —OCH$_2$CH$_2$NA$^1$A$^2$, or —NR$^a$CH$_2$CH$_2$NA$^1$A$^2$;
$A^1$ is H, or —CH$_3$;
$A^2$ is H, —CH$_2$CH$_2$OCH$_3$, —COCH$_3$, or —CH$_3$;
$R^z$ is H, —CH$_3$, or may be taken together as —CH$_2$CH$_2$—;
$R^3$ is H, —COCH$_3$, —CH$_3$, —CO$_2$CH$_3$, —CONH$_2$, or —CO$_2$H; and
$R^9$ is N-methyl-piperazinyl, N-ethyl-piperazinyl.
* * * * *